United States Patent
Cheng et al.

(10) Patent No.: US 11,098,021 B2
(45) Date of Patent: Aug. 24, 2021

(54) PHENYLSULFONAMIDO-BENZOFURAN DERIVATIVES AND USES THEREOF IN THE TREATMENT OF PROLIFERATIVE DISEASES

(71) Applicants: Memorial Sloan-Kettering Cancer Center, New York, NY (US); Albert Einstein College of Medicine, Inc., Bronx, NY (US)

(72) Inventors: Emily H. Cheng, Englewood Cliffs, NJ (US); Paul Jeng, New Rochelle, NY (US); Ouathek Ouerfelli, Fort Lee, NJ (US); James Hsieh, Englewood Cliffs, NJ (US); Guangli Yang, Syosset, NY (US); Evripidis Gavathiotis, Flushing, NY (US)

(73) Assignees: Memorial Sloan-Kettering Cancer Center, New York, NY (US); Albert Einstein College of Medicine, Inc., Bronx, NY (US)

(*) Notice: Subject to any disclaimer, the term of this patent is extended or adjusted under 35 U.S.C. 154(b) by 0 days.

(21) Appl. No.: 15/752,126

(22) PCT Filed: Aug. 12, 2016

(86) PCT No.: PCT/US2016/046897
§ 371 (c)(1),
(2) Date: Feb. 12, 2018

(87) PCT Pub. No.: WO2017/027845
PCT Pub. Date: Feb. 16, 2017

(65) Prior Publication Data
US 2018/0237407 A1 Aug. 23, 2018

Related U.S. Application Data

(60) Provisional application No. 62/253,030, filed on Nov. 9, 2015, provisional application No. 62/204,385, filed on Aug. 12, 2015.

(51) Int. Cl.
*C07D 307/84* (2006.01)
*A61K 31/343* (2006.01)
(Continued)

(52) U.S. Cl.
CPC .......... *C07D 307/84* (2013.01); *A61K 31/343* (2013.01); *A61P 19/02* (2018.01);
(Continued)

(58) Field of Classification Search
CPC ........ A61K 31/343; A61P 19/02; A61P 35/00; A61P 35/02; A61P 37/00; C07D 307/82; C07D 307/84
(Continued)

(56) References Cited

U.S. PATENT DOCUMENTS 5,223,510 A 6/1993 Gubin et al.
6,570,002 B1* 5/2003 Hardwick .......... C07K 14/4747
536/23.1
(Continued)

FOREIGN PATENT DOCUMENTS

EP 0471609 A1 2/1992
FR 2962649 A1 1/2012
(Continued)

OTHER PUBLICATIONS

Aisha Shamas-Din et al (Mechanisms of Action of Bcl-2 Family Proteins Cold Spring Harb Perspect Biol. Apr. 2013; 5(4).*
(Continued)

*Primary Examiner* — Sabiha N Qazi
(74) *Attorney, Agent, or Firm* — Wolf, Greenfield & Sacks, P.C.

(57) ABSTRACT

Described herein are phenylsulfonamido-benzofuran derivatives, and pharmaceutically acceptable salts thereof. Also provided are pharmaceutical compositions, methods, uses, and kits involving compounds of Formulae (I), (II), (III), (IV), (V), or (VI) for treating and/or preventing proliferative diseases (e.g. cancers, inflammatory diseases, and autoimmune diseases) in a subject. The compounds and pharmaceutical compositions as described herein inhibit at least one protein of the BCL-2 family in a biological sample or subject to treat and/or prevent a proliferative disease. In certain embodiments, compounds described herein are selective inhibitors of MCL-1, a BCL-2 family member protein.

(Continued)

-continued

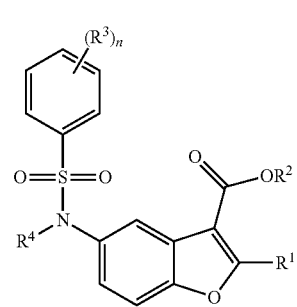
(III)

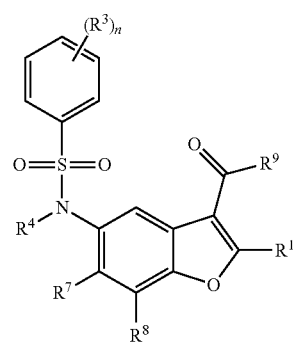

(IV)

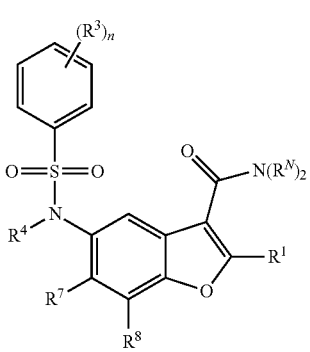

(V)

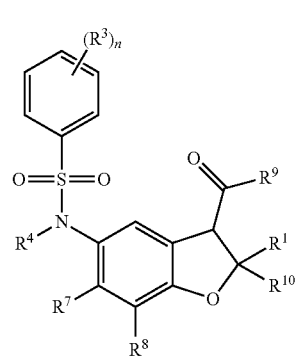

(VI)

25 Claims, 4 Drawing Sheets

(51) Int. Cl.
*C07D 307/82* (2006.01)
*A61P 35/00* (2006.01)
*A61P 37/00* (2006.01)
*A61P 19/02* (2006.01)
*A61P 35/02* (2006.01)

(52) U.S. Cl.
CPC ............... *A61P 35/00* (2018.01); *A61P 35/02* (2018.01); *A61P 37/00* (2018.01); *C07D 307/82* (2013.01)

(58) Field of Classification Search
USPC ......................................................... 514/469
See application file for complete search history.

(56) References Cited

U.S. PATENT DOCUMENTS

| | | | |
|---|---|---|---|
| 7,354,928 B2 | 4/2008 | Wang | |
| 8,501,811 B2* | 8/2013 | Hsieh | .................... C07C 327/42 |
| | | | 514/261.1 |
| 2003/0008924 A1 | 1/2003 | Wang et al. | |
| 2005/0085420 A1* | 4/2005 | Korsmeyer | ............ A61K 38/17 |
| | | | 514/1.4 |
| 2012/0077806 A1 | 3/2012 | Donato et al. | |
| 2012/0172285 A1 | 7/2012 | Walensky et al. | |
| 2015/0246955 A1* | 9/2015 | Walensky | ............... A61K 38/08 |
| | | | 530/326 |
| 2018/0237406 A1* | 8/2018 | Cheng | ..................... A61P 35/02 |
| 2018/0335421 A1* | 11/2018 | Cheng | ............... C23C 16/45536 |

FOREIGN PATENT DOCUMENTS

| | | |
|---|---|---|
| JP | 2004-529852 A | 9/2004 |
| JP | 2013-504536 | 2/2013 |
| WO | WO 2002/024636 A2 | 3/2002 |
| WO | WO 2008/017123 A1 | 2/2008 |
| WO | WO 2011/029842 A1 | 3/2011 |
| WO | WO 2012/017166 A2 | 2/2012 |
| WO | WO 2013/033520 A1 | 3/2013 |
| WO | WO 2013/134376 A1 | 9/2013 |
| WO | WO 2014/047427 A2 | 3/2014 |
| WO | WO 2014/109696 A1 | 7/2014 |
| WO | WO 2017/027845 A1 | 2/2017 |

OTHER PUBLICATIONS

[No Author Listed] Enamine. Compound Management. 2015. Retrieved from http://www.enamine.net/index.php?option=com_content&task=view&id=106 on Apr. 13, 2015.
CAS Registry No. 848335-97-7. Apr. 12, 2005. Enamine Chemical Library.
CAS Registry No. 848336-03-8. Apr. 12, 2005. Enamine Chemical Library.
Wan et al., Small-molecule Mcl-1 inhibitors: Emerging anti-tumor agents. Eur J Med Chem. Feb. 25, 2018;146:471-482. doi:10.1016/j.ejmech.2018.01.076. Epub Jan. 31, 2018.
International Preliminary Report on Patentability, dated Feb. 22, 2018, in connection with Application No. PCT/US2016/046889.
International Search Report and Written Opinion, dated Oct. 31, 2016, in connection with Application No. PCT/US2016/046889.
International Preliminary Report on Patentability, dated May 31, 2018, in connection with Application No. PCT/US2016/062789.
International Search Report and Written Opinion, dated Jan. 30, 2017, in connection with Application No. PCT/US2016/062789.
International Preliminary Report on Patentability, dated Feb. 22, 2018, in connection with Application No. PCT/US2016/046897.
International Search Report and Written Opinion, dated Oct. 25, 2016, in connection with Application No. PCT/US2016/046897.
Avdeenko et al., Reactions of N-arylsulfonylquinone imines with enamines. Russian J Org Chem. Aug. 2011;47:1169.
CAS accession No. 0087615692. Sep. 15, 2014.
CAS accession No. 2014:1583652. Sep. 22, 2014. Kannan et al.
CAS accession No. 848334-49-6. Apr. 12, 2005.
CAS accession No. 848334-54-3. Apr. 12, 2005.
CAS accession No. 848334-57-6. Apr. 12, 2005.
CAS accession No. 848335-86-4. Apr. 12, 2005.
CAS No. FRXXBL. 2012.
CAS No. IVUKAR. 1973.

(56) References Cited

OTHER PUBLICATIONS

CAS No. PIXXD2. WO 2012/017166 Feb. 9, 2012.
CAS No. RJOCEQ. Avdeenko et al. Reactions of N-arylsulfonylquinone imines with enamines. Russian J Organic Chemistry. 2011;47(8):1169-1180.
Chen et al., Identification of a potent inhibitor targeting human lactate dehydrogenase A and its metabolic modulation for cancer cell line. Bioorganic Med Chem Lett. Nov. 10, 2015;26(1):72-75.
Czabotar et al., Control of apoptosis by the BCL-2 protein family: implications for physiology and therapy. Nat Rev Mol Cell Biol. Jan. 2014;15(1):49-63.
Danial et al., Cell death: critical control points. Cell. Jan. 23, 2004;116(2):205-19.
Fuchs et al., Programmed cell death in animal development and disease. Cell. Nov. 11, 2011;147(4):742-58.
Kannan et al., Discovery of inhibitors of Schistosoma mansoni HDAC8 by combining homology modeling, virtual screening, and in vitro validation. J Chem Inf Model. Oct. 27, 2014;54(10):3005-19. doi:10.1021/ci5004653. Epub Oct. 2, 2014.
Nagarajan et al., Tubulin inhibitor identification by bioactive conformation alignment pharmacophore-guided virtual screening. Chem Biol Drug Des. Nov. 2015;86(5):998-1016. doi:10.1111/cbdd.12568. Epub May 5, 2015.
Noble et al., Conformational flexibility of the Dengue virus RNA-dependent RNA polymerase revealed by a complex with an inhibitor. J Virol. May 2013;87(9):5291-5. doi:10.1128/JVI.00045-13. Epub Feb. 13, 2013.
Oltersdorf et al., An inhibitor of Bcl-2 family proteins induces regression of solid tumours. Nature. Jun. 2, 2005;435(7042):677-81. Epub May 15, 2005.
Titov et al., Preparation of 2-methyl-3-acetyl-5-arenesulfonamidobenzofurans. Izvestiya Vysshikh Uchebnykh Zavedenii, Khimiya i Khimicheskaya Tekhnologiya (1973), 16(7), 1055-8.
Yang et al., Structure-based virtual screening for identification of novel 11beta-HSD1 inhibitors. Eur J Med Chem. Mar. 2009;44(3):1167-71. doi: 10.1016/j.ejmech.2008.06.005. Epub Jun. 20, 2008.
Youle et al. The BCL-2 protein family: opposing activities that mediate cell death. Nat Rev Mal Cell Biol. Jan. 2008;9(1):47-59.
[No Author Listed] CAS Registry No. 402474-81-1. Dated Mar. 21, 2002.
[No Author Listed] CAS Registry No. 448196-37-0. Dated Sep. 9, 2002.
[No Author Listed] CAS Registry No. 848315-71-9. STN Entry date Apr. 12, 2005.

* cited by examiner

| | F9 | G7 | A8 | M | MCLin |
|---|---|---|---|---|---|
| EC50 (μM) in H23 | 2.61 | 1.483 | 1.34 | 0.695 | 0.667 |
| EC50 (μM) in H82 | 1.072 | 0.971 | 0.518 | 0.227 | 0.336 |
| EC50 (μM) in Bax-/-Bak-/- MEFs | >100 | >100 | >100 | >100 | >100 |

Figure 3

PHENYLSULFONAMIDO-BENZOFURAN DERIVATIVES AND USES THEREOF IN THE TREATMENT OF PROLIFERATIVE DISEASES

RELATED APPLICATIONS

The present application is a national stage filing under 35 U.S.C. § 371 of international PCT application, PCT/US2016/046897, filed Aug. 12, 2016, which claims priority under 35 U.S.C. § 119(e) to U.S. provisional patent applications, U.S. Ser. No. 62/253,030, filed Nov. 9, 2015, and U.S. Ser. No. 62/204,385, filed Aug. 12, 2015, each of which is incorporated herein by reference.

GOVERNMENT SUPPORT

This invention was made with government support under grant numbers CA098320 and CA125562 awarded by the National Institutes of Health. The government has certain rights in the invention.

BACKGROUND OF THE INVENTION

Apoptosis is a process of programmed cell death that eliminates unwanted and potentially dangerous cells, which is essential for the successful development and maintenance of tissue homeostasis in all multicellular organisms, and provides a defense mechanism against cancer and viral infection. Apoptosis can be initiated through two distinct pathways. The extrinsic pathway is initiated by ligand binding to the cell surface "death receptors" such as Fas and TNF-R1, whereas the intrinsic pathway is activated by a wide variety of cellular stress including DNA damage, cytokine/growth factor deprivation, and ER stress. (Danial et al., Cell, 2004, 116, 205-219). Both extrinsic and intrinsic apoptotic pathways lead to activation of caspases that cleave substrates at specific motifs bearing aspartate residues. Caspases are executioners of apoptosis since processing of cellular substrates by these enzymes leads to the biochemical and morphological changes associated with apoptosis. Mitochondria play a key role in mammalian apoptosis because multiple apoptotic stimuli culminate in mitochondrial outer membrane permeabilization (MOMP), resulting in the release of cytochrome c and other apoptogenic factors from the mitochondria into the cytosol to activate caspases. Deregulation of apoptosis contributes to a variety of pathological processes (Fuchs et al., Cell, 2011, 147, 1-17). Insufficient apoptosis can manifest as cancer or autoimmunity, while accelerated apoptosis is evident in neurodegenerative disorders like Parkinson's disease, Alzheimer's disease, immunodeficiency, and infertility.

Central players of the mitochondrion-dependent apoptotic program are the BCL-2 family proteins (Czabotar et al., Nat. Rev. Mol. Cell Biol., 2014, 15, 49-63), consisting of (1) multidomain anti-apoptotic BCL-2, BCL-$X_L$, and MCL-1, (2) multidomain pro-apoptotic BAX and BAK, and (3) pro-apoptotic BH3-only molecules. Multidomain members contain all four BCL-2 homology domains (BH1-4) whereas BH3s only share sequence homology within the BH3 domain. The decision of a given cell to undergo mitochondrial outer membrane permeabilization (MOMP) is determined by the interplays among these three BCL-2 subfamilies. BAX and BAK are the essential effectors responsible for MOMP whereas BCL-2, BCL-$X_L$, and MCL-1 preserve mitochondrial integrity. The BH3-only molecules are death sentinels that relay upstream apoptotic signals to initiate apoptosis by either activating BAX and BAK to form death machinery or inactivating the survival proteins BCL-2, BCL-$X_L$, and MCL-1. BH3-only molecules execute their function through binding of their BH3 domains into the hydrophobic binding groove (or canonical dimerization pocket) of multidomain pro-apoptotic or anti-apoptotic members.

The BH3-only proteins are thought to function as death signal sensors and play a major role in transducing signals from the cytosol to the mitochondria. Anti-apoptotic members such as BCL-2, BCL-$X_L$ and MCL-1 protect cells from many different apoptotic stimuli and are thus important for cell survival (Youle et al., Nat. Rev. Mol. Cell Biol., 2008, 9, 47-59). To evade apoptotic checkpoints, cancer cells often overexpress anti-apoptotic BCL-2 family proteins including BCL-2, BCL-$X_L$, and MCL-1. Overexpression of the anti-apoptotic BCL-2 family proteins contributes to tumor initiation, progression, and resistance to anticancer treatments. Hence, targeting the BCL-2 family to promote apoptosis holds great promise for cancer therapy.

The anti-apoptotic BCL-2 members inhibit apoptosis by sequestering the proapoptotic BCL-2 members into inert complexes. Given that the hydrophobic dimerization groove of anti-apoptotic BCL-2 family proteins is critical for their prosurvival function, targeted inhibition of this binding groove can induce apoptosis in cancer cells by liberating trapped proapoptotic BCL-2 members. Using a NMR structure-based approach to target the hydrophobic dimerization groove of BCL-$X_L$, ABT-737 and its orally active derivative ABT-263 (navitoclax) were developed. These BH3 mimetics can bind with high affinity to BCL-$X_L$, BCL-2 and BCL-W and kill cells through a BAX- and BAK-dependent mechanism (Oltersdorf et al., Nature, 2005, 435, 677-681). However, these chemicals do not inhibit MCL-1 of which the hydrophobic dimerization groove appears structurally distinct from those of BCL-2 and BCL-$X_L$. Notably, due to the inherent limitations in using standard cell-free systems for targeting MCL-1, no clinically applicable MCL-1 inhibitors have been developed. Therefore, there is a further need to develop novel BCL-2 family inhibitors such as MCL-1 inhibitors for cancer therapies.

SUMMARY OF THE INVENTION

The apoptotic pathway is an ordered process of programmed cell death that is often altered in various pathologic conditions associated with either increased apoptosis or with decreased apoptosis (Fuchs et al., Cell, 2011, 147, 1-17). Modulating apoptosis by external means provides an important and promising approach that paves the way for a variety of therapeutic opportunities. For example, cancer is a condition associated with deregulated apoptosis, resulting in cells that display increased survival and resistance to anti-cancer treatments. Thus, inducing apoptosis is valuable as a defense mechanism against hyper proliferating cells. It was shown that anti-apoptotic BCL-2 family proteins govern the pro-survival pathway and are overexpressed in a variety of tumor types such as leukemia, lymphoma, lung cancer, melanoma, prostate cancer, and breast cancer. One of the aims of cancer treatment is to restore the apoptotic capabilities of cancer cells. Further, inhibitors of anti-apoptotic BCL-2 family proteins are needed in order to restore normal apoptotic processes and thus trigger tumor cell death. The present invention provides novel compounds that can lead to the development of new therapeutic strategies against proliferative diseases (e.g., cancer). The present invention also provides uses of compounds for the treatment of diseases (e.g., proliferative diseases, such as cancer)

In one aspect, the present invention provides novel compounds of Formulae (I), (II), (V), and (VI), and pharmaceutically acceptable salts, solvates, hydrates, polymorphs, co-crystals, tautomers, stereoisomers, isotopically labeled derivatives, prodrugs, and compositions thereof. The compounds of Formulae (I), (II), (V), and (VI) are inhibitors of BCL-2 family member proteins (e.g., MCL-1). The present invention further provides methods of using the inventive compounds (e.g., Formulae (I), (II), (V), and (VI)), and pharmaceutically acceptable salts, solvates, hydrates, polymorphs, co-crystals, tautomers, stereoisomers, isotopically labeled derivatives, prodrugs, and pharmaceutical compositions thereof, to prevent and/or treat proliferative diseases, such as cancers (e.g., leukemia, breast cancer, lung cancer, colon cancer, or cervical cancer), benign neoplasms, diseases associated with angiogenesis, inflammatory diseases, autoinflammatory diseases, and autoimmune diseases in a subject. In certain embodiments, the proliferative disease is cancer. In certain embodiments, the cancer is associated with aberrant activities of anti-apoptotic BCL-2 family proteins. In certain embodiments, the cancer is associated with aberrant activities of BCL-2. In certain embodiments, the cancer is associated with aberrant activities of BCL-$X_L$. In certain embodiments, the cancer is associated with aberrant activities of MCL-1. In certain embodiments, the compounds described herein can act as NOXA mimetics. NOXA is a pro-apoptotic BH3-only member of the BCL-2 protein family that specifically inactivates MCL-1 and has been shown to be involved in p53-mediated apoptosis. In certain embodiments, the compounds described herein mimic NOXA and bind to the hydrophotic dimerization groove of MCL-1 and induce apoptosis in MCL-1 addicted cancer cells. In certain embodiments, the compounds described herein induce the degradation of MCL-1 and thereby trigger apoptotis in MCL-1 addicted cancer cells. In certain embodiments, the proliferative disease is an inflammatory disease. In certain embodiments, the inflammatory disease is arthritis. In certain embodiments, the proliferative disease is an autoimmune disease. In certain embodiments, the autoimmune disease is autoimmune glomerulonephritis, immunoglobulinemia, or systemic lupus erythematosus (SLE).

In one aspect, the present invention provides compounds of Formula (I):

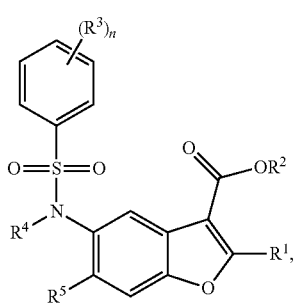

(I)

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^4$, $R^5$, and n are as defined herein.

In another aspect, the present invention provides compounds of Formula (II):

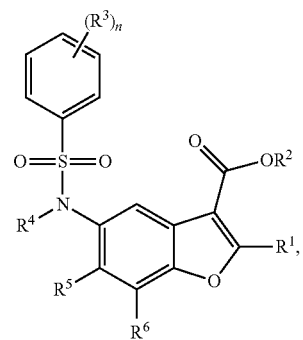

(II)

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^4$, $R^5$, $R^6$, and n are as defined herein.

In another aspect, the present invention provides compounds of Formula (I-a):

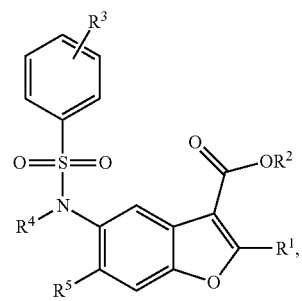

(I-a)

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^4$, and $R^5$ are as defined herein.

In one aspect, the present invention provides compounds of Formula (I-b):

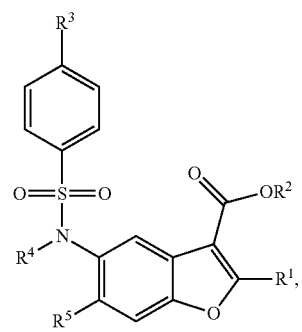

(I-b)

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^4$, and $R^5$ are as defined herein.

An exemplary compound of Formula (I) includes, but is not limited to:

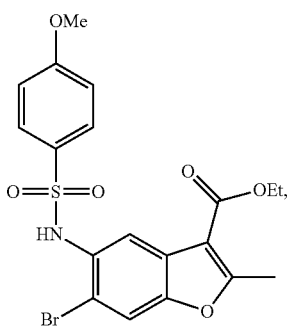

(Compound 1)

or a pharmaceutically acceptable salt, solvate, hydrate, polymorph, co-crystal, tautomer, stereoisomer, isotopically labeled derivative, or prodrug thereof.

In another aspect, the present invention provides compounds of Formula (V):

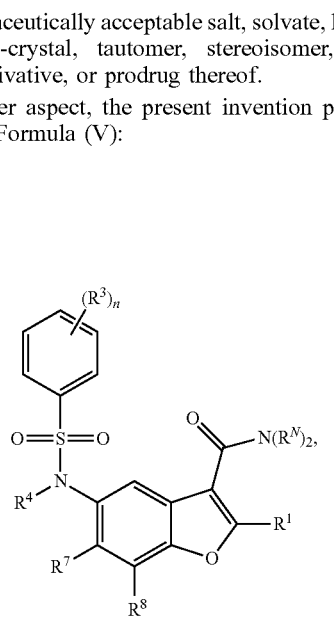

(V)

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^4$, $R^7$, $R^8$, and $R^N$ are as defined herein.

Exemplary compounds of Formula (V) include, but are not limited to:

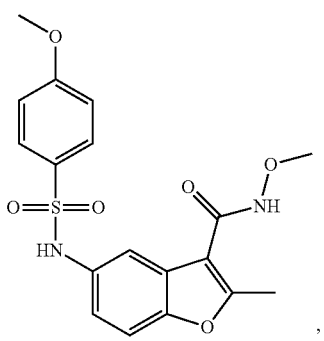

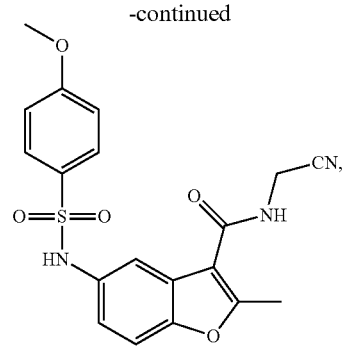

and pharmaceutically acceptable salts, solvates, hydrates, polymorphs, co-crystals, tautomers, stereoisomers, isotopically labeled derivatives, and prodrugs thereof.

In another aspect, the present invention provides compounds of Formula (VI):

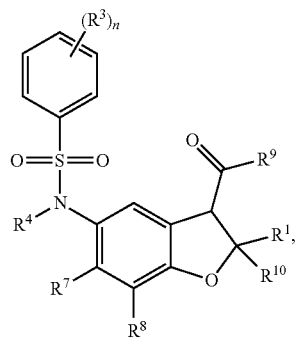

(VI)

and pharmaceutically acceptable salts, solvates, hydrates, polymorphs, co-crystals, tautomers, stereoisomers, isotopically labeled derivatives, and prodrugs thereof, wherein $R^1$, $R^3$, $R^4$, $R^7$, $R^8$, $R^9$, and $R^{10}$ are as defined herein.

In a particular embodiment, a compound of Formula (VI) is of the following formula:

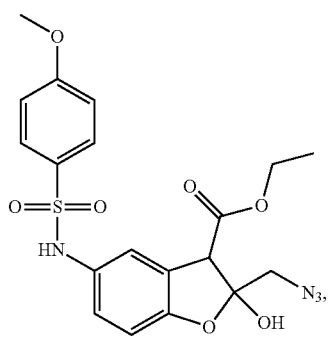 [SMILES: CCOC(=O)C1c2cc(NS(=O)(=O)c3ccc(OC)cc3)ccc2OC1(O)CN=[N+]=[N-]]

or a pharmaceutically acceptable salt solvate, hydrate, polymorph, co-crystal, tautomer, stereoisomer, isotopically labeled derivative, or prodrug thereof.

In another aspect, the present invention provides methods of using compounds of Formulae (I), (II), (III), (IV), (V), and (VI), and pharmaceutically acceptable salts, solvates, hydrates, polymorphs, co-crystals, tautomers, stereoisomers, isotopically labeled derivatives, prodrugs, and pharmaceutical compositions thereof, to prevent and/or treat proliferative diseases, such as cancers (e.g., leukemia, breast cancer, lung cancer, colon cancer, or cervical cancer), benign neoplasms, diseases associated with angiogenesis, inflammatory diseases, autoinflammatory diseases, and autoimmune diseases in a subject. In certain embodiments, the proliferative disease is cancer. In certain embodiments, the cancer is associated with aberrant activities of anti-apoptotic BCL-2 family proteins. In certain embodiments, the cancer is associated with aberrant activities of BCL-2. In certain embodiments, the cancer is associated with aberrant activities of BCL-$X_L$. In certain embodiments, the cancer is associated with aberrant activities of MCL-1. In certain embodiments, the compounds described herein can act as NOXA mimetics. NOXA is a pro-apoptotic BH3-only member of the BCL-2 protein family that specifically inactivates MCL-1 and has been shown to be involved in p53-mediated apoptosis. In certain embodiments, the compounds described herein mimic NOXA and bind to the hydrophotic dimerization groove of MCL-1 and induce apoptosis in MCL-1 addicted cancer cells. In certain embodiments, the compounds described herein induce the degradation of MCL-1 and thereby trigger apoptotis in MCL-1 addicted cancer cells. In certain embodiments, the proliferative disease is an inflammatory disease. In certain embodiments, the inflammatory disease is arthritis. In certain embodiments, the proliferative disease is an autoimmune disease. In certain embodiments, the autoimmune disease is autoimmune glomerulonephritis, immunoglobulinemia, or systemic lupus erythematosus (SLE).

The present invention provides methods of treating and/or preventing proliferative diseases with a compounds of Formula (IV):

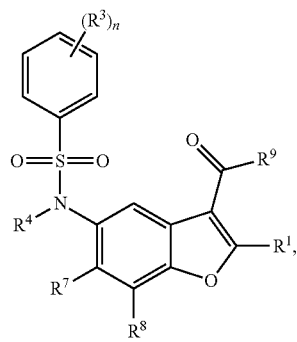

(IV)

and pharmaceutically acceptable salts, solvates, hydrates, polymorphs, co-crystals, tautomers, stereoisomers, isotopically labeled derivatives, and prodrugs thereof, wherein $R^1$, $R^3$, $R^4$, $R^7$, $R^8$, and $R^9$ are as defined herein.

Exemplary compounds of Formula (IV) include, but are not limited to:

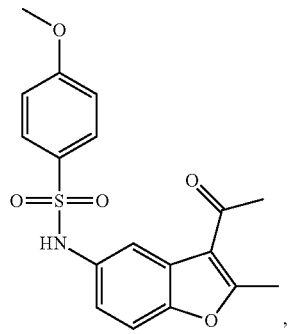

,

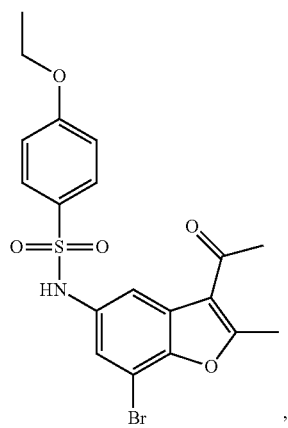

, and pharmaceutically acceptable salts, solvates, hydrates, polymorphs, co-crystals, tautomers, stereoisomers, isotopically labeled derivatives, and prodrugs thereof.

As described herein, the present invention provides methods treating and/or preventing a proliferative disease using a compound of Formula (III):

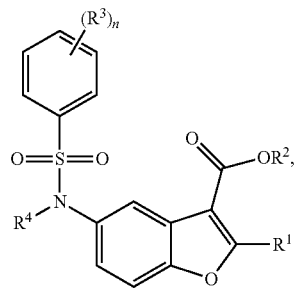

(III)

or pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, and $R^4$ are as defined herein.

Exemplary compounds of Formula (III) include, but are not limited to:
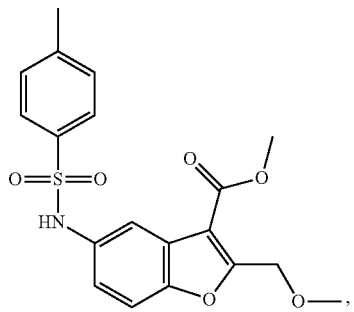
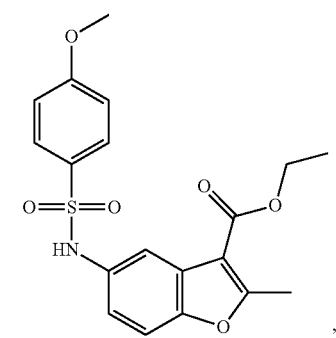
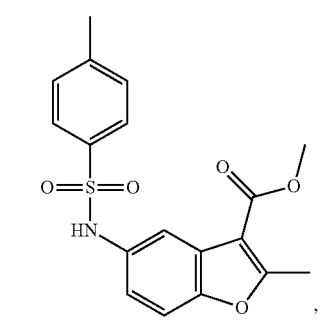
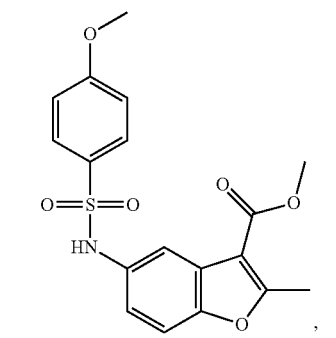
and pharmaceutically acceptable salts, solvates, hydrates, polymorphs, co-crystals, tautomers, stereoisomers, isotopically labeled derivatives, and prodrugs thereof.
Further exemplary compounds of Formula (III) include, but are not limited to:
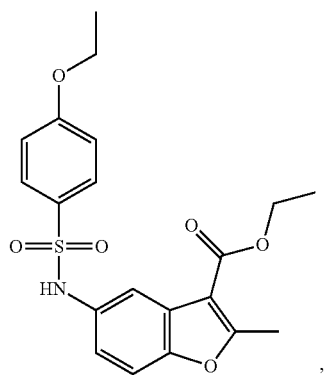
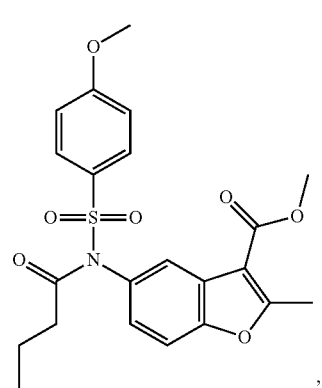
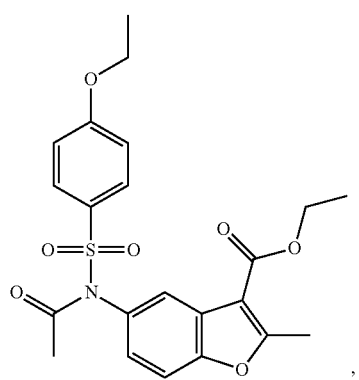
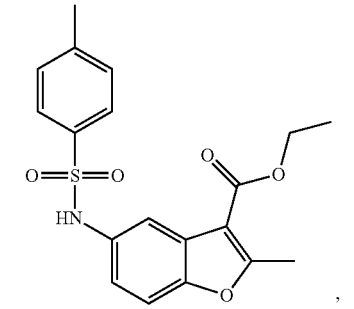

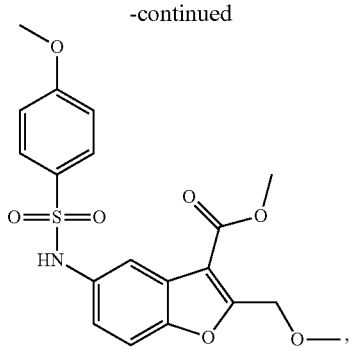

and pharmaceutically acceptable salts, solvates, hydrates, polymorphs, co-crystals, tautomers, stereoisomers, isotopically labeled derivatives, and prodrugs thereof.

The present invention also provides pharmaceutical compositions comprising a compound of Formula (I), (II), (III), (IV), (V), or (VI), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical compositions described herein include a therapeutically effective amount of a compound of Formula (I), (II), (III), (IV), (V), or (VI), or a pharmaceutically acceptable salt, solvate, hydrate, polymorph, co-crystal, tautomer, stereoisomer, isotopically labeled derivative, or prodrug thereof. The pharmaceutical composition may be useful for treating and/or preventing a proliferative disease, such as cancer, benign neoplasms, diseases associated with angiogenesis, inflammatory diseases, autoinflammatory diseases, and autoimmune diseases in a subject. In certain embodiments, the cancer is leukemia, breast cancer, lung cancer, colon cancer, liver cancer, bladder cancer, multiple myeloma, or lymphoma. In certain embodiments, the proliferative disease is an inflammatory disease. In certain embodiments, the inflammatory diseases is arthritis. In certain embodiments, the proliferative disease is an autoimmune disease. In certain embodiments, the autoimmune disease is autoimmune glomerulonephritis, immunoglobulinemia, or systemic lupus erythematosus (SLE).

In another aspect, the present invention provides methods for modulating the activity of at least one member of the BCL-2 family of proteins in a cell of a biological sample or a subject. In certain embodiments, the BCL-2 family protein is an anti-apoptotic BCL-2 member. In certain embodiments, the anti-apoptotic BCL-2 member is MCL-1. In certain embodiments, the compounds described herein selectively modulate activities of anti-apoptotic BCL-2 over any other BCL-2 family member. In certain embodiments, the compounds described herein selectively modulate activities of MCL-1 over any other BCL-2 family member. The method of modulating the activity of a BCL-2 family member comprises contacting the cell of a biological sample or a subject with a compound of Formula (I), (II), (III), (IV), (V), or (VI), or a pharmaceutically acceptable salt, solvate, hydrate, polymorph, co-crystal, tautomer, stereoisomer, isotopically labeled derivative, or prodrug thereof, or a pharmaceutical composition thereof.

In another aspect, the present invention provides methods for inducing apoptosis of a cell in a biological sample or subject. In certain embodiments, the compounds described herein induce apoptosis by modulating the BCL-2 pathway. In certain embodiments, the compounds described herein induce apoptosis by selectively modulating the MCL-1 pathway.

In certain embodiments, the compounds described herein induce apoptosis by selectively inhibiting MCL-1. In certain embodiments, the compounds described herein can act as NOXA mimetics (e.g., by binding to the hydrophotic dimerization groove of MCL-1). In certain embodiments, the compounds described herein induce the degradation of MCL-1. In certain embodiments, the compounds described herein selectively induce apoptosis in MCL-1-addicted cancer cells over other BCL-2- or BCL-$X_L$-addicted cancer cells. The method of inducing apoptosis comprises contacting the biological sample, or administering to the subject, a compound of Formula (I), (II), (III), (IV), (V), or (VI), or a pharmaceutically acceptable salt, solvate, hydrate, polymorph, co-crystal, tautomer, stereoisomer, isotopically labeled derivative, or prodrug thereof, or a pharmaceutical composition thereof. In another aspect, the present invention provides kits comprising a compound of Formula (I), (II), (III), (IV), (V), or (VI), or a pharmaceutically acceptable salt, solvate, hydrate, polymorph, co-crystal, tautomer, stereoisomer, isotopically labeled derivative, or prodrug thereof, or a pharmaceutical composition thereof. The kits of the invention may include a single dose or multiple doses of a compound of Formula (I), (II), (III), (IV), (V), or (VI), or a pharmaceutically acceptable salt, solvate, hydrate, polymorph, co-crystal, tautomer, stereoisomer, isotopically labeled derivative, or prodrug thereof, or a pharmaceutical composition thereof. The provided kits may be useful for the treatment of proliferative diseases. In certain embodiments, the proliferative disease is cancer. In certain embodiments, the proliferative disease is an inflammatory disease. In certain embodiments, the proliferative disease is an autoimmune disease. In certain embodiments, the kits described herein further include instructions for administering the compound of Formula (I), (II), (III), (IV), (V), or (VI), or the pharmaceutically acceptable salt, solvate, hydrate, polymorph, co-crystal, tautomer, stereoisomer, isotopically labeled derivative, or prodrug thereof, or the pharmaceutical composition thereof. The kits may also include packaging information describing the use or prescribing information for the subject or a health care professional. Such information may be required by a regulatory agency such as the U.S. Food and Drug Administration (FDA). The kit may also optionally include a device for administration of the compound or composition, for example, a syringe for parenteral administration.

The details of certain embodiments of the invention are set forth herein. Other features, objects, and advantages of the invention will be apparent from the Detailed Description, Figures, Examples, and Claims.

Definitions

Chemical Definitions

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's*

*Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_2$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic," as used herein, refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

The term "aliphatic," as used herein, refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-4}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3, 2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_3$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^+$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(=NH)NH(C$_{1-6}$ alkyl), —OC(=NH)NH$_2$, —NHC(=NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$(C$_{1-6}$ alkyl), —SO$_2$O(C$_{1-6}$ alkyl), —OSO$_2$(C$_{1-6}$ alkyl), —SO(C$_{1-6}$ alkyl), —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X is a counterion.

As used herein, the term "halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{cc}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O) SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(=O)(R$^{aa}$)$_2$, —OP(=O)(OR$^{cc}$)$_2$, and —OP(=O)(N(R$^{bb}$))$_2$, wherein R$^{aa}$, R$^{bb}$, and R$^{cc}$ are as defined herein.

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, —C(=S)O(R$^{X1}$), —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1l-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

These and other exemplary substituents are described in more detail in the Detailed Description, Examples, and Claims. The invention is not intended to be limited in any manner by the above exemplary listing of substituents.

Other Definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formulae (I), (II), (III), (IV), (V), or (VI) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $R.x\ H_2O$, wherein R is the compound, and x is a number greater than 0. A given compound may form more than one type of hydrates, including, e.g., monohydrates (x is 1), lower hydrates (x is a number greater than 0 and smaller than 1, e.g., hemihydrates ($R.0.5H_2O$)), and polyhydrates (x is a number greater than 1, e.g., dihydrates ($R.2H_2O$) and hexahydrates ($R.6H_2O$)).

As used herein, the term "tautomer" includes two or more interconvertable forms resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and/or solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formulae (I), (II), (III), (IV), (V), and (VI), which have cleavable groups and become by solvolysis or under physiological conditions the compounds of Formulae (I), (II), (III), (IV), (V), and (VI), which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy) alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formulae (I), (II), (III), (IV), (V), or (VI) may be preferred in certain instances.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound of Formula (I), (II), (III), (IV), (V), or (VI) refers to an amount sufficient to elicit a desired biological response, i.e., treating the condition. As will be appreciated by those of ordinary skill in this art, the effective amount of a compound of Formula (I), (II), (III), (IV), (V), or (VI) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor. In treating macular degeneration, an effective amount of an inventive compound may improve sight, reduce the risk of vision loss, or prevent central vision loss from worsening.

A "therapeutically effective amount" of a compound of Formula (I), (II), (III), (IV), (V), or (VI) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formula (I), (II), (III), (IV), (V), or (VI) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as matrix metalloproteinases (e.g., collagenases, gelatinases, and elastases); or 4) pathological angiogenesis as in proliferative retinopathy and tumor metastasis. Exemplary proliferative diseases include cancers (i.e., "malignant neoplasms"), benign neoplasms, diseases associated with angiogenesis or diseases associated with angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

As used herein, the term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and growth of new blood vessels. Normal angiogenesis occurs in the body of a healthy subject during wound healing and for restoring blood flow to tissues after injury. The body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can result in new blood vessels that feed diseased tissues and/or destroy normal tissues, and in the case of cancer, the new vessels can allow tumor cells to escape into the circulation and lodge in other organs (tumor metastases). In certain embodiments, the disease associated with angiogenesis is tumor angiogenesis. In certain embodiments, the diseases associated with angiogenesis include, but are not limited to breast cancer, colorectal cancer, esophageal cancer, gastrointestinal stromal tumor (GIST), kidney (renal cell) cancer, liver (adult primary) cancer, lymphoma, melanoma, lung cancer, ovarian epithelial cancer, pancreatic cancer, prostate cancer, stomach (gastric) cancer.

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyosifis, pemphigus, pemphigoid, diabetes (e.g., Type I), myasthenia gravis, Hashimoto's thyroditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis *nodosa*), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomylitis, optic neuritis, temporal arteritis, transverse myelitis, necrotizing fascilitis, and necrotizing enterocolitis. In certain embodiments, the inflammatory disease is arthritis.

As used herein, an "autoimmune disease" refers to a disease arising from an inappropriate immune response in the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppressants, e.g., medications which decrease the immune response. Exemplary autoimmune diseases include, but are not limited to, glomerulonephritis, Goodspature's syndrome, necrotizing vasculitis, lymphadenitis, peri-arteritis *nodosa*, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, perphigus vulgaris, ANCA-associated vasculitis (e.g., Wegener's granulomatosis, microscopic polyangiitis), urveitis, Sjogren's syndrome, Crohn's disease, Reiter's syndrome, ankylosing spondylitis, Lyme arthritis, Guillain-Barre syndrome, Hashimoto's thyroditis, and cardiomyopathy. In certain embodiments, the autoimmune disease is autoimmune glomerulonephritis, immunoglobulinemia, or systemic lupus erythematosus (SLE).

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behçet's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

As used herein, the term "apoptosis" refers to a regulated network of biochemical events which lead to a selective form of cell suicide and is characterized by readily observable morphological and biochemical. phenomena. Cells undergoing apoptosis show characteristic morphological and biochemical features. These features include chromatin aggregation or condensation, DNA fragmentation, nuclear and cytoplasmic condensation, partition of cytoplasm and nucleus into membrane bound vesicles (apoptotic bodies) which contain ribosomes, morphologically intact mitochondria and nuclear material. Cytochrome C release from mitochondria is seen as an indication of mitochondrial outer membrane permeabilization accompanying apoptosis.

As used herein, "inhibition", "inhibiting", "inhibit" and "inhibitor", and the like, refer to the ability of a compound to reduce, slow, halt, or prevent the activity of an anti-apoptotic BCL-2 family protein (also called "pro-survival BCL-2 family protein", e.g., MCL-1). In certain embodiments, such inhibition is of about 1% to 99.9%. In certain embodiments, the inhibition is about 1% to about 95%. In certain embodiments, the inhibition is about 5% to 90%. In certain embodiments, the inhibition is about 10% to 85%. In certain embodiments, the inhibition is about 15% to 80%. In certain embodiments, the inhibition is about 20% to 75%. In certain embodiments, the inhibition is about 25% to 70%. In certain embodiments, the inhibition is about 30% to 65%. In certain embodiments, the inhibition is about 35% to 60%. In certain embodiments, the inhibition is about 40% to 55%. In certain embodiments, the inhibition is about 45% to 50%. In certain embodiments, the inhibition is about 5%, 10%, 15%, 20%, 25%, 30%, 35%, 40%, 45%, 50%, 55%, 60%, 65%, 70%, 75%, 80%, 85%, 90%, 95%, or 99.9%.

When a compound is referred to as "selectively" inhibiting (i.e., when a compound is referred to as a "selective inhibitor" of) a specific BCL-2 family protein, the compound inhibits the specific BCL-2 family protein to a greater extent (e.g., more than 1-fold, not less than 2-fold, not less than 5-fold, not less than 10-fold, not less than 30-fold, not less than 100-fold, not less than 1,000-fold, or not less than 10,000-fold; and/or: not more than 2-fold, not more than 5-fold, not more than 10-fold, not more than 30-fold, not more than 100-fold, not more than 1,000-fold, or not more than 10,000-fold) than it inhibits a different BCL-2 family protein. A selective MCL-1 inhibitor (i.e., a compound that selectively inhibits MCL-1) inhibits the MCL-1 to a greater extent (e.g., more than 1-fold, not less than 2-fold, not less than 5-fold, not less than 10-fold, not less than 30-fold, not less than 100-fold, not less than 1,000-fold, or not less than 10,000-fold; and/or: not more than 2-fold, not more than 5-fold, not more than 10-fold, not more than 30-fold, not more than 100-fold, not more than 1,000-fold, or not more than 10,000-fold) than it inhibits a different BCL-2 family protein.

"BCL-2 family" refers to the apoptosis regulator BCL-2 family, a family of evolutionary-related proteins that regulate apoptosis in cells mainly by regulating the outer mitochondrial membrane integrity (Czabotar et al., *Nat. Rev. Mol. Cell Biol.*, 2014, 15, 49-63). BCL-2 family member proteins can be "pro-apoptotic" (e.g., BAX, BAD, BAK, BOK) or "anti-apoptotic" (e.g., parent BCL-2, BCL-$X_L$, BCL-W, MCL-1). Proteins of anti-apoptotic BCL-2 subfamily have up to four BH (BCL-2 homology) domains named BH1-4, and prevent cells from entering apoptosis. The BCL-2 pro-apoptotics can be further grouped into the multidomain pro-apoptotic and BH3-only proteins. The multidomain pro-apoptotic effectors, BAX and BAK, also contain four BH (BH1-4) regions and promote cell death by oligomerization-mediated mitochondria outer membrane permeabilization (MOMP). The BH3-only proteins share the BH3 region of sequence similarity. Members of this group include BID, BIM, BAD, BMF, BIK, PUMA, NOXA, HRK/DP5 (Harakiri), NIX, and BNIP3. The BH3 domain is 16 to 25 amino acid residues long and some BH3 peptides can promote apoptosis when introduced into cells. The three groups of BCL-2 family proteins form a delicately balanced network of opposing functions that regulates the cell's fate. In certain embodiments, the BCL-2 is a BCL-2 anti-apoptotic. In certain embodiments, the BCL-2 anti-apoptotic is BCL-2, BCL-W, BCL-$X_L$, or MCL-1. In certain embodiments, the BCL-2 anti-apoptotic is MCL-1. In certain embodiments, the compounds described herein may interact (e.g., inhibit or activate) with at least one anti-apoptotic protein member of the BCL-2 family, thereby enhancing apoptosis. In certain embodiments, the compounds described herein may interact with at least one anti-apoptotic protein member of the BCL-2 family and induce its degradation. In certain embodiments, the compounds described herein may interact with at least one pro-apoptotic protein member of the BCL-2 family, thereby enhancing apoptosis. Proteins that belong to the BCL-2 family may be referred to as "BCL-2 members" or "BCL-2 family members". Proteins that belong to the multidomain BCL-2 family include, but are not limited to BAK (BAK1), BAX, parent BCL-2, A1 (BCL2A1), BCL-XL (BCL2L1), BCL-W (BCL2L2), BCL-B (BCL2L10), BCL-RAMBO (BCL2L13), BCL-G (BCL2L14), BOK, and MCL-1. As used herein, "BCL-2" or "parent BCL-2" refers to B-cell lymphoma 2, an anti-apoptotic member of the BCL-2 family which helps regulate apoptosis in cells. As used herein, "BCL-$X_L$" refers to B-cell lymphoma-extra long. As used herein, "MCL-1" refers to induced myeloid leukemia cell differentiation protein MCL-1. Any isoforms of the BCL-2 family proteins described herein are contemplated as being within the scope of the invention.

The term "addicted" refers to a cell's dependence on an anti-apoptotic protein for survival. For example, a cell is addicted to an anti-apoptotic protein if the anti-apoptotic protein regulates apoptosis (i.e., programmed cell death) in the cell. In some instances, cells can be addicted to anti-apoptotic BCL-2 family member proteins for survival, and the BCL-2 family member proteins mitigate apoptosis in the cell. In some instances, a cell's addiction to a protein coincides with overexpression of the protein or predominant expression of the protein versus other related proteins in the cell. In some instances, a cell that is addicted to one or more BCL-2 family member proteins (e.g., BCL-2, BCL-$X_L$, MCL-1) has one or more of the proteins overexpressed and/or predominantly expressed in the cell.

BRIEF DESCRIPTION OF DRAWINGS

FIG. 3 shows the $EC_{50}$ of the indicated compounds in triggering apoptosis in MCL-1-addicted cancer cell lines including H23 and H82. These compounds do not induce apoptosis in cells deficient for the essential apoptotic effectors, Bax and Bak.

DETAILED DESCRIPTION OF CERTAIN EMBODIMENTS OF THE INVENTION

Figure 1A:
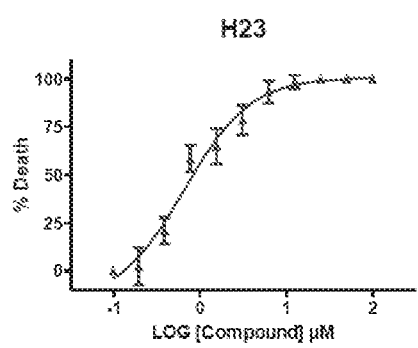
FIG. 1A shows Compound 1 ("Mclin") induces apoptosis with an EC50 of 0.6 µM in MCL-1-addicted cancer cell-line, H23.

The present invention provides compounds of Formulae (I), (II), (V), and (VI), which are phenylsulfonamido-benzofuran derivatives. The compounds are inhibitors of BCL-2 family member proteins. In certain embodiments, the compounds are selective inhibitors of the BCL-2 family member protein MCL-1. These compounds and other compounds described herein may be useful in the prevention and/or treatment of a proliferative disease. Also provided are methods of using compounds of Formula (I), (II), (III), (IV), (V), or (VI) to treat and/or prevent proliferative diseases. Exemplary proliferative diseases include, but are not limited to, cancers, benign neoplasms, diseases associated with angiogenesis, inflammatory diseases, autoinflammatory diseases, and autoimmune diseases.

Compounds

As generally described above, provided herein are compounds of Formula (I). The compounds are phenylsulfonamido-benzofuran derivatives. In certain embodiments, the present disclosure provides compounds of Formula (I):

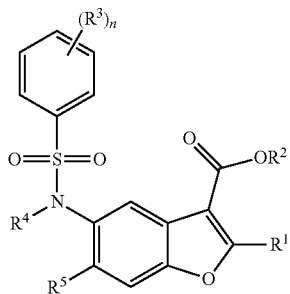

(I)

and pharmaceutically acceptable salts thereof,
wherein:

$R^1$ is hydrogen, halogen, or optionally substituted alkyl;

each instance of $R^3$ is independently halogen, —CN, —$NO_2$, —$N_3$, optionally substituted alkyl, —$OR^{3A}$, —$N(R^{3B})_2$, or optionally substituted acyl;

n is 0, 1, 2, 3, 4, or 5;

$R^4$ is hydrogen, optionally substituted alkyl, or a nitrogen protecting group;

$R^5$ is halogen or optionally substituted $C_{1-6}$ alkyl;

each of $R^2$ and $R^{3A}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and $R^{3B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{3B}$ are taken together with the intervening atoms to form optionally substituted heterocyclyl.

In certain embodiments, n is 1, and the compound of Formula (I) is of Formula (I-a):

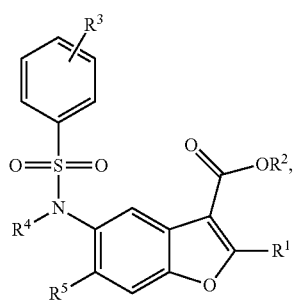

(I-a)

or a pharmaceutically acceptable salt thereof.

In certain embodiments, n is 1, and the compound of Formula (I) is of Formula (I-b):

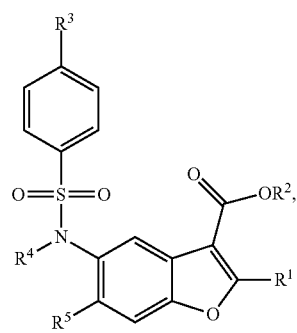

(I-b)

or a pharmaceutically acceptable salt thereof.

In certain embodiments, n is 1, and the compound of Formula (I) is of Formula (I-c):

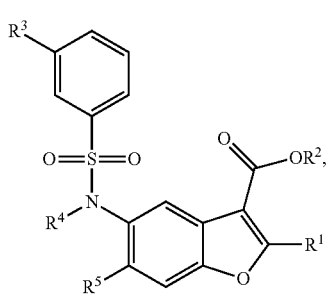

(I-c)

or a pharmaceutically acceptable salt thereof.

In certain embodiments, n is 1, and the compound of Formula (I) is of Formula (I-d):

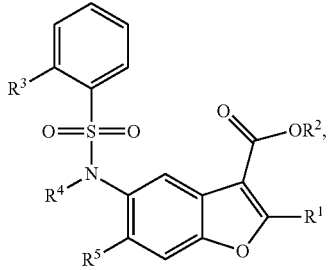

(I-d)

or a pharmaceutically acceptable salt thereof.

In certain embodiments, n is 2, and the compound of Formula (I) is of the formula:

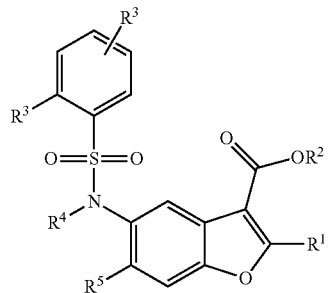

or a pharmaceutically acceptable salt thereof.

In certain embodiments, n is 2, and the compound of Formula (I) is of one of the following formulae:

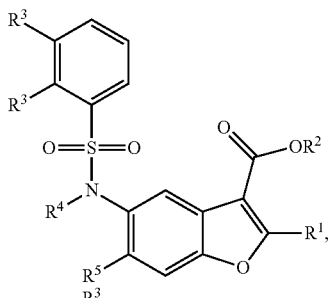

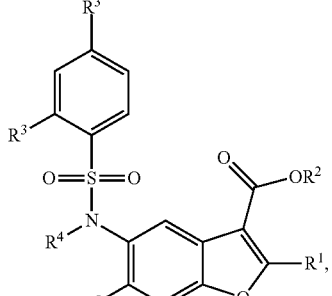

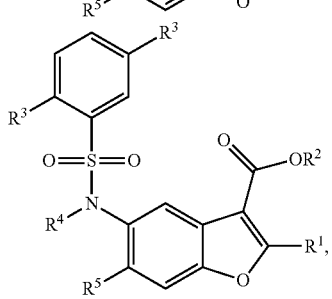

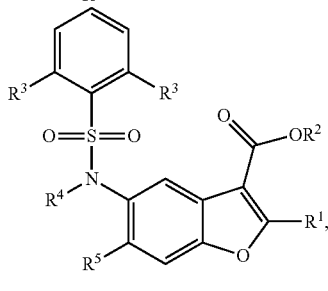

or a pharmaceutically acceptable salt thereof.

In certain embodiments, n is 2, and the compound of Formula (I) is of the formula:

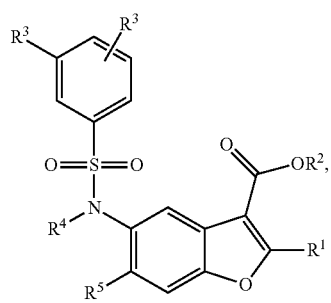

or a pharmaceutically acceptable salt thereof.

In certain embodiments, n is 2, and the compound of Formula (I) is of one of the following formulae:

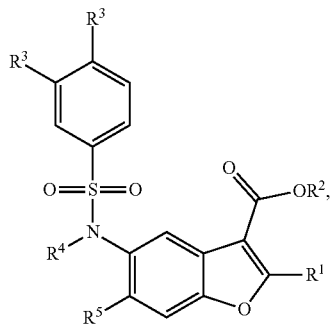

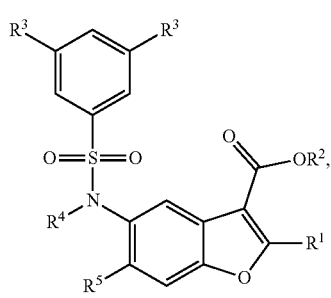

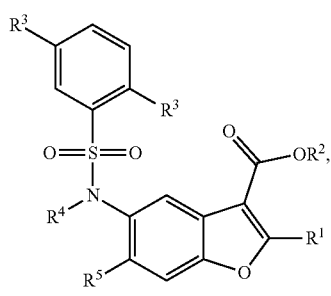

or a pharmaceutically acceptable salt thereof.

In certain embodiments, n is 2, and the compound of Formula (I) is of the formula:

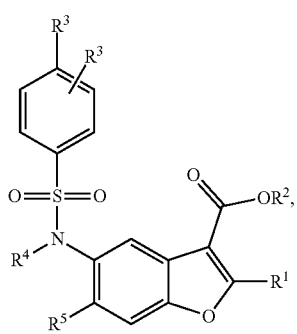

or a pharmaceutically acceptable salt thereof.

In certain embodiments, n is 2, and the compound of Formula (I) is of one of the following formulae:

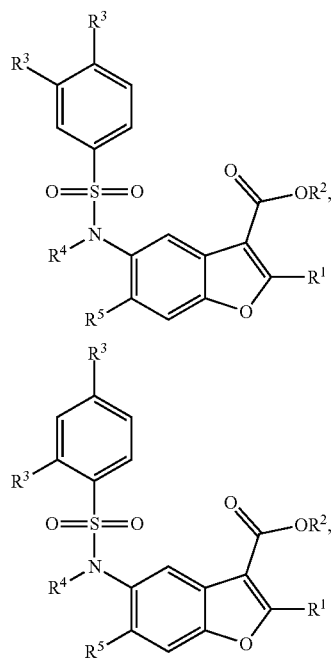

or a pharmaceutically acceptable salt thereof.

In certain embodiments, n is 3, and the compound of Formula (I) is of the formula:

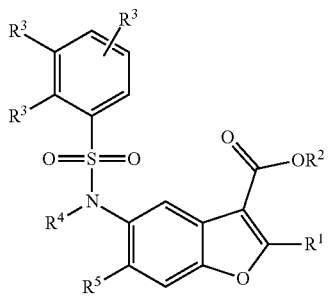

or a pharmaceutically acceptable salt thereof.

In certain embodiments, n is 3, and the compound of Formula (I) is of one of following formulae:

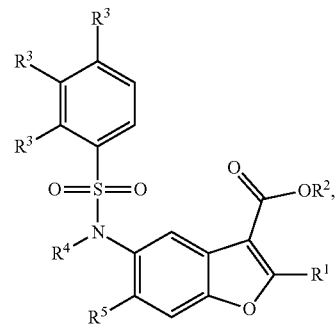

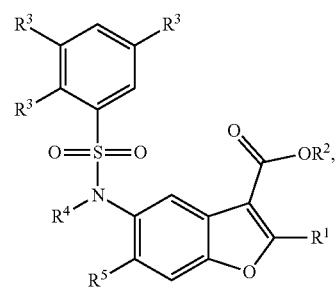

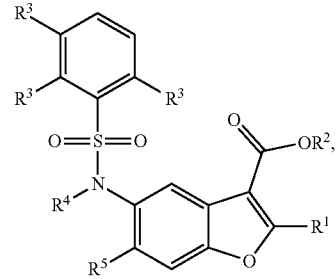

or a pharmaceutically acceptable salt thereof.

In certain embodiments, n is 3, and the compound of Formula (I) is of the formula:

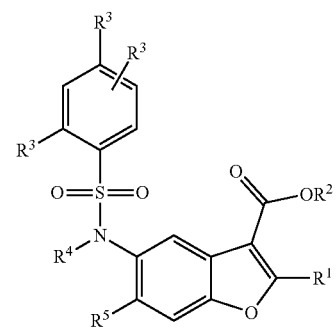

or a pharmaceutically acceptable salt thereof.

In certain embodiments, n is 3, and the compound of Formula (I) is of one of following formulae:

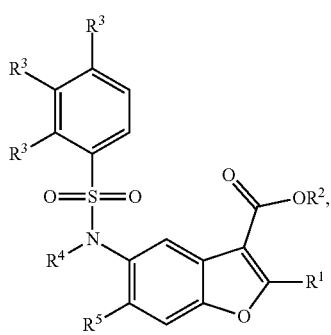

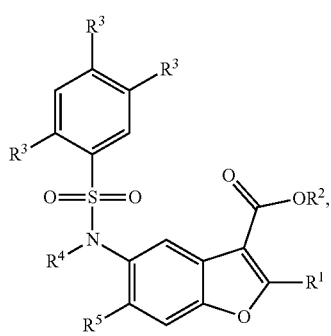

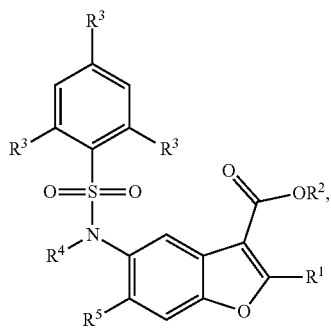

or a pharmaceutically acceptable salt thereof.

In certain embodiments, n is 3, and the compound of Formula (I) is of the formula:

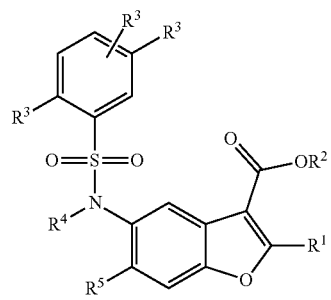

or a pharmaceutically acceptable salt thereof.

In certain embodiments, n is 3, and the compound of Formula (I) is of one of following formulae:

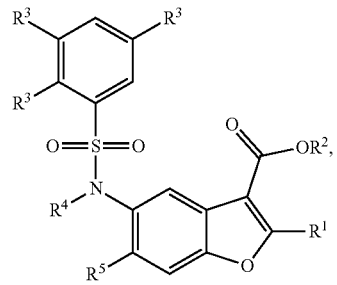

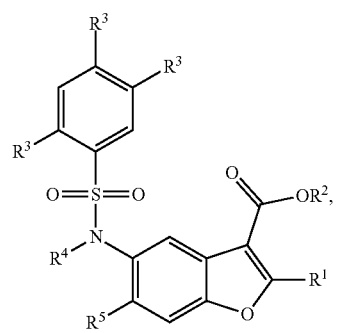

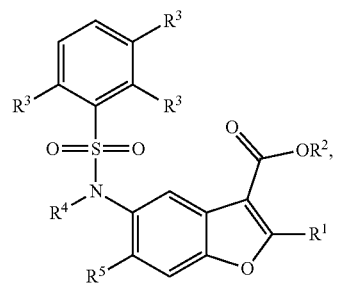

or a pharmaceutically acceptable salt thereof.

In certain embodiments, n is 3, and the compound of Formula (I) is of the formula:

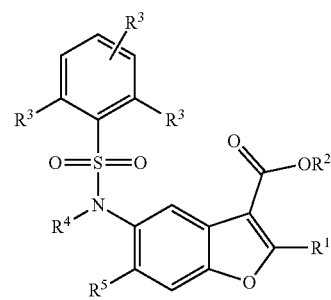

or a pharmaceutically acceptable salt thereof.

In certain embodiments, n is 3, and the compound of Formula (I) is of one of following formulae:

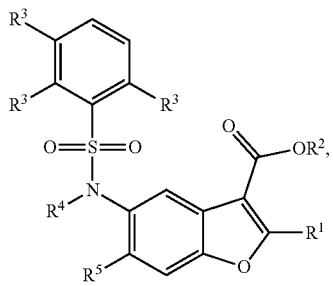

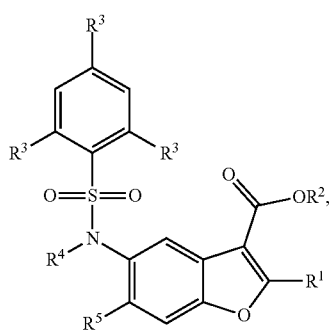

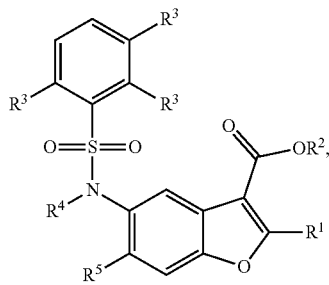

or a pharmaceutically acceptable salt thereof.

In certain embodiments, n is 3, and the compound of Formula (I) is of the formula:

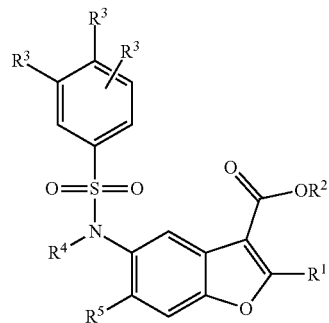

or a pharmaceutically acceptable salt thereof.

In certain embodiments, n is 3, and the compound of Formula (I) is of one of following formulae:

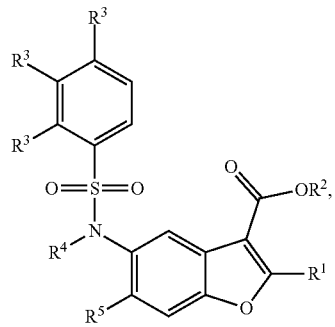

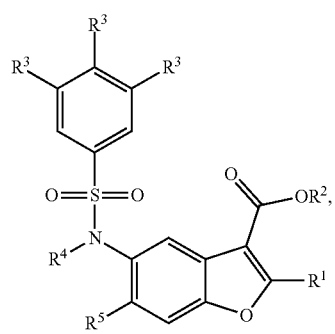

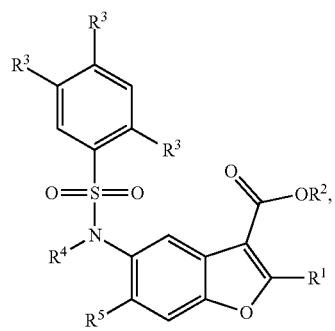

or a pharmaceutically acceptable salt thereof.

In certain embodiments, n is 3, and the compound of Formula (I) is of the formula:

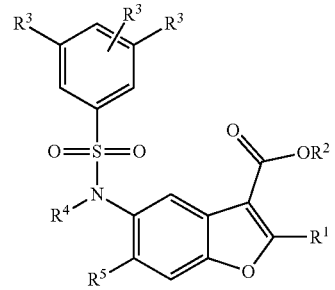

or a pharmaceutically acceptable salt thereof.

In certain embodiments, n is 3, and the compound of Formula (I) is of one of following formulae:

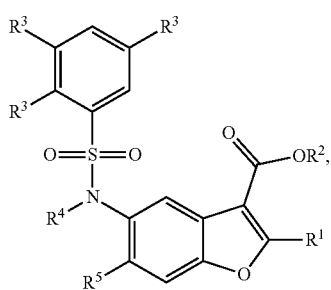

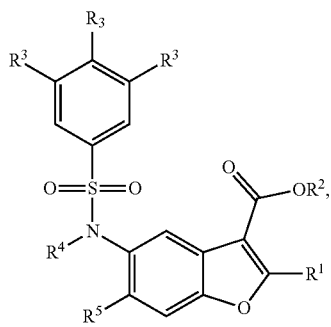

or a pharmaceutically acceptable salt thereof.

In certain embodiments, n is 3, and the compound of Formula (I) is of the formula:

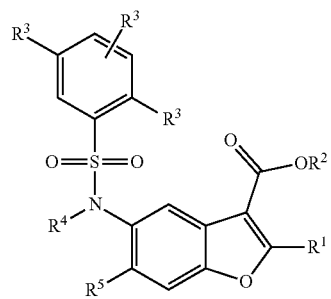

or a pharmaceutically acceptable salt thereof.

In certain embodiments, n is 3, and the compound of Formula (I) is of one of following formulae:

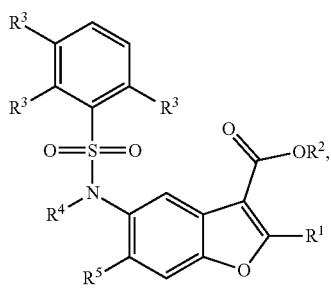

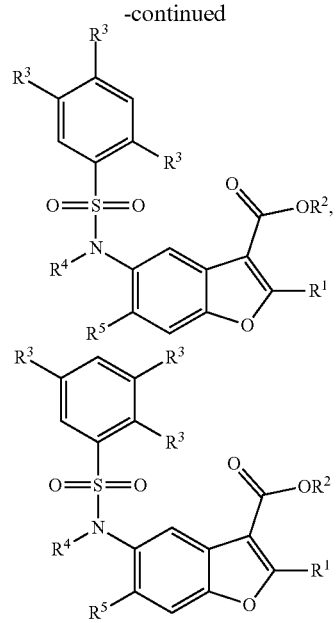

or a pharmaceutically acceptable salt thereof.

In certain embodiments, n is 4, and the compound of Formula (I) is of one of the following formulae:

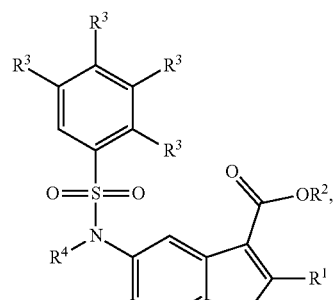

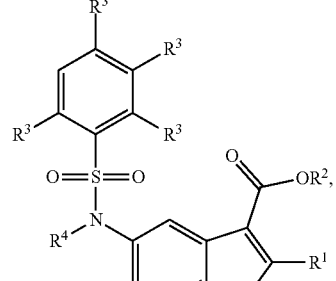

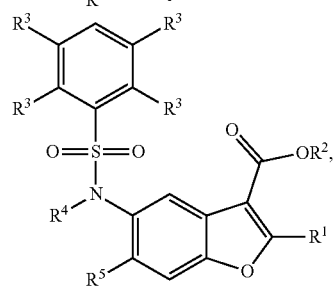

or a pharmaceutically acceptable salt thereof.

In certain embodiments, n is 5, and the compound of Formula (I) is of the following formula:

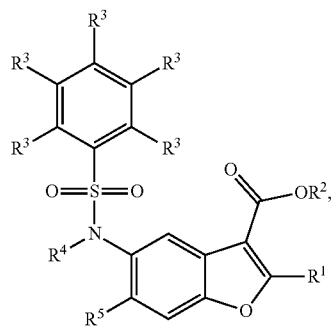

or a pharmaceutically acceptable salt thereof.

In certain embodiments, the compound of Formula (I) is of the formula:

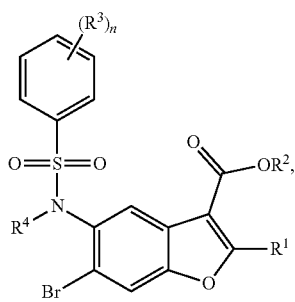

or a pharmaceutically acceptable salt thereof.

In certain embodiments, the compound of Formula (I) is of the formula:

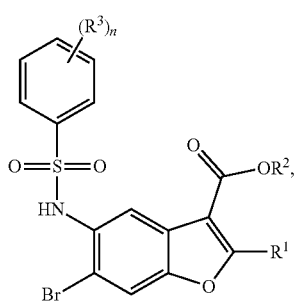

or a pharmaceutically acceptable salt thereof.

In certain embodiments, the compound of Formula (I) is of the formula:

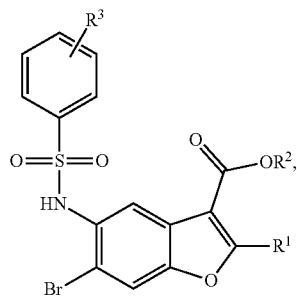

or a pharmaceutically acceptable salt thereof.

In certain embodiments, the compound of Formula (I) is of the formula:

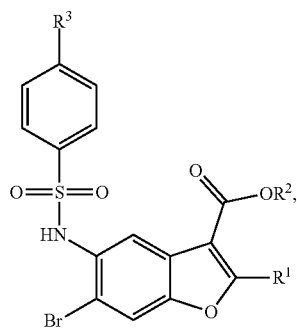

or a pharmaceutically acceptable salt thereof.

In certain embodiments, the compound of Formula (I) is of the formula:

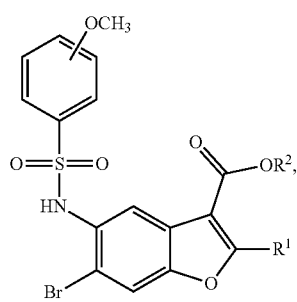

or a pharmaceutically acceptable salt thereof.

In certain embodiments, the compound of Formula (I) is of the formula:

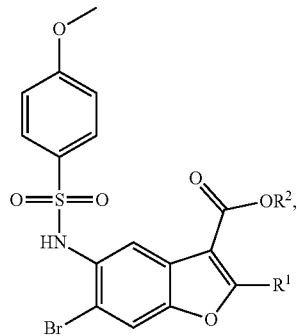

or a pharmaceutically acceptable salt thereof.

In certain embodiments, the compound of Formula (I) is of the formula:

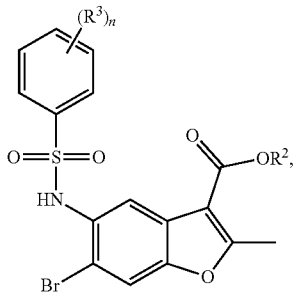

or a pharmaceutically acceptable salt thereof.

In certain embodiments, the compound of Formula (I) is of the formula:

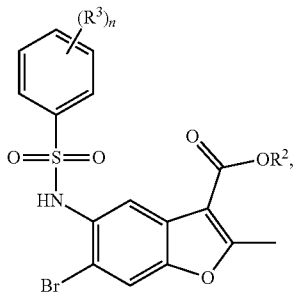

or a pharmaceutically acceptable salt thereof.

In certain embodiments, the compound of Formula (I) is of the formula:

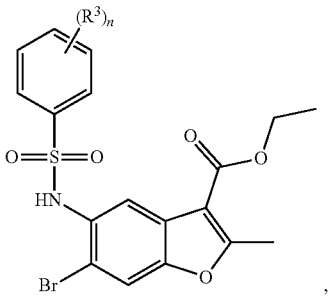

or a pharmaceutically acceptable salt thereof.

In certain embodiments, the compound of Formula (I) is of the formula:

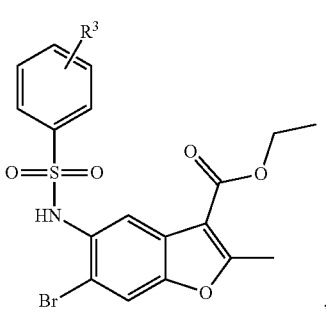

or a pharmaceutically acceptable salt thereof.

In certain embodiments, the compound of Formula (I) is of the formula:

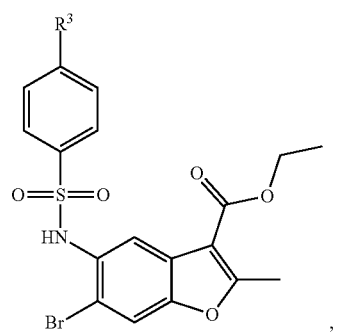

or a pharmaceutically acceptable salt thereof.

In certain embodiments, the compound of Formula (I) is of the formula:

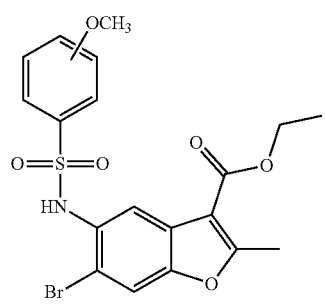

or a pharmaceutically acceptable salt thereof.

In certain embodiments, the compound of Formula (I) is of the formula:

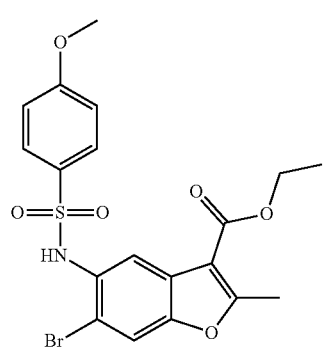

(Compound 1; "McLin")

or a pharmaceutically acceptable salt thereof.

In certain embodiments, n is 1 and $R^3$ is halogen. In certain embodiments, n is 1 and $R^3$ is F. In certain embodiments, n is 1 and $R^3$ is Cl. In certain embodiments, n is 1 and $R^3$ is Br. In certain embodiments, n is 1 and $R^3$ is I. In certain embodiments, n is 1 and $R^3$ is optionally substituted alkyl. In certain embodiments, n is 1 and $R^3$ is optionally substituted $C_{1-6}$ alkyl. In certain embodiments, n is 1 and $R^3$ is unsubstituted $C_{1-6}$ alkyl. In certain embodiments, n is 1 and $R^3$ is methyl, ethyl, n-propyl, or iso-propyl. In certain embodiments, n is 1 and $R^3$ is —$OR^{3A}$ and $R^{3A}$ is as defined herein. In certain embodiments, n is 1 and $R^3$ is —OH. In certain embodiments, n is 1; $R^3$ is —$OR^{3A}$; and $R^{3A}$ is optionally substituted alkyl. In certain embodiments, n is 1; $R^3$ is —$OR^{3A}$; and $R^{3A}$ is optionally substituted $C_{1-6}$ alkyl. In certain embodiments, n is 1; $R^3$ is —$OR^{3A}$; and $R^{3A}$ is unsubstituted $C_{1-6}$ alkyl. In certain embodiments, n is 1 and $R^3$ is —$OCH_3$. In certain embodiments, n is 1 and $R^3$ is —OEt. In certain embodiments, n is 1 and $R^3$ is —OPr. In certain embodiments, n is 1 and $R^3$ is —OPr or —OiPr. In certain embodiments, n is 1; $R^3$ is —$OR^{3A}$; and $R^{3A}$ is substituted $C_{1-6}$ alkyl. In certain embodiments, n is 1; $R^3$ is —$N(R^{3B})_2$; and each instance of $R^{3B}$ is as defined herein. In certain embodiments, n is 1; $R^3$ is —$N(R^{3B})_2$; and each instance of $R^{3B}$ is hydrogen, optionally substituted alkyl, or a nitrogen protecting group. In certain embodiments, n is 1; $R^3$ is —$NHR^{3B}$; and $R^{3B}$ is as defined herein. In certain embodiments, n is 1; $R^3$ is —$NHR^{3B}$; and $R^{3B}$ is hydrogen, optionally substituted alkyl, or a nitrogen protecting group. In certain embodiments, n is 1 and $R^3$ is —$NH_2$. In certain embodiments, n is 1; $R^3$ is —$N(CH_3)R^{3B}$; and $R^{3B}$ is as defined herein. In certain embodiments, n is 1; $R^3$ is —$N(CH_3)R^{3B}$; and $R^{3B}$ is hydrogen, optionally substituted alkyl, or a nitrogen protecting group. In certain embodiments, n is 1 and $R^3$ is —$N(CH_3)_2$.

In certain embodiments, n is 1; $R^3$ is halogen, —CN, —$NO_2$, —$N_3$, optionally substituted alkyl, —$OR^{3A}$, —$N(R^{3B})_2$, or optionally substituted acyl; and $R^5$ is independently halogen. In certain embodiments, n is 1; $R^3$ is halogen; and $R^5$ is independently halogen. In certain embodiments, n is 1; $R^3$ is optionally substituted alkyl; and $R^5$ is halogen. In certain embodiments, n is 1; $R^3$ is optionally substituted $C_{1-6}$ alkyl; and $R^5$ is halogen. In certain embodiments, n is 1; $R^3$ is substituted $C_{1-6}$ alkyl; and $R^5$ is halogen. In certain embodiments, n is 1; $R^3$ is unsubstituted $C_{1-6}$ alkyl; and $R^5$ is halogen. In certain embodiments, n is 1; $R^3$ is substituted $C_{1-6}$ alkyl; and $R^5$ is halogen. In certain embodiments, n is 1; $R^3$ is —$OR^{3A}$; and $R^5$ is halogen. In certain embodiments, n is 1; $R^3$ is —$OR^{3A}$; $R^5$ is halogen; and $R^{3A}$ is hydrogen or optionally substituted alkyl. In certain embodiments, n is 1; $R^3$ is —$OR^{3A}$; $R^5$ is halogen; and $R^{3A}$ is optionally substituted alkyl. In certain embodiments, n is 1; $R^3$ is —$OR^{3A}$; $R^5$ is halogen; and $R^{3A}$ is unsubstituted alkyl. In certain embodiments, n is 1; $R^3$ is —$OR^{3A}$; $R^5$ is halogen; and $R^{3A}$ is methyl or ethyl. In certain embodiments, n is 1; $R^3$ is —$OR^{3A}$; $R^5$ is halogen; and $R^{3A}$ is substituted alkyl. In certain embodiments, n is 1; $R^3$ is —$N(R^{3B})_2$; and $R^5$ is halogen. In certain embodiments, n is 1; $R^3$ is —$N(R^{3B})_2$; $R^5$ is halogen; and each instance of $R^{3B}$ is hydrogen, optionally substituted alkyl, or a nitrogen protecting group. In certain embodiments, n is 1; $R^3$ is —$NHR^{3B}$; $R^5$ is halogen; and $R^{3B}$ is hydrogen, optionally substituted alkyl, or a nitrogen protecting group. In certain embodiments, n is 1; $R^3$ is —$N(CH_3)R^{3B}$; $R^5$ is halogen; and $R^{3B}$ is hydrogen, optionally substituted alkyl, or a nitrogen protecting group.

In certain embodiments, $R^1$ is optionally substituted $C_{1-6}$ alkyl; n is 1; $R^3$ is halogen, —CN, —$NO_2$, —$N_3$, optionally substituted alkyl, —$OR^{3A}$, —$N(R^{3B})_2$, or optionally substituted acyl; and $R^5$ is independently halogen. In certain embodiments, $R^1$ is unsubstituted $C_{1-6}$ alkyl; n is 1; $R^3$ is halogen, —CN, —$NO_2$, —$N_3$, optionally substituted alkyl, —$OR^{3A}$, —$N(R^{3B})_2$, or optionally substituted acyl; and $R^5$ is independently halogen. In certain embodiments, $R^1$ is substituted $C_{1-6}$ alkyl; n is 1; $R^3$ is halogen, —CN, —$NO_2$, —$N_3$, optionally substituted alkyl, —$OR^{3A}$, —$N(R^{3B})_2$, or optionally substituted acyl; and $R^5$ is independently halogen. In certain embodiments, $R^1$ is optionally substituted $C_{1-6}$ alkyl; n is 1; $R^3$ is halogen, optionally substituted alkyl, or —$OR^{3A}$; and $R^5$ is independently halogen. In certain embodiments, $R^1$ is unsubstituted $C_{1-6}$ alkyl; n is 1; $R^3$ is halogen, optionally substituted alkyl, or —$OR^{3A}$; and $R^5$ is independently halogen. In certain embodiments, $R^1$ is substituted $C_{1-6}$ alkyl; n is 1; $R^3$ is halogen, optionally substituted alkyl, —$OR^{3A}$, or optionally substituted acyl; and $R^5$ is independently halogen.

In certain embodiments, $R^1$ is optionally substituted $C_{1-6}$ alkyl; $R^2$ is independently optionally substituted $C_{1-6}$ alkyl; n is 1; $R^3$ is halogen, —CN, —$NO_2$, —$N_3$, optionally substituted alkyl, —$OR^{3A}$, —$N(R^{3B})_2$, or optionally substituted acyl; and $R^5$ is independently halogen. In certain embodiments, $R^1$ is unsubstituted $C_{1-6}$ alkyl; $R^2$ is independently unsubstituted $C_{1-6}$ alkyl; n is 1; $R^3$ is halogen, —CN, —$NO_2$, —$N_3$, optionally substituted alkyl, —$OR^{3A}$, —$N(R^{3B})_2$, or optionally substituted acyl; and $R^5$ is independently halogen. In certain embodiments, $R^1$ is substituted $C_{1-6}$ alkyl; $R^2$ is independently substituted $C_{1-6}$ alkyl; n is 1; $R^3$ is halogen, —CN, —$NO_2$, —$N_3$, optionally substituted alkyl, —$OR^{3A}$, —$N(R^{3B})_2$, or optionally substituted acyl; and $R^5$ is independently halogen. In certain embodiments, $R^1$ is substituted $C_{1-6}$ alkyl; $R^2$ is independently unsubstituted $C_{1-6}$ alkyl; n is 1; $R^3$ is halogen, —CN, —$NO_2$, —$N_3$, optionally substituted alkyl, —$OR^{3A}$, —$N(R^{3B})_2$, or optionally substituted acyl; and $R^5$ is independently halogen.

As generally described above, provided herein are compounds of Formula (II). The compounds are phenylsulfonamido-benzofuran derivatives. In certain embodiments, the present disclosure provides compounds of Formula (II):

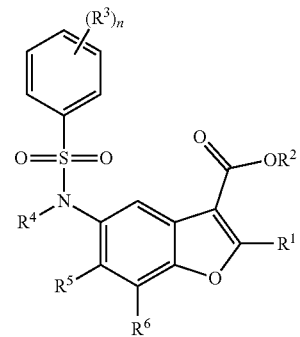

(II)

and pharmaceutically acceptable salts thereof,
wherein:
$R^1$ is hydrogen, halogen, or optionally substituted alkyl;
each instance of $R^3$ is independently halogen, —CN, —$NO_2$, —$N_3$, optionally substituted alkyl, —$OR^{3A}$, —$N(R^{3B})_2$, or optionally substituted acyl;
n is 0, 1, 2, 3, 4, or 5;
$R^4$ is hydrogen, optionally substituted alkyl, or a nitrogen protecting group;
$R^5$ is halogen or optionally substituted $C_{1-6}$ alkyl;
each of $R^2$ and $R^{3A}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and
$R^{3B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{3B}$ are taken together with the intervening atoms to form optionally substituted heterocyclyl.

$R^6$ is halogen, —CN, —NO$_2$, —N$_3$, optionally substituted alkyl, —OR$^{6A}$, —N(R$^{6B}$)$_2$, or optionally substituted acyl;

$R^{6A}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and each instance of $R^{6B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{6B}$ are taken together with the intervening atoms to form optionally substituted heterocyclyl.

In certain embodiments, n is 1, and the compound of Formula (II) is of Formula (II-a):

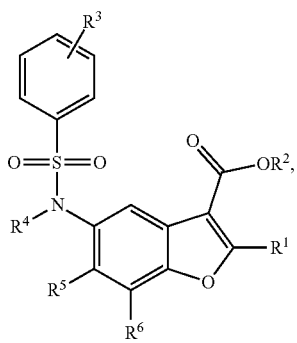

(II-a)

or a pharmaceutically acceptable salt thereof.

In certain embodiments, n is 1, and the compound of Formula (II) is of Formula (II-b):

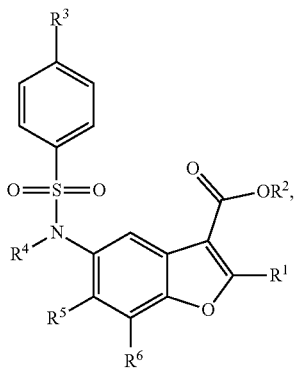

(II-b)

or a pharmaceutically acceptable salt thereof.

In certain embodiments, n is 1, and the compound of Formula (II) is of Formula (II-c):

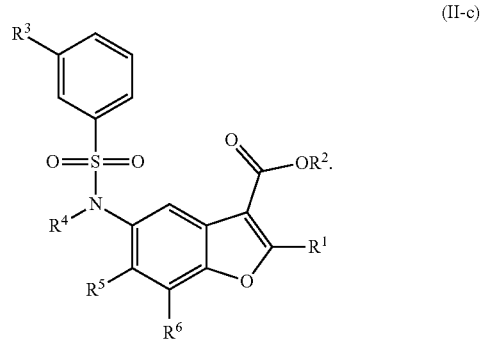

(II-c)

or a pharmaceutically acceptable salt thereof.

In certain embodiments, n is 1, and the compound of Formula (II) is of Formula (II-d):

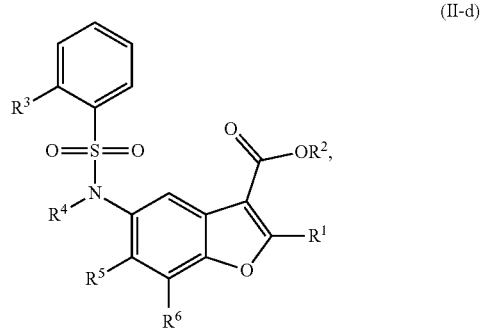

(II-d)

or a pharmaceutically acceptable salt thereof.

In certain embodiments, n is 2, and the compound of Formula (II) is of the formula:

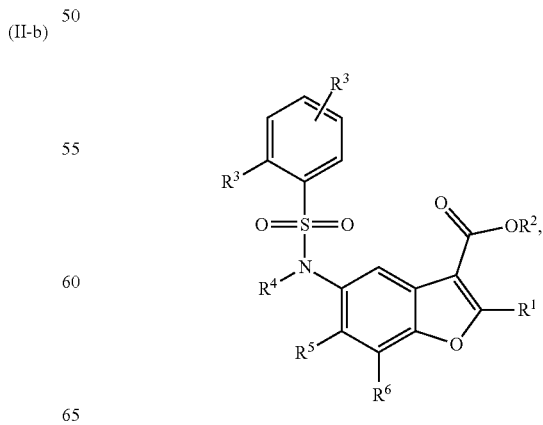

or a pharmaceutically acceptable salt thereof.

In certain embodiments, n is 2, and the compound of Formula (II) is of one of the following formulae:
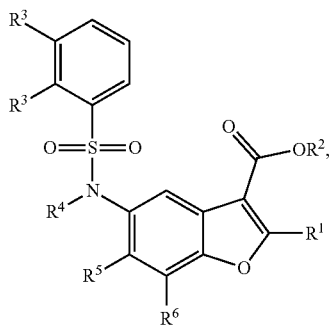
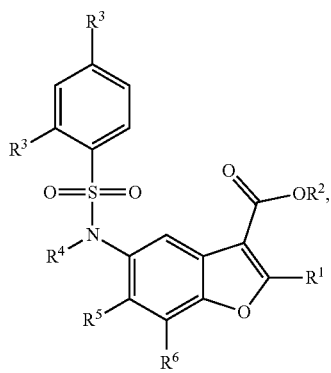
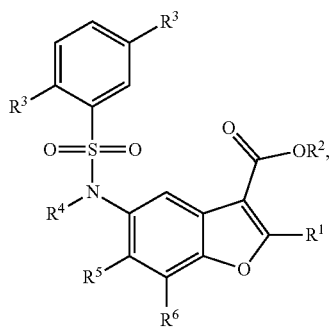
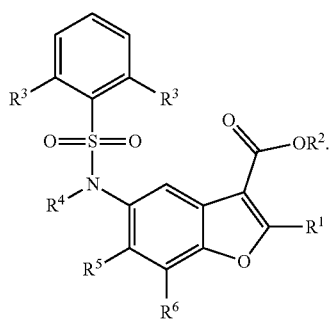
In certain embodiments, n is 2, and the compound of Formula (II) is of the formula:
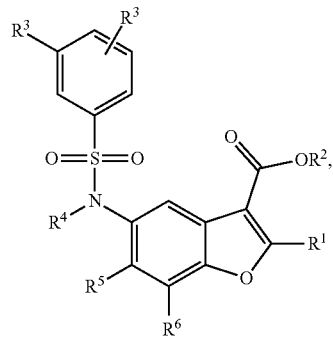
or a pharmaceutically acceptable salt thereof.
In certain embodiments, n is 2, and the compound of Formula (II) is of one of the following formulae:
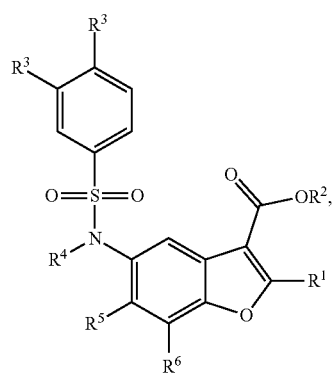
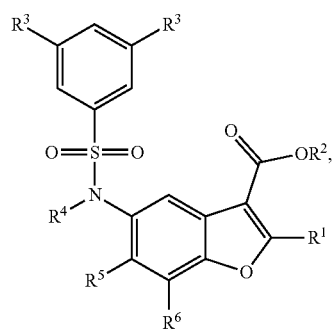
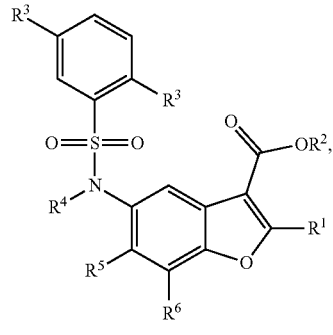
or a pharmaceutically acceptable salt thereof.

In certain embodiments, n is 2, and the compound of Formula (II) is of the formula:

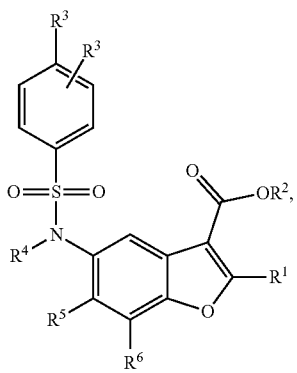

or a pharmaceutically acceptable salt thereof.

In certain embodiments, n is 2, and the compound of Formula (II) is of one of the following formulae:

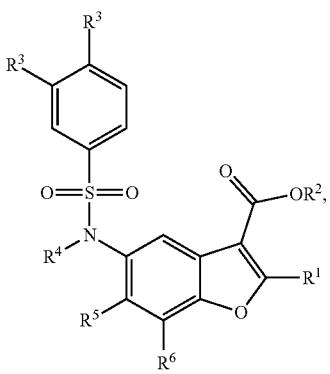

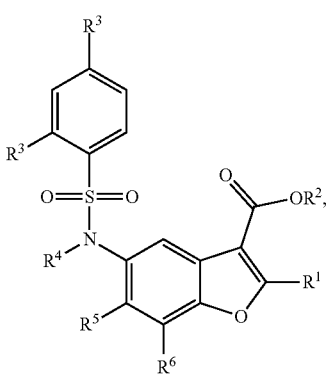

or a pharmaceutically acceptable salt thereof.

In certain embodiments, n is 3, and the compound of Formula (II) is of the formula:

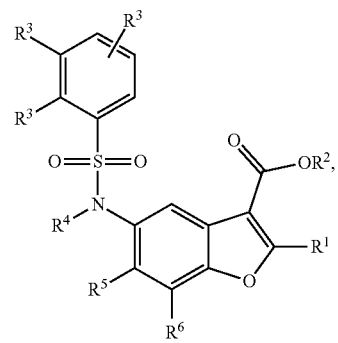

or a pharmaceutically acceptable salt thereof.

In certain embodiments, n is 3, and the compound of Formula (II) is of one of following formulae:

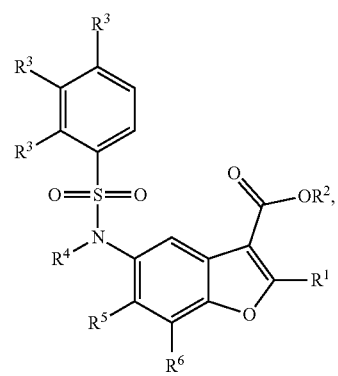

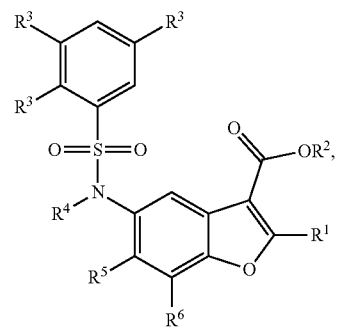

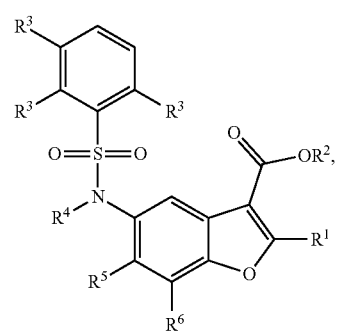

or a pharmaceutically acceptable salt thereof.

In certain embodiments, n is 3, and the compound of Formula (II) is of the formula:

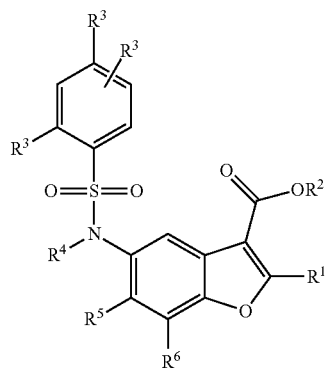

or a pharmaceutically acceptable salt thereof.

In certain embodiments, n is 3, and the compound of Formula (II) is of one of following formulae:

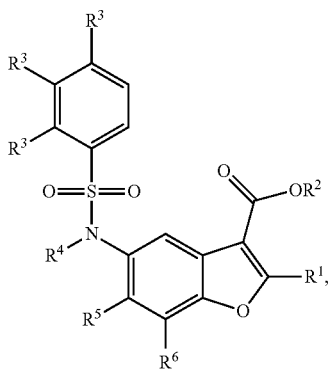

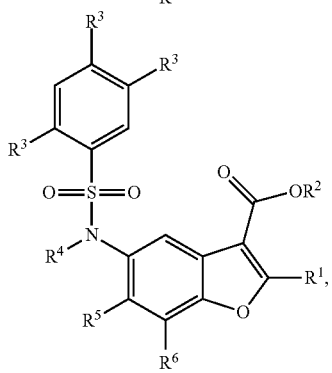

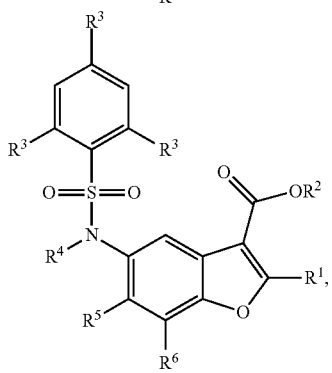

or a pharmaceutically acceptable salt thereof.

In certain embodiments, n is 3, and the compound of Formula (II) is of the formula:

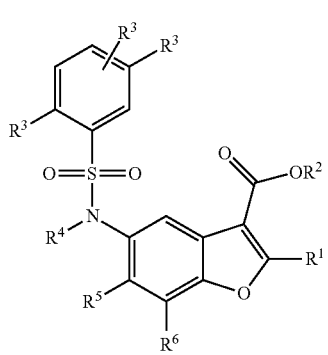

or a pharmaceutically acceptable salt thereof.

In certain embodiments, n is 3, and the compound of Formula (II) is of one of following formulae:

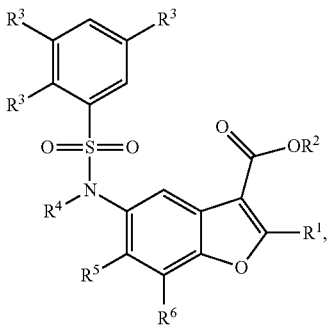

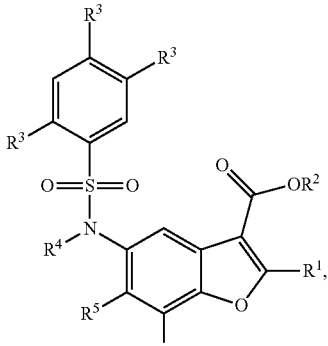

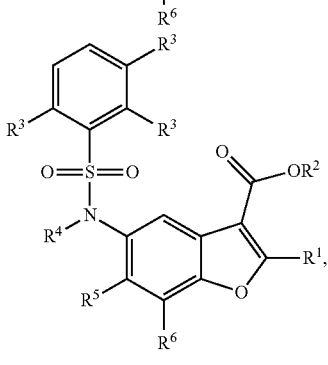

or a pharmaceutically acceptable salt thereof.

In certain embodiments, n is 3, and the compound of Formula (II) is of the formula:

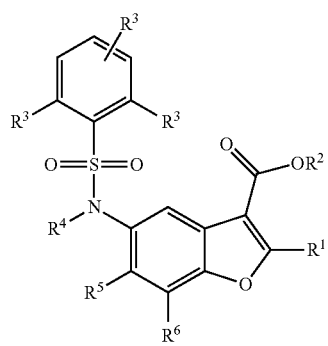

or a pharmaceutically acceptable salt thereof.

In certain embodiments, n is 3, and the compound of Formula (II) is of one of following formulae:

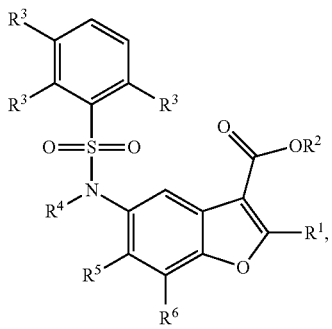

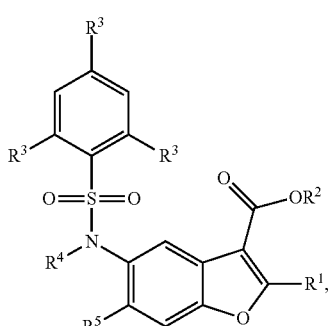

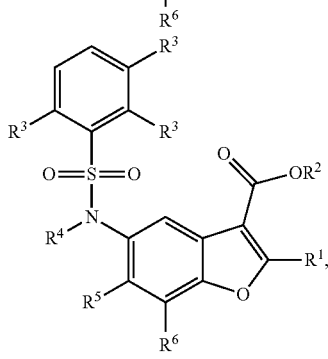

or a pharmaceutically acceptable salt thereof.

In certain embodiments, n is 3, and the compound of Formula (II) is of the formula:

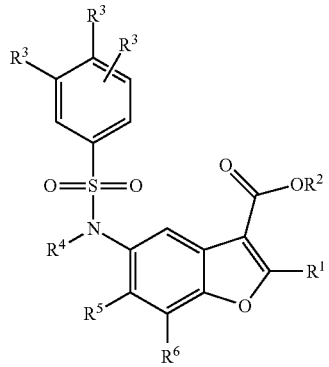

or a pharmaceutically acceptable salt thereof.

In certain embodiments, n is 3, and the compound of Formula (II) is of one of following formulae:

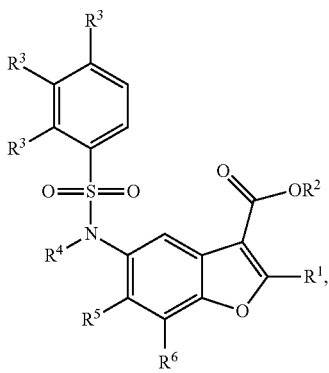

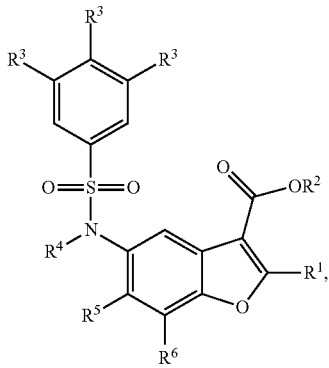

or a pharmaceutically acceptable salt thereof.

In certain embodiments, n is 3, and the compound of Formula (II) is of the formula:

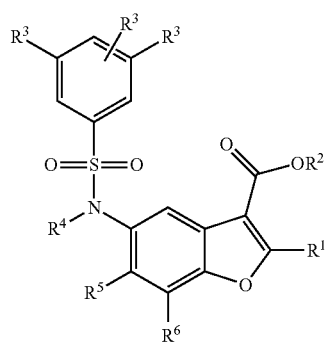

or a pharmaceutically acceptable salt thereof.

In certain embodiments, n is 3, and the compound of Formula (II) is of one of following formulae:

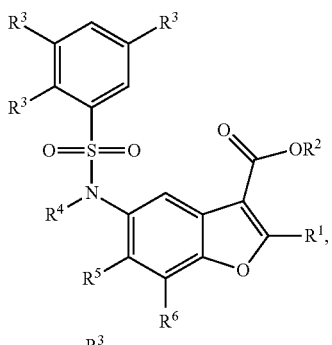

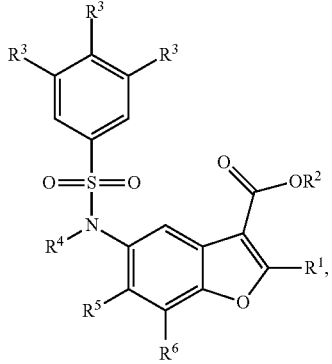

or a pharmaceutically acceptable salt thereof.

In certain embodiments, n is 3, and the compound of Formula (II) is of the formula:

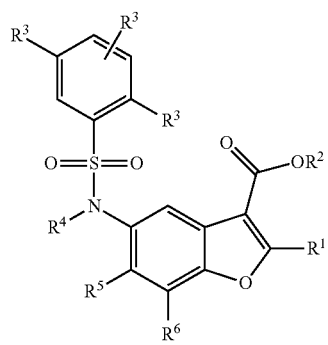

or a pharmaceutically acceptable salt thereof.

In certain embodiments, n is 3, and the compound of Formula (II) is of one of following formulae:

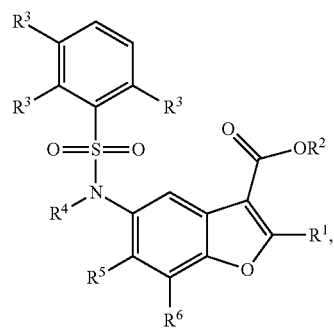

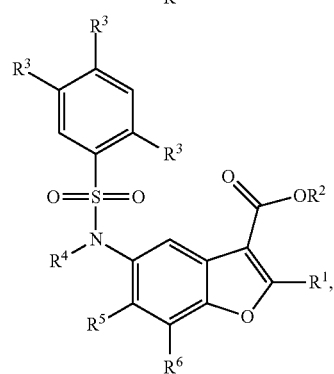

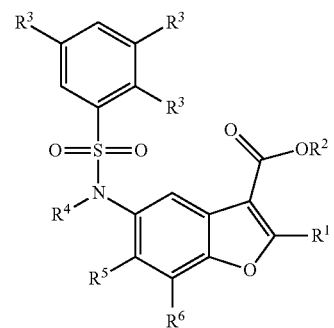

or a pharmaceutically acceptable salt thereof.

In certain embodiments, n is 4, and the compound of Formula (II) is of one of the following formulae:

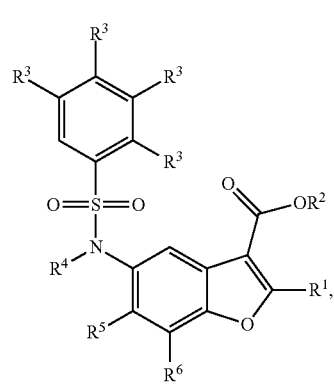

-continued

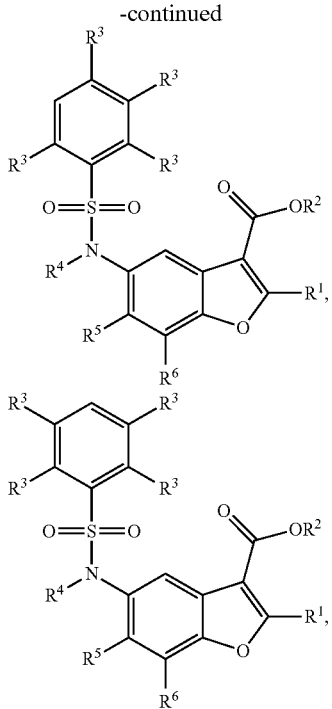

or a pharmaceutically acceptable salt thereof.

In certain embodiments, n is 5, and the compound of Formula (II) is of the following formula:

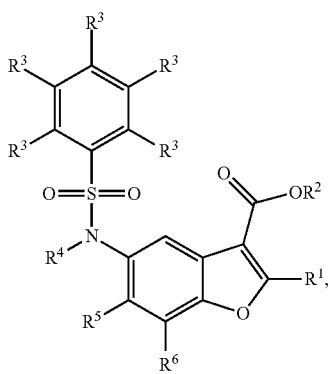

or a pharmaceutically acceptable salt thereof.

In another aspect, the present invention provides compounds of Formula (V):

(V)

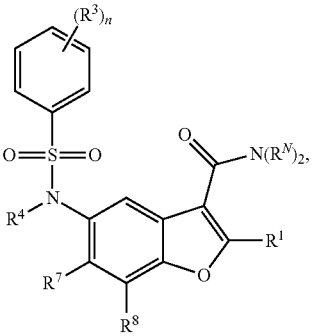

and pharmaceutically acceptable salts thereof, wherein:

$R^1$ is hydrogen, halogen, or optionally substituted alkyl;
each instance of $R^3$ is independently halogen, —CN, —$NO_2$, —$N_3$, optionally substituted alkyl, —$OR^{3A}$, —$N(R^{3B})_2$, or optionally substituted acyl;

$R^{3A}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and $R^{3B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{3B}$ are taken together with the intervening atoms to form optionally substituted heterocyclyl.

n is 0, 1, 2, 3, 4, or 5;

$R^4$ is hydrogen, optionally substituted alkyl, or a nitrogen protecting group;

$R^7$ is hydrogen, halogen, —CN, —$NO_2$, —$N_3$, optionally substituted alkyl, —$OR^{7A}$, —$N(R^{7B})_2$, or optionally substituted acyl;

$R^{7A}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and $R^{7B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{7B}$ are taken together with the intervening atoms form optionally substituted heterocyclyl.

$R^8$ is hydrogen, halogen, —CN, —$NO_2$, —$N_3$, optionally substituted alkyl, —$OR^{8A}$, —$N(R^{8B})_2$, or optionally substituted acyl;

$R^{8A}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of $R^{8B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{8B}$ are taken together with the intervening atoms to form optionally substituted heterocyclyl; and each instance of $R^N$ is independently hydrogen, optionally substituted alkyl, —$OR^{NA}$, —$N(R^{NB})_2$, or a nitrogen protecting group, or two $R^N$ are taken together with the intervening atoms form optionally substituted heterocyclyl;

$R^{NA}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and each instance of $R^{NB}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{NB}$ are taken together with the intervening atoms to form optionally substituted heterocyclyl;

provided that at least one instance of $R^N$ is not hydrogen, —OH, or —$NH_2$.

In certain embodiments, the compound of Formula (V) is not one of the following:
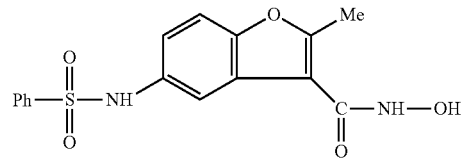
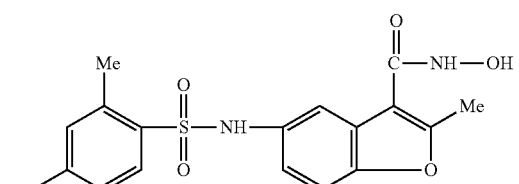
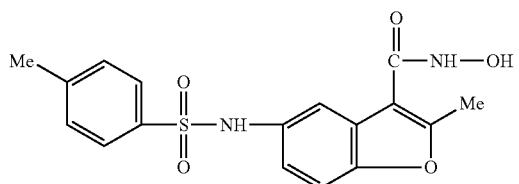
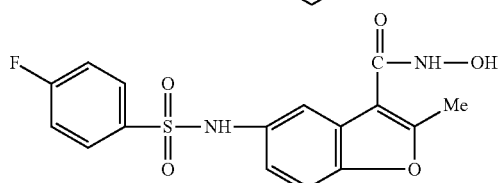
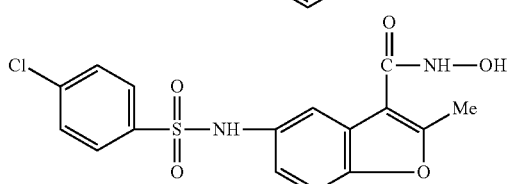
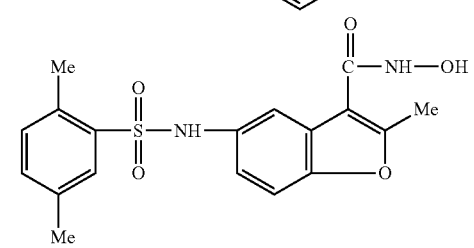
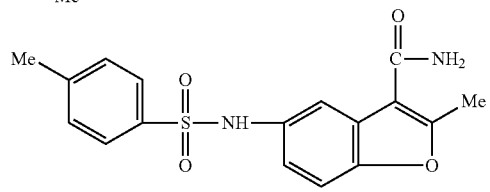
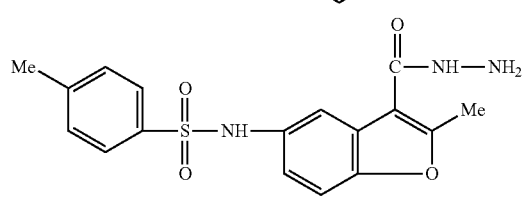
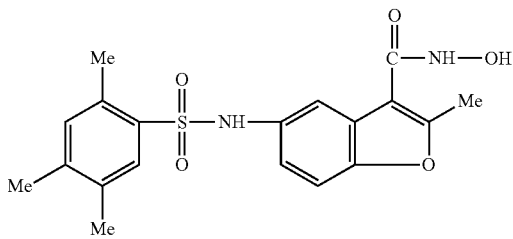
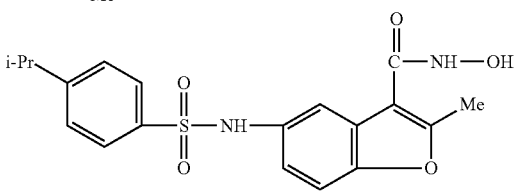
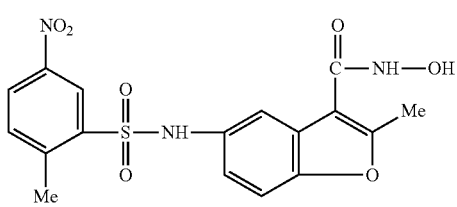
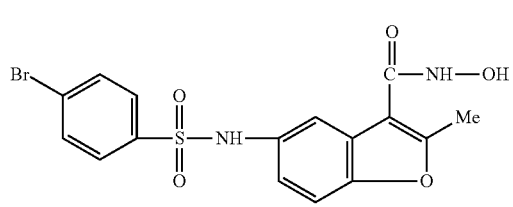
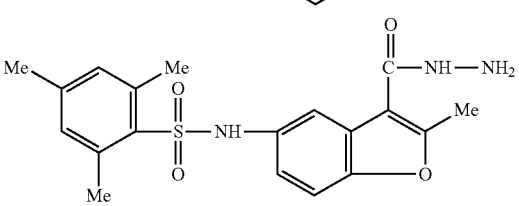
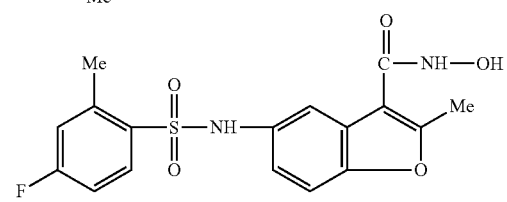
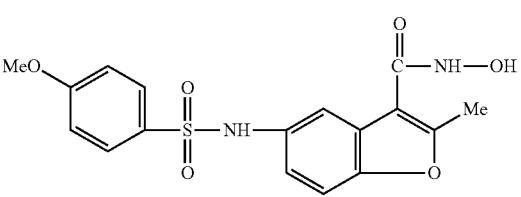
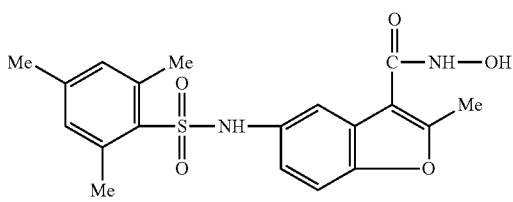

-continued

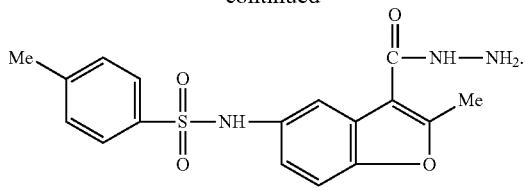

In certain embodiments, n is 1, and the compound of Formula (V) is of Formula (V-a):

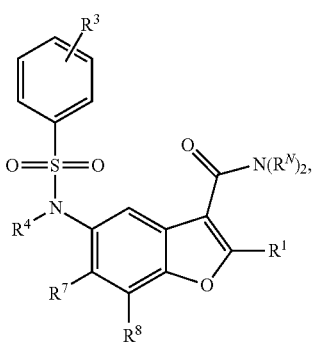

(V-a)

or a pharmaceutically acceptable salt thereof.

In certain embodiments, n is 1, and the compound of Formula (V) is of one of the following formulae:

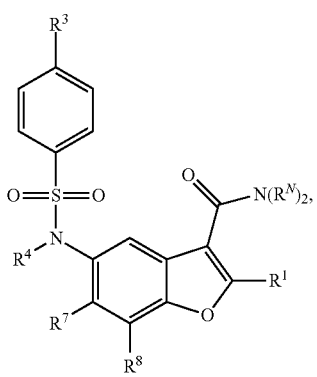

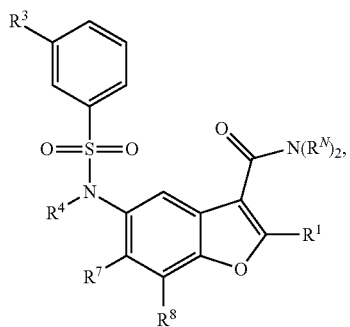

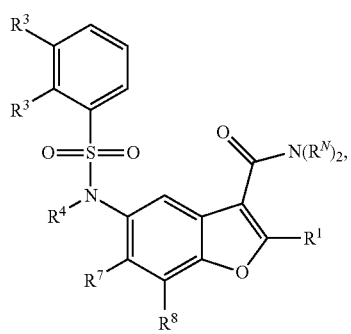

or a pharmaceutically acceptable salt thereof.

In certain embodiments, n is 2, and the compound of Formula (V) is of one of the following formulae:

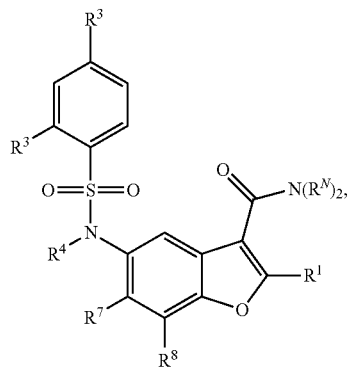

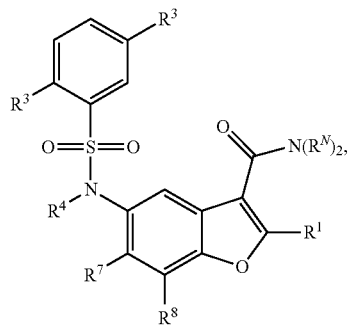

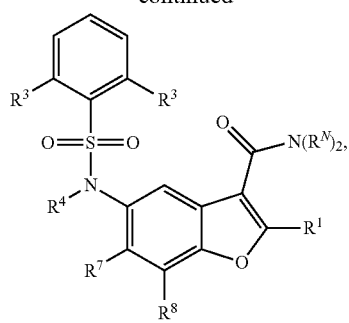
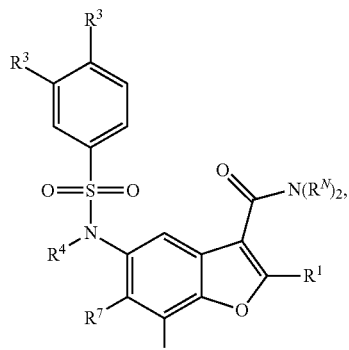
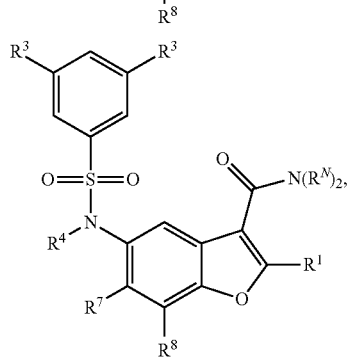
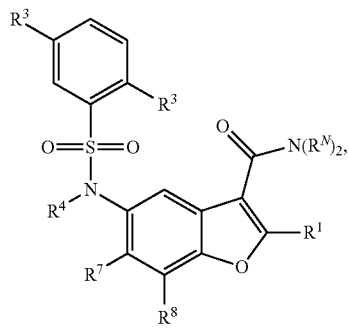
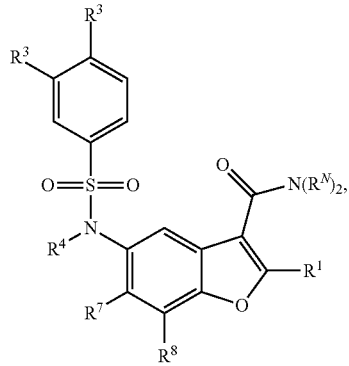
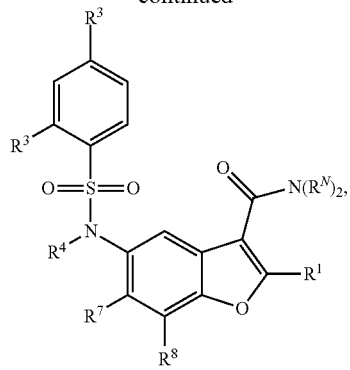
or a pharmaceutically acceptable salt thereof.
In certain embodiments, n is 3, and the compound of Formula (V) is of one of the following formulae:
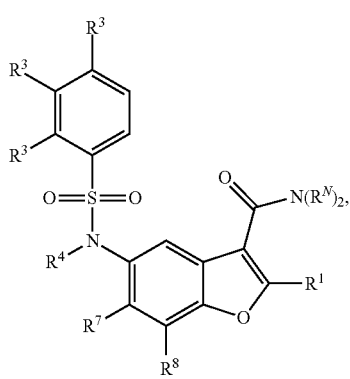
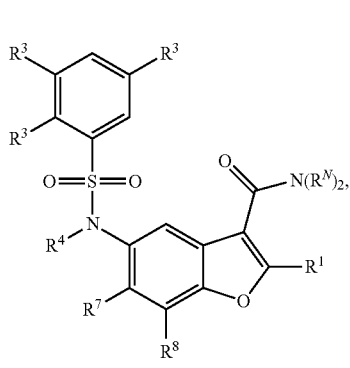
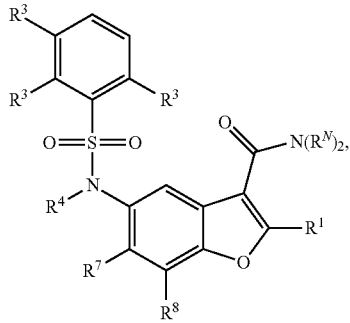

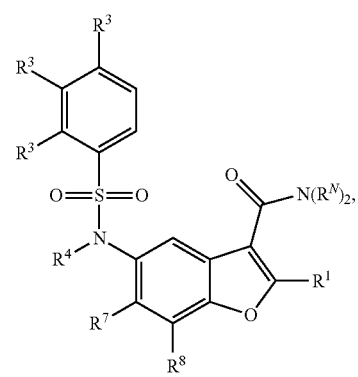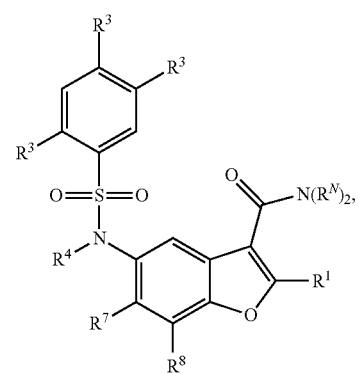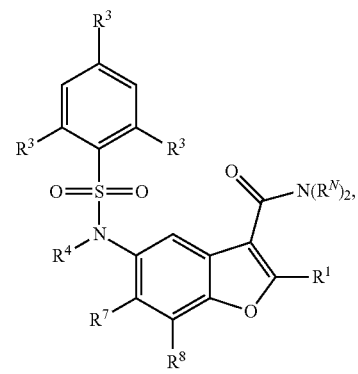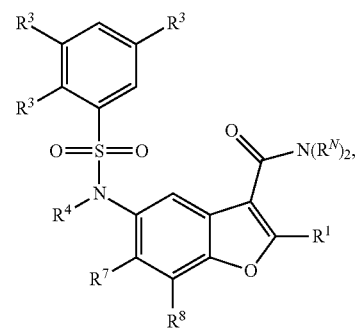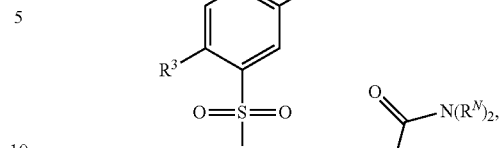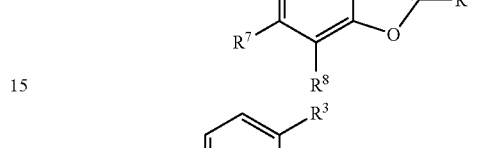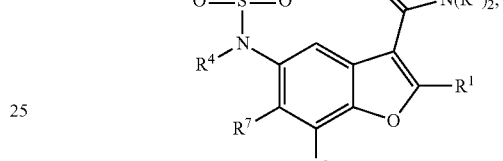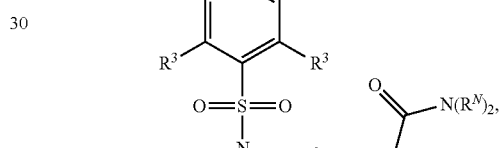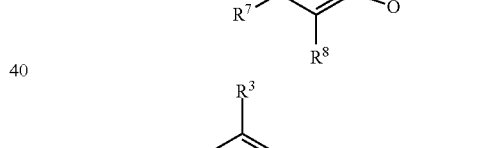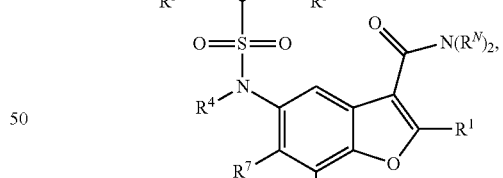

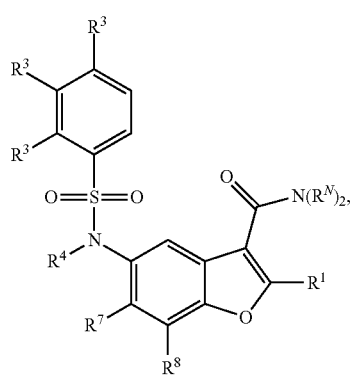
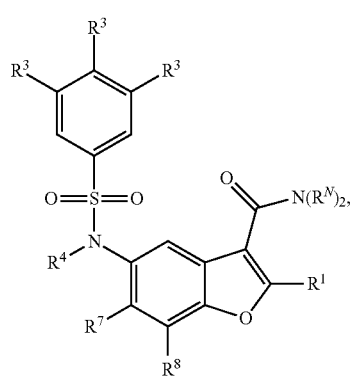
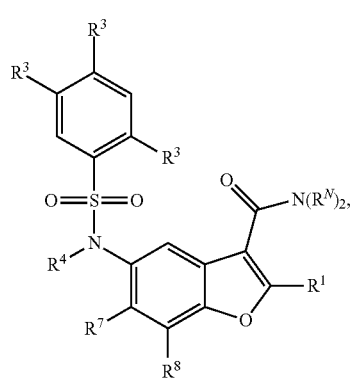
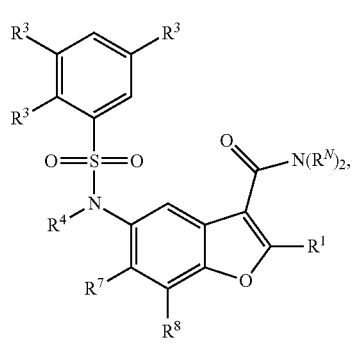
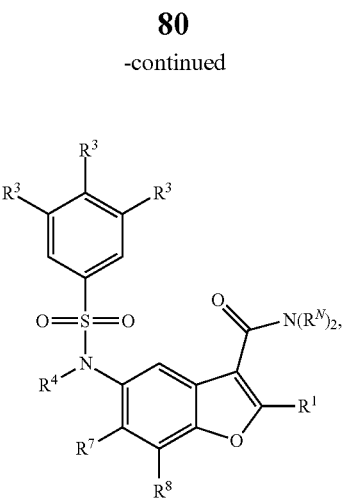
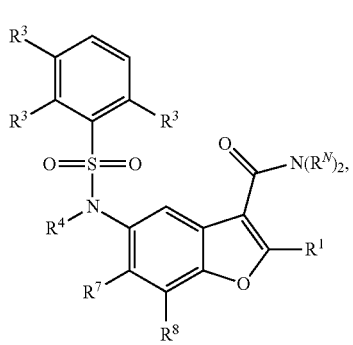
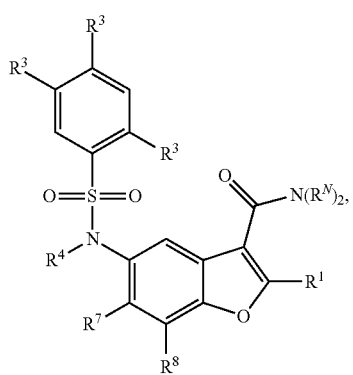
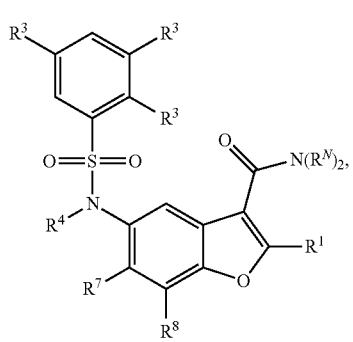
or a pharmaceutically acceptable salt thereof.
In certain embodiments, n is 4, and the compound of Formula (V) is of one of the following formulae:

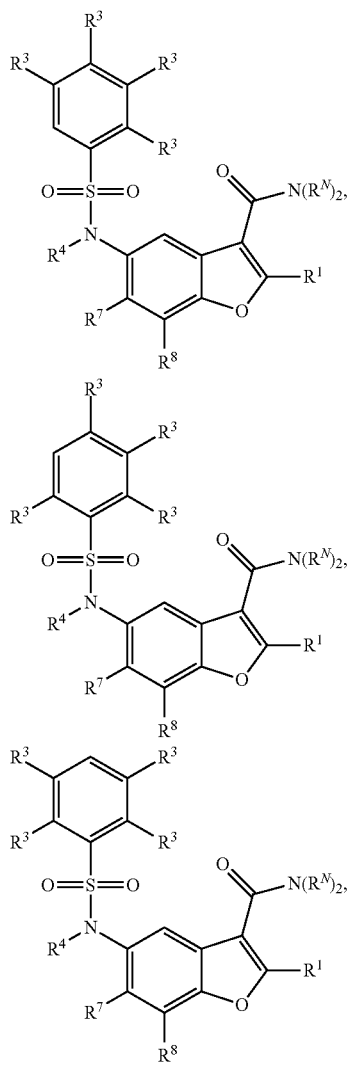

or a pharmaceutically acceptable salt thereof.

In certain embodiments, n is 5, and the compound of Formula (V) is of the following formula:

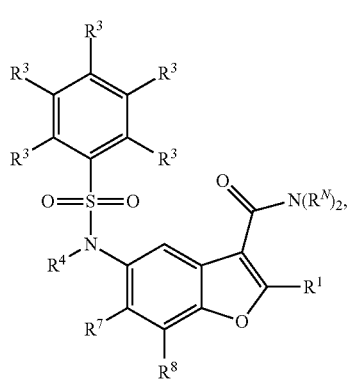

or a pharmaceutically acceptable salt thereof.

In certain embodiments, a compound of Formula (V) is of one of the following formulae:

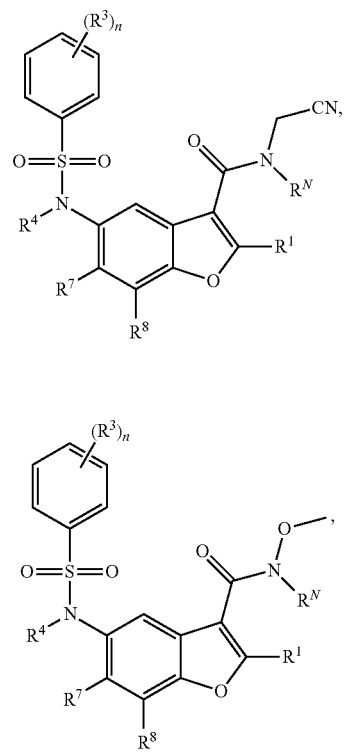

or a pharmaceutically acceptable salt thereof.

In certain embodiments, a compound of Formula (V) is of one of the following formulae:

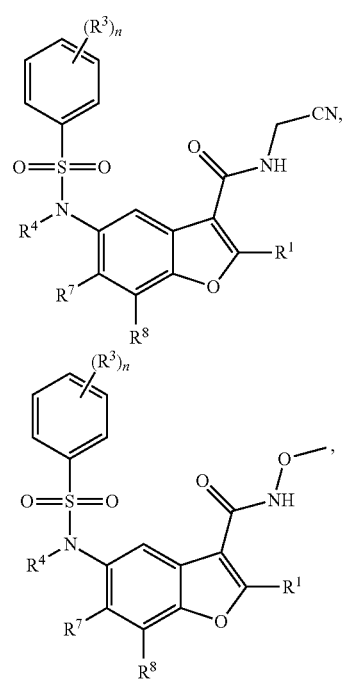

or a pharmaceutically acceptable salt thereof.

In certain embodiments, a compound of Formula (V) is of the following formula:

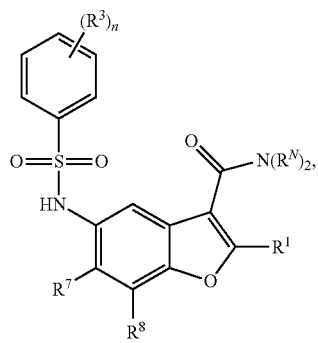

or a pharmaceutically acceptable salt thereof.

In certain embodiments, a compound of Formula (V) is of the following formula:

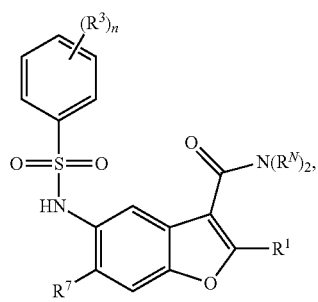

or a pharmaceutically acceptable salt thereof.

In certain embodiments, a compound of Formula (V) is of the following formula:

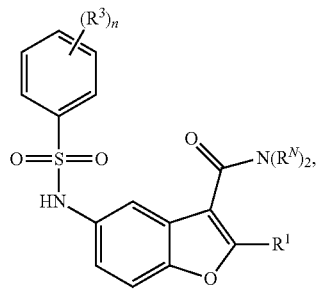

or a pharmaceutically acceptable salt thereof.

In certain embodiments, a compound of Formula (V) is of the following formula:

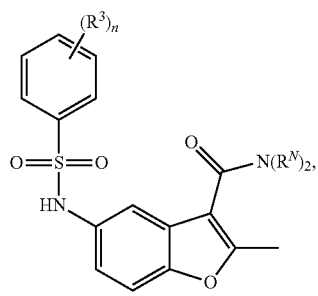

or a pharmaceutically acceptable salt thereof.

In certain embodiments, a compound of Formula (V) is of one of the following formulae:

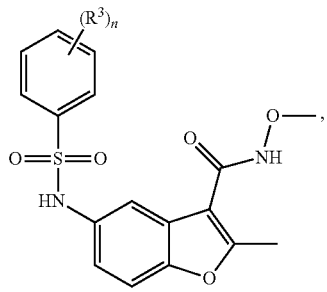

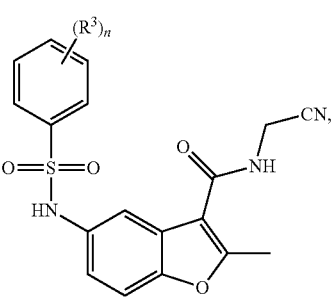

or a pharmaceutically acceptable salt thereof.

In certain embodiments, a compound of Formula (V) is of one of the following formulae:

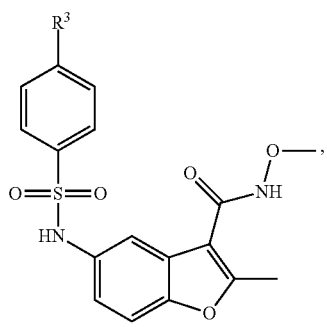

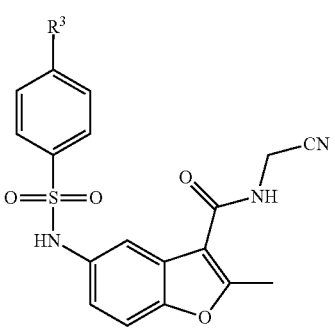

or a pharmaceutically acceptable salt thereof.

In certain embodiments, a compound of Formula (V) is of one of the following formulae:

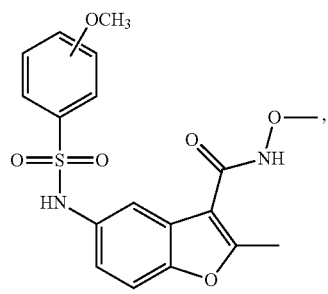

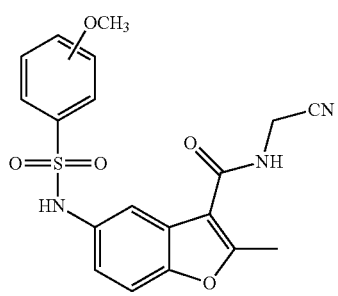

or a pharmaceutically acceptable salt thereof.

In certain embodiments, a compound of Formula (V) is of one of the following formulae:

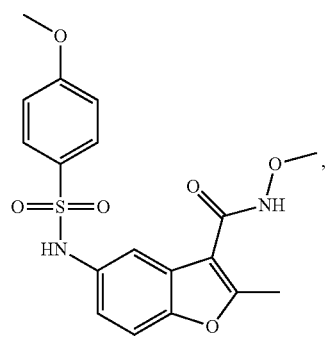

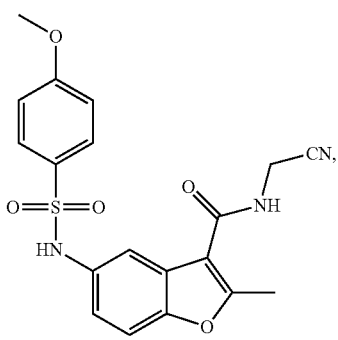

or a pharmaceutically acceptable salt thereof.

In another aspect, the present invention provides compounds of Formula (VI):

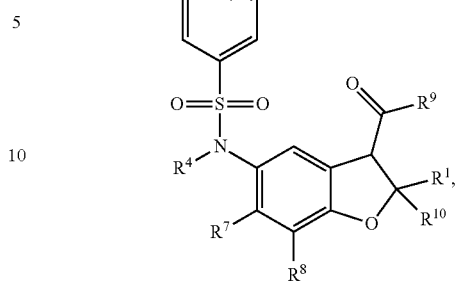

and pharmaceutically acceptable salts thereof, wherein:

$R^1$ is hydrogen, halogen, or optionally substituted alkyl;

each instance of $R^3$ is independently halogen, —CN, —NO$_2$, —N$_3$, optionally substituted alkyl, —OR$^{3A}$, —N(R$^{3B}$)$_2$, or optionally substituted acyl;

$R^{3A}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and $R^{3B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{3B}$ are taken together with the intervening atoms to form optionally substituted heterocyclyl.

n is 0, 1, 2, 3, 4, or 5;

$R^4$ is hydrogen, optionally substituted alkyl, or a nitrogen protecting group;

$R^7$ is hydrogen, halogen, —CN, —NO$_2$, —N$_3$, optionally substituted alkyl, —OR$^{7A}$, —N(R$^{7B}$)$_2$, or optionally substituted acyl;

$R^{7A}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and $R^{7B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{7B}$ are taken together with the intervening atoms form optionally substituted heterocyclyl.

$R^8$ is hydrogen, halogen, —CN, —NO$_2$, —N$_3$, optionally substituted alkyl, —OR$^{8A}$, —N(R$^{8B}$)$_2$, or optionally substituted acyl;

$R^{8A}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of $R^{8B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{8B}$ are taken together with the intervening atoms to form optionally substituted heterocyclyl; and $R^9$ is hydrogen, optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted acyl, —$OR^2$, or —$N(R^{9B})_2$;

$R^2$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of $R^{9B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{9B}$ are taken together with the intervening atoms to form optionally substituted heterocyclyl;

$R^{10}$ is optionally substituted alkyl or —$OR^{10A}$; and $R^{10A}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group.

In certain embodiments, n is 1, and the compound of Formula (VI) is of Formula (VI-a):

(VI-a)

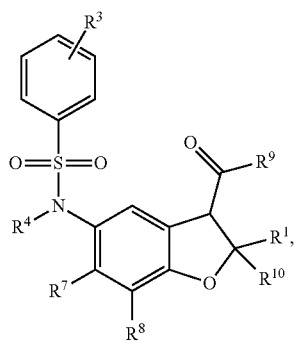

or a pharmaceutically acceptable salt thereof.

In certain embodiments, n is 1, and the compound of Formula (VI) is of one of the following formulae:
or a pharmaceutically acceptable salt thereof.

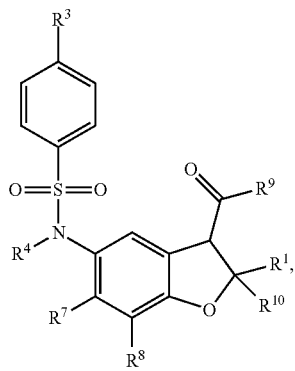

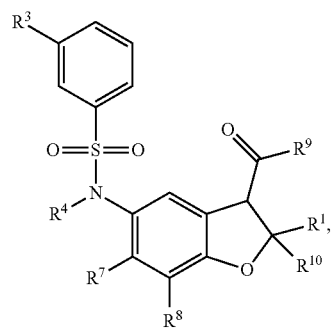

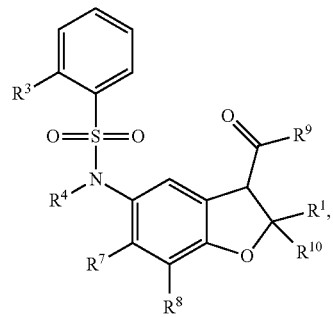

In certain embodiments, n is 2, and the compound of Formula (VI) is of one of the following formulae:

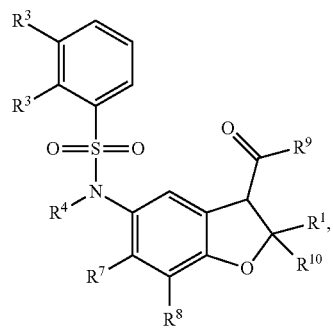

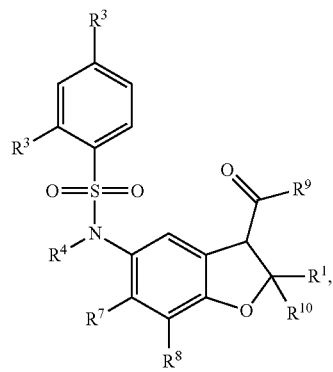

-continued
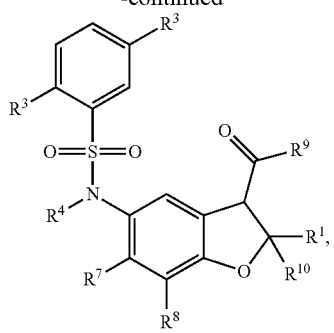
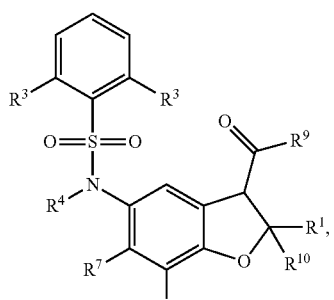
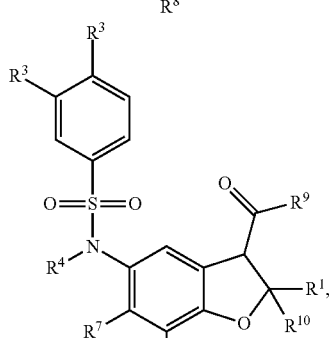
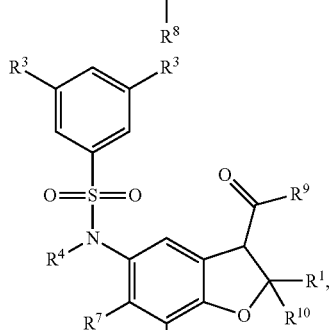
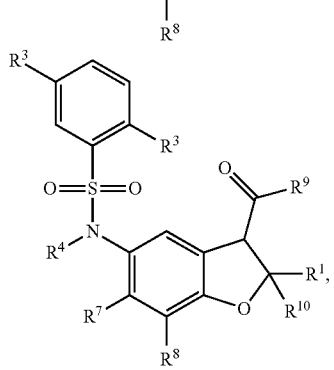
-continued
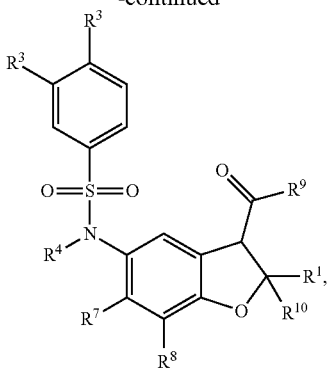
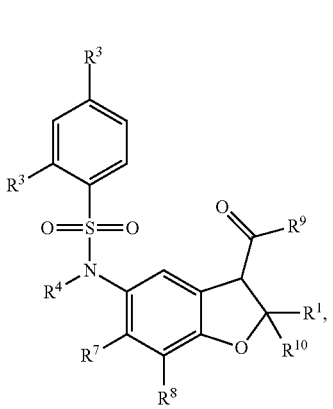
or a pharmaceutically acceptable salt thereof.
In certain embodiments, n is 3, and the compound of Formula (VI) is of one of the following formulae:
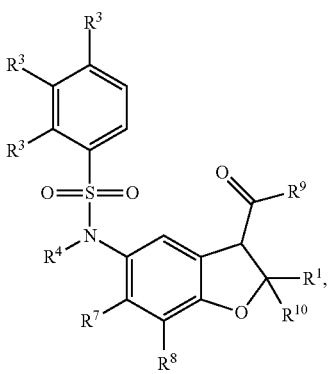
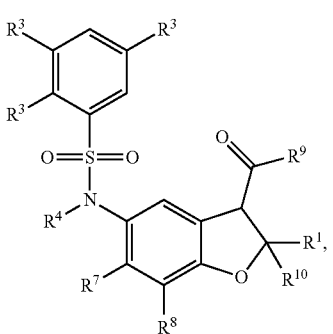

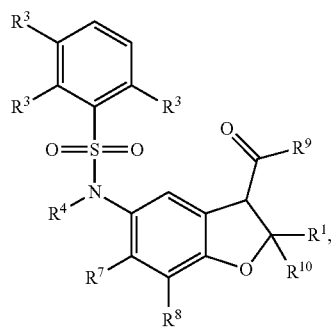
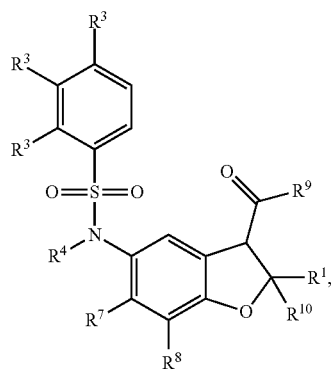
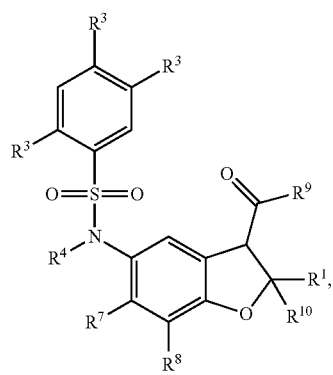
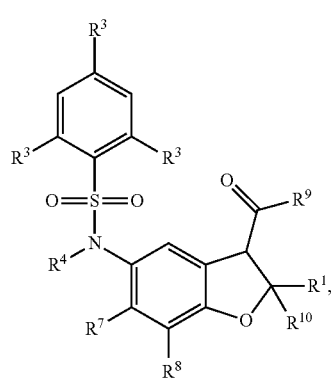
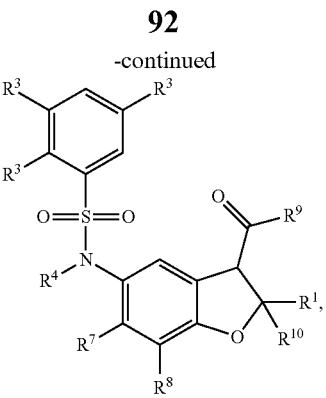
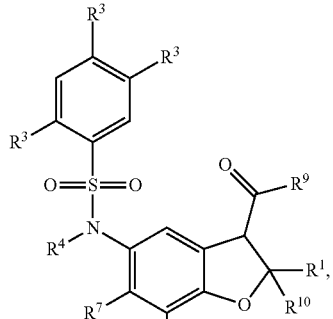
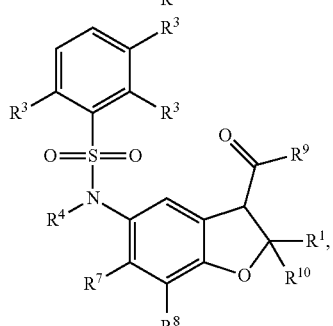
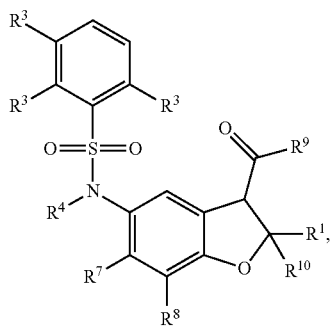
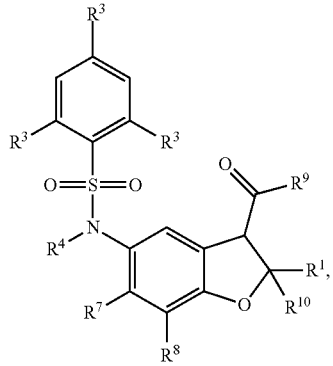

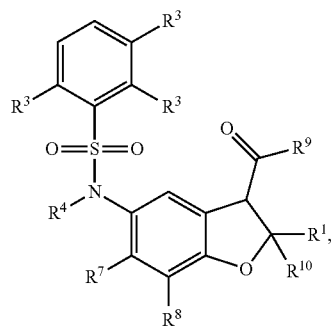
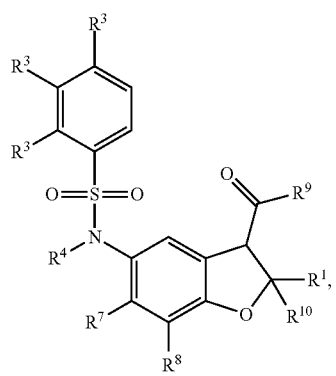
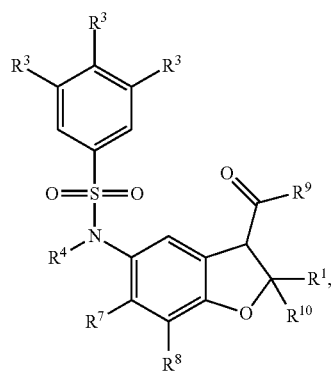
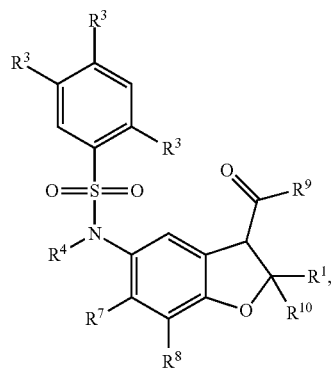
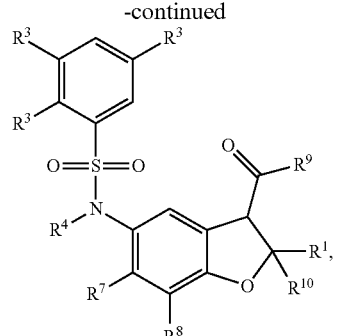
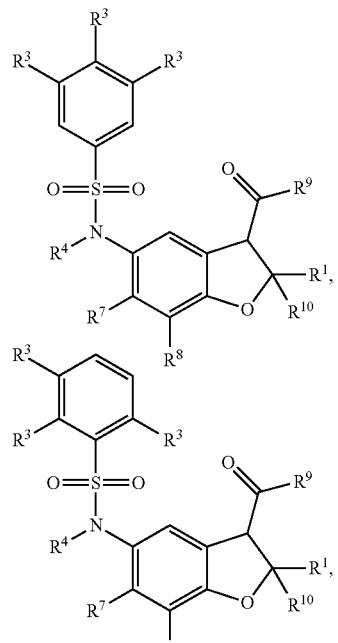
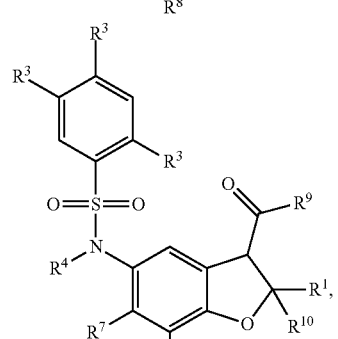
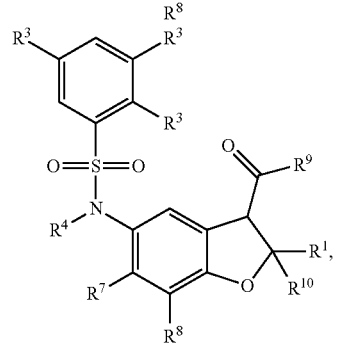
or a pharmaceutically acceptable salt thereof.

In certain embodiments, n is 4, and the compound of Formula (VI) is of one of the following formulae:

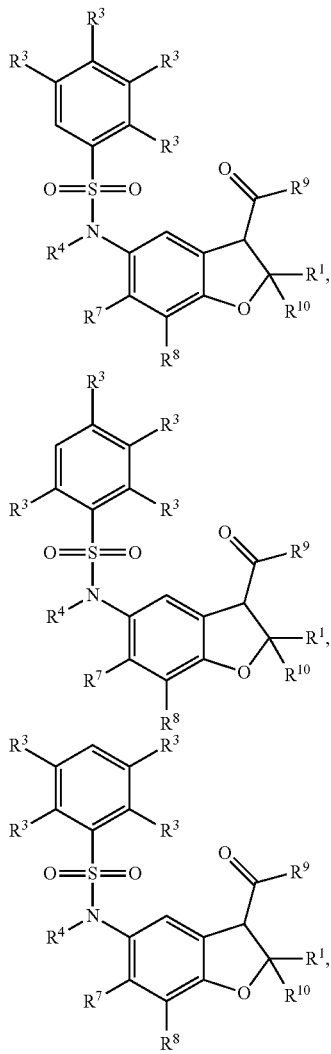

or a pharmaceutically acceptable salt thereof.

In certain embodiments, n is 5, and the compound of Formula (VI) is of the following formula:

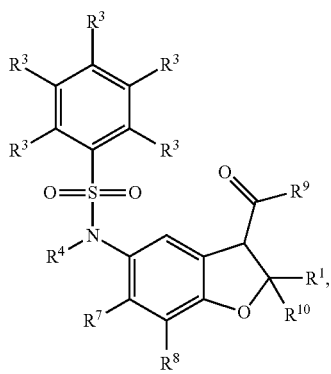

or a pharmaceutically acceptable salt thereof.

In certain embodiments, a compound of Formula (VI) is of the following formula:

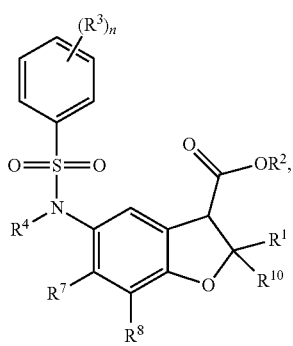

or a pharmaceutically acceptable salt thereof.

In certain embodiments, a compound of Formula (VI) is of the following formula:

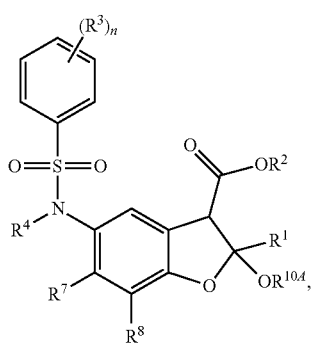

or a pharmaceutically acceptable salt thereof.

In certain embodiments, a compound of Formula (VI) is of the following formula:

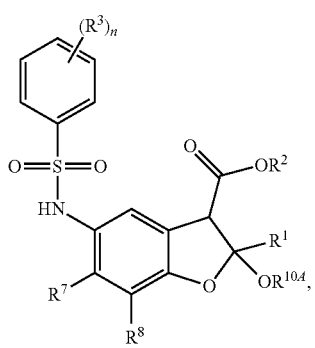

or a pharmaceutically acceptable salt thereof.

In certain embodiments, a compound of Formula (VI) is of the following formula:

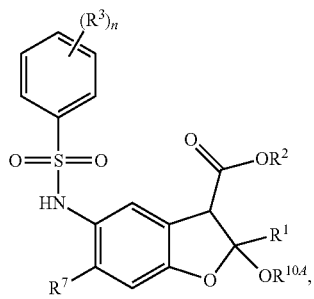

or a pharmaceutically acceptable salt thereof.

In certain embodiments, a compound of Formula (VI) is of the following formula:

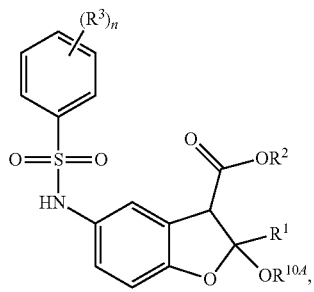

or a pharmaceutically acceptable salt thereof.

In certain embodiments, a compound of Formula (VI) is of the following formula:

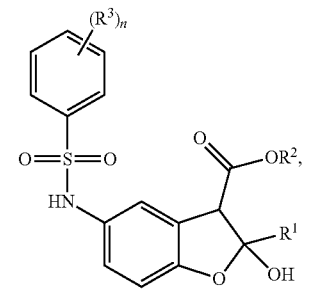

or a pharmaceutically acceptable salt thereof.

In certain embodiments, a compound of Formula (VI) is of the following formula:

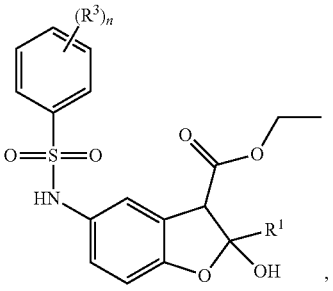

or a pharmaceutically acceptable salt thereof.

In certain embodiments, a compound of Formula (VI) is of the following formula:

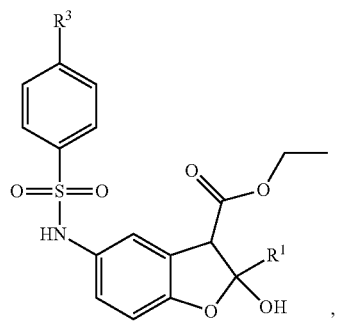

or a pharmaceutically acceptable salt thereof.

In certain embodiments, a compound of Formula (VI) is of the following formula:

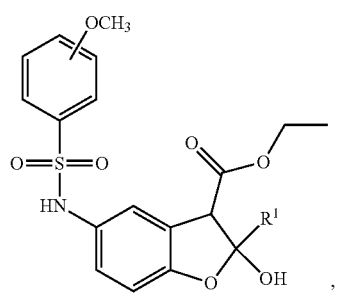

or a pharmaceutically acceptable salt thereof.

In certain embodiments, a compound of Formula (VI) is of the following formula:

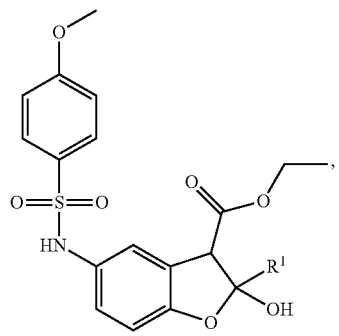

or a pharmaceutically acceptable salt thereof.

For example, a compound of Formula (VI) may be of the following formula:

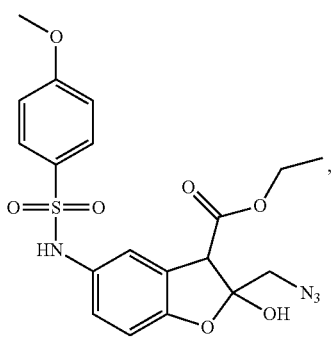 [SMILES: CCOC(=O)C1c2cc(NS(=O)(=O)c3ccc(OC)cc3)ccc2OC1(O)CN=[N+]=[N-]]

or a pharmaceutically acceptable salt thereof.

In certain embodiments, the following compounds are excluded from the present invention:

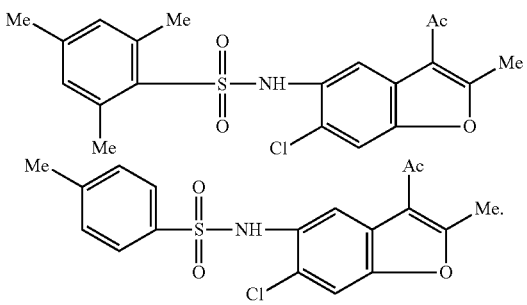

As generally defined herein, n is 0, 1, 2, 3, 4, or 5. In certain embodiments, n is 0. In certain embodiments, n is 1. In certain embodiments, n is 2. In certain embodiments, n is 3. In certain embodiments, n is 4. In certain embodiments, n is 5.

Group $R^1$

As generally defined herein, $R^1$ is hydrogen, halogen, or optionally substituted alkyl.

In certain embodiments, $R^1$ is hydrogen. In certain embodiments, $R^1$ is halogen. In certain embodiments, $R^1$ is —Cl, —Br, —F, or —I. In certain embodiments, $R^1$ is optionally substituted alkyl. In certain embodiments, $R^1$ is optionally substituted $C_{1-6}$ alkyl. In certain embodiments, $R^1$ is unsubstituted $C_{1-6}$ alkyl. In certain embodiments, $R^1$ is methyl. In certain embodiments, $R^1$ is ethyl. In certain embodiments, $R^1$ is n-propyl. In certain embodiments, $R^1$ is iso-propyl. In certain embodiments, $R^1$ is n-butyl, iso-butyl, sec-butyl, or tert-butyl. In certain embodiments, $R^1$ is substituted $C_{1-6}$ alkyl. In certain embodiments, $R^1$ is $C_{1-6}$alkyl substituted with one instance of —O—$C_{1-6}$alkyl. In certain embodiments, $R^1$ is —$C_{1-6}$alkyl-O—$C_{1-6}$alkyl. In certain embodiments, $R^1$ is —$C_{1-3}$alkyl-O—$C_{1-3}$alkyl. In certain embodiments, $R^1$ is —$C_{1-6}$alkyl-OCH$_3$. In certain embodiments, $R^1$ is —$C_{1-3}$alkyl-OCH$_3$. In certain embodiments, $R^1$ is —CH$_2$—O—$C_{1-6}$alkyl. In certain embodiments, $R^1$ is —CH$_2$—O—$C_{1-3}$alkyl. In certain embodiments, $R^1$ is —CH$_2$—O—CH$_3$. In certain embodiments, $R^1$ is —$C_{1-6}$alkyl-N$_3$. In certain embodiments, $R^1$ is —$C_{1-3}$ alkyl-N$_3$. In certain embodiments, $R^1$ is —CH$_2$N$_3$. In certain embodiments, $R^1$ is —$C_{1-6}$ alkyl-CN. In certain embodiments, $R^1$ is —$C_{1-3}$ alkyl-CN. In certain embodiments, $R^1$ is —CH$_2$CN. In certain embodiments, $R^1$ is optionally substituted $C_{1-6}$ alkyl-O—$R^{1O}$, wherein $R^{1O}$ is hydrogen or optionally substituted alkyl. In certain embodiments, $R^1$ is unsubstituted $C_{1-6}$ alkyl-O—$R^{1O}$, wherein $R^{1O}$ is hydrogen or optionally substituted alkyl. In certain embodiments, $R^1$ is optionally substituted $C_{1-6}$ alkyl-O—$R^{1O}$, wherein $R^{1O}$ is hydrogen or optionally substituted alkyl. In certain embodiments, $R^1$ is unsubstituted $C_{1-3}$ alkyl-O—$R^{1O}$, wherein $R^{1O}$ is hydrogen or optionally substituted alkyl. In certain embodiments, $R^1$ is-CH$_2$—O—$R^{1O}$, wherein $R^{1O}$ is hydrogen or optionally substituted alkyl. In certain embodiments, $R^{1O}$ is optionally substituted alkyl. In certain embodiments, $R^{1O}$ is optionally substituted $C_{1-6}$ alkyl. In certain embodiments, $R^{1O}$ is unsubstituted $C_{1-6}$ alkyl. In certain embodiments, $R^{1O}$ is optionally substituted $C_{1-3}$ alkyl. In certain embodiments, $R^{1O}$ is unsubstituted $C_{1-3}$ alkyl. In certain embodiments, $R^{1O}$ is methyl. In certain embodiments, $R^{1O}$ is ethyl. In certain embodiments, $R^{1O}$ is n-propyl. In certain embodiments, $R^{1O}$ is iso-propyl. In certain embodiments, $R^{1O}$ is n-butyl, iso-butyl, sec-butyl, or tert-butyl.

Group $R^2$

As generally defined herein, each instance of $R^2$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group. In certain embodiments, $R^2$ is hydrogen. In certain embodiments, $R^2$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group. In certain embodiments, $R^2$ is optionally substituted alkyl. In certain embodiments, $R^2$ is optionally substituted $C_{1-6}$ alkyl. In certain embodiments, $R^2$ is optionally substituted $C_{1-3}$ alkyl. In certain embodiments, $R^2$ is unsubstituted $C_{1-6}$ alkyl. In certain embodiments, $R^2$ is unsubstituted $C_{1-3}$alkyl. In certain embodiments, $R^2$ is methyl. In certain embodiments, $R^2$ is unsubstituted $C_{1-6}$ alkyl. In certain embodiments, $R^2$ is ethyl. In certain embodiments, $R^2$ is n-propyl. In certain embodiments, $R^2$ is iso-propyl. In certain embodiments, $R^2$ is n-butyl, iso-butyl, sec-butyl, or tert-butyl. In certain embodiments, $R^2$ is substituted $C_{1-6}$ alkyl.

Group $R^3$

As generally defined herein, each instance of $R^3$ is independently halogen, —CN, —NO$_2$, —N$_3$, optionally substituted alkyl, —OR$^{3A}$, —N(R$^{3B}$)$_2$, or optionally substituted acyl. In certain embodiments, at least one instance of $R^3$ is halogen. In certain embodiments, at least one instance of $R^3$ is —F. In certain embodiments, at least one instance of $R^3$ is —Cl. In certain embodiments, at least one instance of $R^3$ is —Br. In certain embodiments, at least one instance of $R^3$ is —I. In certain embodiments, at least one instance of $R^3$ is optionally substituted alkyl. In certain embodiments, at least one instance of $R^3$ is optionally substituted $C_{1-6}$ alkyl. In certain embodiments, at least one instance of $R^3$ is unsubstituted $C_{1-6}$alkyl. In certain embodiments, at least one instance of $R^3$ is optionally substituted $C_{1-3}$alkyl. In certain embodiments, at least one instance of $R^3$ is unsubstituted $C_{1-3}$alkyl. In certain embodiments, at least one instance of $R^3$ is methyl or ethyl. In certain embodiments, at least one instance of $R^3$ is methyl. In certain embodiments, at least one instance of $R^3$ is n-propyl. In certain embodiments, at least one instance of $R^3$ is iso-propyl. In certain embodiments, at least one instance of $R^3$ is n-butyl, iso-butyl, sec-butyl, or tert-butyl. In certain embodiments, at least one instance of $R^3$ is substituted $C_{1-6}$alkyl. In certain embodiments, at least one instance of $R^3$ is —OR$^{3A}$; and R$^{3A}$ is as defined herein. In certain embodiments, at least one instance of $R^3$ is —OH.

In certain embodiments, at least one instance of $R^3$ is —$OR^{3A}$; and $R^{3A}$ is optionally substituted alkyl. In certain embodiments, at least one instance of $R^3$ is —$OR^{3A}$; and $R^{3A}$ is optionally substituted $C_{1-6}$ alkyl. In certain embodiments, at least one instance of $R^3$ is —$OR^{3A}$; and $R^{3A}$ is unsubstituted $C_{1-6}$ alkyl. In certain embodiments, at least one instance of $R^3$ is —$OR^{3A}$; and $R^{3A}$ is optionally substituted $C_{1-3}$ alkyl. In certain embodiments, at least one instance of $R^3$ is —$OR^{3A}$; and $R^{3A}$ is unsubstituted $C_{1-3}$ alkyl. In certain embodiments, at least one instance of $R^3$ is —$OCH_3$. In certain embodiments, at least one instance of $R^3$ is —OEt. In certain embodiments, at least one instance of $R^3$ is —OPr. In certain embodiments, at least one instance of $R^3$ is —$O^iPr$. In certain embodiments, at least one instance of $R^3$ is —$OR^{3A}$; and $R^{3A}$ is substituted $C_{1-6}$ alkyl. In certain embodiments, at least one instance of $R^3$ is —$N(R^{3B})_2$ and each instance of $R^{3B}$ is as defined herein. In certain embodiments, at least one instance of $R^3$ is —$N(R^{3B})_2$; and each instance of $R^{3B}$ is hydrogen, optionally substituted alkyl, or a nitrogen protecting group. In certain embodiments, at least one instance of $R^3$ is —$NHR^{3B}$; and $R^{3B}$ is as defined herein. In certain embodiments, at least one instance of $R^3$ is —$NHR^{3B}$ and $R^{3B}$ is hydrogen, optionally substituted alkyl, or a nitrogen protecting group. In certain embodiments, at least one instance of $R^3$ is —$NH_2$. In certain embodiments, at least one instance of $R^3$ is —$NHR^{3B}$ and $R^{3B}$ is as defined herein. In certain embodiments, at least one instance of $R^3$ is —$NHR^{3B}$ and $R^{3B}$ is hydrogen, optionally substituted alkyl, or a nitrogen protecting group. In certain embodiments, at least one instance of $R^3$ is —$NH_2$. In certain embodiments, at least one instance of $R^3$ is —$N(CH_3)R^{3B}$; and $R^{3B}$ is as defined herein. In certain embodiments, at least one instance of $R^3$ is —$N(CH_3)R^{3B}$; and $R^{3B}$ is hydrogen, optionally substituted alkyl, or a nitrogen protecting group. In certain embodiments, at least one instance of $R^3$ is —$NHCH_3$. In certain embodiments, at least one instance of $R^3$ is —$N(CH_3)R^{3B}$ and $R^{3B}$ is optionally substituted alkyl. In certain embodiments, at least one instance of $R^3$ is —$N(CH_3)R^{3B}$ and $R^{3B}$ is optionally substituted $C_{1-6}$ alkyl. In certain embodiments, at least one instance of $R^3$ is —$N(CH_3)R^{3B}$ and $R^{3B}$ is unsubstituted $C_{1-6}$ alkyl. In certain embodiments, at least one instance of $R^3$ is —$N(CH_3)_2$. In certain embodiments, at least one instance of $R^3$ is —$N(CH_3)R^{3B}$ and $R^{3B}$ is substituted $C_{1-6}$ alkyl.

As generally defined herein, each instance of $R^{3A}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group. In certain embodiments, $R^{3A}$ is hydrogen. In certain embodiments, $R^{3A}$ is optionally substituted alkyl. In certain embodiments, $R^{3A}$ is optionally substituted alkenyl. In certain embodiments, $R^{3A}$ is optionally substituted alkynyl. In certain embodiments, $R^{3A}$ is optionally substituted carbocyclyl. In certain embodiments, $R^{3A}$ is optionally substituted heterocyclyl. In certain embodiments, $R^{3A}$ is optionally substituted aryl. In certain embodiments, $R^{3A}$ is optionally substituted heteroaryl. In certain embodiments, $R^{3A}$ is an oxygen protecting group.

As generally defined herein, each instance of $R^{3B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{3B}$ are taken together with the intervening atoms to form optionally substituted heterocyclyl. In certain embodiments, $R^{3B}$ is hydrogen. In certain embodiments, $R^{3B}$ is optionally substituted alkyl. In certain embodiments, $R^{3B}$ is optionally substituted alkenyl. In certain embodiments, $R^{3B}$ is optionally substituted alkynyl. In certain embodiments, $R^{3B}$ is optionally substituted carbocyclyl. In certain embodiments, $R^{3B}$ is optionally substituted heterocyclyl. In certain embodiments, $R^{3B}$ is optionally substituted aryl. In certain embodiments, $R^{3B}$ is optionally substituted heteroaryl. In certain embodiments, $R^{3B}$ is or a nitrogen protecting group. In certain embodiments, two $R^{3B}$ are taken together with the intervening atoms to form optionally substituted heterocyclyl.

Group $R^4$

As generally defined herein, $R^4$ is hydrogen, optionally substituted alkyl, or a nitrogen protecting group. In certain embodiments, $R^4$ is hydrogen. In certain embodiments, $R^4$ is optionally substituted alkyl or a nitrogen protecting group. In certain embodiments, $R^4$ is optionally substituted alkyl. In certain embodiments, $R^4$ is optionally substituted $C_{1-6}$ alkyl. In certain embodiments, $R^4$ is unsubstituted $C_{1-6}$ alkyl. In certain embodiments, $R^4$ is methyl. In certain embodiments, $R^4$ is ethyl. In certain embodiments, $R^4$ is a nitrogen protecting group. In certain embodiments, $R^4$ is optionally substituted acyl. In certain embodiments, $R^4$ is acetyl (e.g., —$C(=O)CH_3$. In certain embodiments, $R^4$ is —$C(=O)C_{1-6}$ alkyl. In certain embodiments, $R^4$ is —$C(=O)C_{1-3}$ alkyl. In certain embodiments, $R^4$ is —$C(=O)CH_2CH_2CH_3$.

Group $R^5$

As generally defined herein, $R^5$ is halogen or optionally substituted alkyl. In certain embodiments, $R^5$ is halogen. In certain embodiments, $R^5$ is fluorine (—F). In certain embodiments, $R^5$ is chlorine (—Cl). In certain embodiments, $R^5$ is bromine (—Br). In certain embodiments, $R^5$ is iodine (—I). In certain embodiments, $R^5$ is optionally substituted alkyl. In certain embodiments, $R^5$ is optionally substituted $C_{1-6}$ alkyl. In certain embodiments, $R^5$ is unsubstituted $C_{1-6}$ alkyl. In certain embodiments, $R^5$ is methyl. In certain embodiments, $R^5$ is ethyl. In certain embodiments, $R^5$ is a nitrogen protecting group. In certain embodiments, $R^5$ is optionally substituted acyl. In certain embodiments, $R^5$ is acetyl.

Group $R^6$

As generally defined herein, $R^6$ is halogen, —CN, —$NO_2$, —$N_3$, optionally substituted alkyl, —$OR^{6A}$, —$N(R^{6B})_2$, or optionally substituted acyl. In certain embodiments, $R^6$ is halogen. In certain embodiments, $R^6$ is —F. In certain embodiments, $R^6$ is —Cl. In certain embodiments, $R^6$ is —Br. In certain embodiments, $R^6$ is —I. In certain embodiments, $R^6$ is optionally substituted alkyl. In certain embodiments, $R^6$ is optionally substituted $C_{1-6}$ alkyl. In certain embodiments, $R^6$ is unsubstituted $C_{1-6}$ alkyl. In certain embodiments, $R^6$ is methyl or ethyl. In certain embodiments, $R^6$ is substituted $C_{1-6}$ alkyl. In certain embodiments, $R^6$ is —$OR^{6A}$; and $R^{6A}$ is as defined herein. In certain embodiments, $R^6$ is —OH. In certain embodiments, $R^6$ is —$OR^{6A}$; and $R^{6A}$ is optionally substituted alkyl. In certain embodiments, $R^3$ is —$OR^{6A}$; and $R^{6A}$ is optionally substituted $C_{1-6}$ alkyl. In certain embodiments, $R^6$ is —$OR^{6A}$; and $R^{6A}$ is unsubstituted $C_{1-6}$ alkyl. In certain embodiments, $R^6$ is —$OCH_3$. In certain embodiments, $R^6$ is —OEt. In certain embodiments, $R^6$ is —OPr. In certain embodiments, $R^6$ is —$O^iPr$. In certain embodiments, $R^6$ is —$OR^{6A}$ and $R^{6A}$ is substituted $C_{1-6}$ alkyl. In certain embodiments, $R^6$ is —$N(R^{6B})_2$ and each instance of $R^{6B}$ is as defined herein. In certain embodiments, $R^6$ is —$N(R^{6B})_2$ and each instance of $R^{6B}$ is hydrogen, optionally substituted alkyl, or a nitrogen protecting group. In certain embodiments, $R^6$ is —NHR$^{6B}$ and R$^{6B}$ is as defined herein. In certain embodiments, $R^6$ is —NHR$^{6B}$ and R$^{6B}$ is hydrogen, optionally substituted alkyl, or a nitrogen protecting group. In certain embodiments, $R^6$ is —NH$_2$. In certain embodiments, $R^6$ is —NHR$^{6B}$ and R$^{6B}$ is as defined herein. In certain embodiments, $R^6$ is —NHR$^{6B}$ and R$^{6B}$ is hydrogen, optionally substituted alkyl, or a nitrogen protecting group. In certain embodiments, $R^6$ is —NH$_2$. In certain embodiments, $R^6$ is —N(CH$_3$)R$^{6B}$; and R$^{6B}$ is as defined herein. In certain embodiments, $R^6$ is —N(CH$_3$)R$^{6B}$; and R$^{6B}$ is hydrogen, optionally substituted alkyl, or a nitrogen protecting group. In certain embodiments, $R^6$ is —NHCH$_3$. In certain embodiments, $R^6$ is —N(CH$_3$)R$^{6B}$; and R$^{6B}$ is optionally substituted alkyl. In certain embodiments, $R^6$ is —N(CH$_3$)R$^{6B}$; and R$^{6B}$ is optionally substituted C$_{1-6}$ alkyl. In certain embodiments, $R^6$ is —N(CH$_3$)R$^{6B}$; and R$^{6B}$ is unsubstituted C$_{1-6}$ alkyl. In certain embodiments, $R^6$ is —N(CH$_3$)$_2$. In certain embodiments, $R^6$ is —N(CH$_3$)R$^{6B}$; and R$^{6B}$ is substituted C$_{1-6}$ alkyl.

As generally defined herein, each instance of R$^{6A}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group. In certain embodiments, R$^{6A}$ is hydrogen. In certain embodiments, R$^{6A}$ is optionally substituted alkyl. In certain embodiments, R$^{6A}$ is optionally substituted alkenyl. In certain embodiments, R$^{6A}$ is optionally substituted alkynyl. In certain embodiments, R$^{6A}$ is optionally substituted carbocyclyl. In certain embodiments, R$^{6A}$ is optionally substituted heterocyclyl. In certain embodiments, R$^{6A}$ is optionally substituted aryl. In certain embodiments, R$^{6A}$ is optionally substituted heteroaryl. In certain embodiments, R$^{6A}$ is an oxygen protecting group.

As generally defined herein, each instance of R$^{6B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two R$^{6B}$ are taken together with the intervening atoms to form optionally substituted heterocyclyl. In certain embodiments, R$^{6B}$ is hydrogen. In certain embodiments, R$^{6B}$ is optionally substituted alkyl. In certain embodiments, R$^{6B}$ is optionally substituted alkenyl. In certain embodiments, R$^{6B}$ is optionally substituted alkynyl. In certain embodiments, R$^{6B}$ is optionally substituted carbocyclyl. In certain embodiments, R$^{6B}$ is optionally substituted heterocyclyl. In certain embodiments, R$^{6B}$ is optionally substituted aryl. In certain embodiments, R$^{6B}$ is optionally substituted heteroaryl. In certain embodiments, R$^{6B}$ is or a nitrogen protecting group. In certain embodiments, two R$^{6B}$ are taken together with the intervening atoms to form optionally substituted heterocyclyl.

Group R$^7$

As generally defined herein, $R^7$ is hydrogen, halogen, —CN, —NO$_2$, —N$_3$, optionally substituted alkyl, —OR$^{7A}$, —N(R$^{7B}$)$_2$, or optionally substituted acyl. In certain embodiments, $R^7$ is hydrogen. In certain embodiments, $R^7$ is halogen. In certain embodiments, $R^7$ is F. In certain embodiments, $R^7$ is Cl. In certain embodiments, $R^7$ is Br. In certain embodiments, $R^7$ is I. In certain embodiments, $R^7$ is —CN. In certain embodiments, $R^7$ is —NO$_2$. In certain embodiments, $R^7$ is —N$_3$. In certain embodiments, $R^7$ is optionally substituted acyl. In certain embodiments, $R^7$ is optionally substituted alkyl. In certain embodiments, $R^7$ is optionally substituted C$_{1-6}$ alkyl. In certain embodiments, $R^7$ is unsubstituted C$_{1-6}$ alkyl. In certain embodiments, $R^7$ is optionally substituted C$_{1-3}$ alkyl. In certain embodiments, $R^7$ is unsubstituted C$_{1-3}$ alkyl. In certain embodiments, $R^7$ is methyl or ethyl. In certain embodiments, $R^7$ is n-propyl, iso-propyl, n-butyl, iso-butyl, sec-butyl, or tert-butyl. In certain embodiments, $R^7$ is substituted C$_{1-6}$ alkyl. In certain embodiments, $R^7$ is —OR$^{7A}$; and R$^{7A}$ is as defined herein. In certain embodiments, $R^7$ is —OH. In certain embodiments, $R^7$ is —OR$^{7A}$; and R$^{7A}$ is optionally substituted alkyl. In certain embodiments, $R^7$ is —OR$^{7A}$; and R$^{7A}$ is optionally substituted C$_{1-6}$ alkyl. In certain embodiments, $R^7$ is —OR$^{7A}$; and R$^{7A}$ is unsubstituted C$_{1-6}$ alkyl. In certain embodiments, $R^7$ is —N(R$^{7B}$)$_2$ and each instance of R$^{7B}$ is as defined herein. In certain embodiments, $R^7$ is —N(R$^{7B}$)$_2$ and each instance of R$^{7B}$ is hydrogen, optionally substituted alkyl, or a nitrogen protecting group. In certain embodiments, $R^7$ is —NHR$^{7B}$ and R$^{7B}$ is as defined herein. In certain embodiments, $R^7$ is —NHR$^{7B}$ and R$^{7B}$ is hydrogen, optionally substituted alkyl, or a nitrogen protecting group. In certain embodiments, $R^7$ is —NH$_2$. In certain embodiments, $R^7$ is —NMe$_2$.

As generally defined herein, each instance of R$^{7A}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group. In certain embodiments, R$^{7A}$ is hydrogen. In certain embodiments, R$^{7A}$ is optionally substituted alkyl. In certain embodiments, R$^{7A}$ is optionally substituted alkenyl. In certain embodiments, R$^{7A}$ is optionally substituted alkynyl. In certain embodiments, R$^{7A}$ is optionally substituted carbocyclyl. In certain embodiments, R$^{7A}$ is optionally substituted heterocyclyl. In certain embodiments, R$^{7A}$ is optionally substituted aryl. In certain embodiments, R$^{7A}$ is optionally substituted heteroaryl. In certain embodiments, R$^{7A}$ is an oxygen protecting group.

As generally defined herein, each instance of R$^{7B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two R$^{7B}$ are taken together with the intervening atoms to form optionally substituted heterocyclyl. In certain embodiments, R$^{7B}$ is hydrogen. In certain embodiments, R$^{7B}$ is optionally substituted alkyl. In certain embodiments, R$^{7B}$ is optionally substituted alkenyl. In certain embodiments, R$^{7B}$ is optionally substituted alkynyl. In certain embodiments, R$^{7B}$ is optionally substituted carbocyclyl. In certain embodiments, R$^{7B}$ is optionally substituted heterocyclyl. In certain embodiments, R$^{7B}$ is optionally substituted aryl. In certain embodiments, R$^{7B}$ is optionally substituted heteroaryl. In certain embodiments, R$^{7B}$ is or a nitrogen protecting group. In certain embodiments, two R$^{7B}$ are taken together with the intervening atoms to form optionally substituted heterocyclyl.

Group R$^8$

As generally defined herein, $R^8$ is hydrogen, halogen, —CN, —NO$_2$, —N$_3$, optionally substituted alkyl, —OR$^{8A}$, —N(R$^{8B}$)$_2$, or optionally substituted acyl. In certain embodiments, $R^8$ is hydrogen. In certain embodiments, $R^8$ is halogen. In certain embodiments, $R^8$ is F. In certain embodiments, $R^8$ is Cl. In certain embodiments, $R^8$ is Br. In certain embodiments, $R^8$ is I. In certain embodiments, $R^8$ is —CN. In certain embodiments, $R^8$ is —NO$_2$. In certain embodiments, $R^8$ is —$N_3$. In certain embodiments, $R^8$ is optionally substituted acyl. In certain embodiments, $R^8$ is optionally substituted alkyl. In certain embodiments, $R^8$ is optionally substituted $C_{1-6}$ alkyl. In certain embodiments, $R^8$ is unsubstituted $C_{1-6}$ alkyl. In certain embodiments, $R^8$ is optionally substituted $C_{1-3}$ alkyl. In certain embodiments, $R^8$ is unsubstituted $C_{1-3}$ alkyl. In certain embodiments, $R^8$ is methyl or ethyl. In certain embodiments, $R^8$ is n-propyl, iso-propyl, n-butyl, iso-butyl, sec-butyl, or tert-butyl. In certain embodiments, $R^8$ is substituted $C_{1-6}$ alkyl. In certain embodiments, $R^8$ is —$OR^{8A}$; and $R^{8A}$ is as defined herein. In certain embodiments, $R^8$ is —OH. In certain embodiments, $R^8$ is —$OR^{7A}$; and $R^{8A}$ is optionally substituted alkyl. In certain embodiments, $R^8$ is —$OR^{8A}$; and $R^{8A}$ is optionally substituted $C_{1-6}$ alkyl. In certain embodiments, $R^8$ is —$OR^{8A}$; and $R^{8A}$ is unsubstituted $C_{1-6}$ alkyl. In certain embodiments, $R^8$ is —$N(R^{8B})_2$ and each instance of $R^{8B}$ is as defined herein. In certain embodiments, $R^8$ is —$N(R^{8B})_2$ and each instance of $R^{8B}$ is hydrogen, optionally substituted alkyl, or a nitrogen protecting group. In certain embodiments, $R^8$ is —$NHR^{8B}$ and $R^{8B}$ is as defined herein. In certain embodiments, $R^8$ is —$NHR^{8B}$ and $R^{8B}$ is hydrogen, optionally substituted alkyl, or a nitrogen protecting group. In certain embodiments, $R^8$ is —$NH_2$. In certain embodiments, $R^8$ is —$NMe_2$.

As generally defined herein, each instance of $R^{8A}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group. In certain embodiments, $R^{8A}$ is hydrogen. In certain embodiments, $R^{8A}$ is optionally substituted alkyl. In certain embodiments, $R^{8A}$ is optionally substituted alkenyl. In certain embodiments, $R^{8A}$ is optionally substituted alkynyl. In certain embodiments, $R^{8A}$ is optionally substituted carbocyclyl. In certain embodiments, $R^{8A}$ is optionally substituted heterocyclyl. In certain embodiments, $R^{8A}$ is optionally substituted aryl. In certain embodiments, $R^{8A}$ is optionally substituted heteroaryl. In certain embodiments, $R^{8A}$ is an oxygen protecting group.

As generally defined herein, each instance of $R^{8B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{8B}$ taken together with the intervening atoms to form optionally substituted heterocyclyl. In certain embodiments, $R^{8B}$ is hydrogen. In certain embodiments, $R^{8B}$ is optionally substituted alkyl. In certain embodiments, $R^{8B}$ is optionally substituted alkenyl. In certain embodiments, $R^{8B}$ is optionally substituted alkynyl. In certain embodiments, $R^{8B}$ is optionally substituted carbocyclyl. In certain embodiments, $R^{8B}$ is optionally substituted heterocyclyl. In certain embodiments, $R^{8B}$ is optionally substituted aryl. In certain embodiments, $R^{8B}$ is optionally substituted heteroaryl. In certain embodiments, $R^{8B}$ is or a nitrogen protecting group. In certain embodiments, two $R^{8B}$ are taken together with the intervening atoms to form optionally substituted heterocyclyl.

Group $R^N$

As generally defined herein, each instance of $R^N$ is independently hydrogen, optionally substituted alkyl, —$OR^{NA}$, —$N(R^{NB})_2$, or a nitrogen protecting group or two $R^N$ taken together with the intervening atoms form optionally substituted heterocyclyl; provided that at least one instance of $R^N$ is not hydrogen, —OH, or —$NH_2$. In certain embodiments, one instance of $R^N$ is hydrogen. In certain embodiments, at least one instance of $R^N$ is optionally substituted alkyl. In certain embodiments, at least one instance of $R^N$ is optionally substituted $C_{1-6}$ alkyl. In certain embodiments, at least one instance of $R^N$ is unsubstituted $C_{1-6}$ alkyl. In certain embodiments, at least one instance of $R^N$ is substituted $C_{1-6}$ alkyl. In certain embodiments, at least one instance of $R^N$ is optionally substituted $C_{1-3}$ alkyl. In certain embodiments, at least one instance of $R^N$ is unsubstituted $C_{1-3}$ alkyl. In certain embodiments, at least one instance of $R^N$ is substituted $C_{1-3}$ alkyl. In certain embodiments, at least one instance of $R^N$ is methyl, ethyl, n-propyl, iso-propyl, n-butyl, iso-butyl, sec-butyl, or tert-butyl. In certain embodiments, at least one instance of $R^N$ is —$C_{1-6}$ alkyl-CN. In certain embodiments, at least one instance of $R^N$ is —$C_{1-3}$ alkyl-CN. In certain embodiments, at least one instance of $R^N$ is —$CH_2CN$. In certain embodiments, one instance of $R^N$ is —$CH_2CN$. In certain embodiments, at least one instance of $R^N$ is —$OR^{NA}$, and $R^{NA}$ is optionally substituted alkyl. In certain embodiments, at least one instance of $R^N$ is —$OR^{NA}$, and $R^{NA}$ is optionally substituted $C_{1-6}$ alkyl. In certain embodiments, at least one instance of $R^N$ is —$OR^{NA}$, and $R^{NA}$ is unsubstituted $C_{1-6}$ alkyl. In certain embodiments, at least one instance of $R^N$ is —$OR^NA$, and $R^{NA}$ is optionally substituted $C_{1-3}$ alkyl. In certain embodiments, at least one instance of $R^N$ is —$OR^{NA}$, and $R^{NA}$ is unsubstituted $C_{1-3}$ alkyl. In certain embodiments, at least one instance of $R^N$ is —$OR^{NA}$, and $R^{NA}$ is methyl, ethyl, n-propyl, iso-propyl, n-butyl, iso-butyl, sec-butyl, or tert-butyl. In certain embodiments, one instance of $R^N$ is —$OC_{1-6}$ alkyl. In certain embodiments, one instance of $R^N$ is —$OC_{1-3}$ alkyl. In certain embodiments, one instance of $R^N$ is —$OCH_3$.

As generally defined herein, each instance of $R^{NA}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group. In certain embodiments, $R^{NA}$ is hydrogen. In certain embodiments, $R^{NA}$ is optionally substituted alkyl. In certain embodiments, $R^{NA}$ is optionally substituted alkenyl. In certain embodiments, $R^{NA}$ is optionally substituted alkynyl. In certain embodiments, $R^{NA}$ is optionally substituted carbocyclyl. In certain embodiments, $R^{NA}$ is optionally substituted heterocyclyl. In certain embodiments, $R^{NA}$ is optionally substituted aryl. In certain embodiments, $R^{NA}$ is optionally substituted heteroaryl. In certain embodiments, $R^{NA}$ is an oxygen protecting group.

As generally defined herein, each instance of $R^{NB}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{NB}$ are taken together with the intervening atoms to form optionally substituted heterocyclyl. In certain embodiments, $R^{NB}$ is hydrogen. In certain embodiments, $R^{NB}$ is optionally substituted alkyl. In certain embodiments, $R^{NB}$ is optionally substituted alkenyl. In certain embodiments, $R^{NB}$ is optionally substituted alkynyl. In certain embodiments, $R^{NB}$ is optionally substituted carbocyclyl. In certain embodiments, $R^{NB}$ is optionally substituted heterocyclyl. In certain embodiments, $R^{NB}$ is optionally substituted aryl. In certain embodiments, $R^{NB}$ is optionally substituted heteroaryl. In certain embodiments, $R^{NB}$ is or a nitrogen protecting group.

In certain embodiments, two $R^{NB}$ are taken together with the intervening atoms to form optionally substituted heterocyclyl.

Group $R^9$

As generally defined herein, $R^9$ is hydrogen, optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted acyl, —$OR^2$, or —$N(R^{9B})_2$. In certain embodiments, $R^9$ is hydrogen. In certain embodiments, $R^9$ is hydrogen. In certain embodiments, $R^9$ is optionally substituted alkyl. In certain embodiments, $R^9$ is optionally substituted $C_{1-6}$ alkyl. In certain embodiments, $R^9$ is unsubstituted $C_{1-6}$ alkyl. In certain embodiments, $R^9$ is optionally substituted $C_{1-3}$ alkyl. In certain embodiments, $R^9$ is unsubstituted $C_{1-3}$ alkyl. In certain embodiments, $R^9$ is methyl or ethyl. In certain embodiments, $R^9$ is n-propyl, iso-propyl, n-butyl, iso-butyl, sec-butyl, or tert-butyl. In certain embodiments, $R^9$ is optionally substituted alkenyl. In certain embodiments, $R^9$ is optionally substituted alkynyl. In certain embodiments, $R^9$ is optionally substituted aryl. In certain embodiments, $R^9$ is optionally substituted heteroaryl. In certain embodiments, $R^9$ is optionally substituted carbocyclyl. In certain embodiments, $R^9$ is optionally substituted heterocyclyl. In certain embodiments, $R^9$ is optionally substituted acyl. In certain embodiments, $R^9$ is —$OR^2$. In certain embodiments, $R^9$ is —$OR^2$, and $R^2$ is optionally substituted alkyl. In certain embodiments, $R^9$ is —$OR^2$, and $R^2$ is optionally substituted $C_{1-6}$ alkyl. In certain embodiments, $R^9$ is —$OR^2$, and $R^2$ is unsubstituted $C_{1-6}$ alkyl. In certain embodiments, $R^9$ is —$OR^2$, and $R^2$ is optionally substituted $C_{1-3}$ alkyl. In certain embodiments, $R^9$ is —$OR^2$, and $R^2$ is unsubstituted $C_{1-3}$ alkyl. In certain embodiments, $R^9$ is —$OR^2$, and $R^2$ is methyl, ethyl, n-propyl, iso-propyl, n-butyl, iso-butyl, sec-butyl, or tert-butyl. In certain embodiments, $R^9$ is —$OCH_3$. In certain embodiments, $R^9$ is —$OCH_2CH_3$. In certain embodiments, $R^9$ is —$N(R^{9B})_2$.

As generally defined herein, each instance of $R^{9B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{9B}$ are taken together with the intervening atoms to form optionally substituted heterocyclyl. In certain embodiments, $R^{9B}$ is hydrogen. In certain embodiments, $R^{9B}$ is optionally substituted alkyl. In certain embodiments, $R^{9B}$ is optionally substituted alkenyl. In certain embodiments, $R^{9B}$ is optionally substituted alkynyl. In certain embodiments, $R^{9B}$ is optionally substituted carbocyclyl. In certain embodiments, $R^{9B}$ is optionally substituted heterocyclyl. In certain embodiments, $R^{9B}$ is optionally substituted aryl. In certain embodiments, $R^{9B}$ is optionally substituted heteroaryl. In certain embodiments, $R^{9B}$ is or a nitrogen protecting group. In certain embodiments, two $R^{9B}$ are taken together with the intervening atoms to form optionally substituted heterocyclyl.

Group $R^{10}$

As generally defined herein, $R^{10}$ is optionally substituted alkyl or —$OR^{10A}$. In certain embodiments, $R^1$ is optionally substituted alkyl. In certain embodiments, $R^{10}$ is optionally substituted $C_{1-6}$ alkyl. In certain embodiments, $R^{10}$ is unsubstituted $C_{1-6}$ alkyl. In certain embodiments, $R^{10}$ is optionally substituted $C_{1-3}$ alkyl. In certain embodiments, $R^{10}$ is unsubstituted $C_{1-3}$ alkyl. In certain embodiments, $R^{10}$ is methyl or ethyl. In certain embodiments, $R^{10}$ is n-propyl, iso-propyl, n-butyl, iso-butyl, sec-butyl, or tert-butyl. In certain embodiments, $R^{10}$ is —$OR^{10A}$, and $R^{10}$ is optionally substituted alkyl. In certain embodiments, $R^{10}$ is —$OR^{10A}$, and $R^{10}$ is hydrogen. In certain embodiments, $R^{10}$ is —OH. As generally defined herein, $R^{10A}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group. In certain embodiments, $R^{10A}$ is hydrogen. In certain embodiments, $R^{10A}$ is optionally substituted alkyl. In certain embodiments, $R^{10A}$ is optionally substituted alkenyl. In certain embodiments, $R^{10A}$ is optionally substituted alkynyl. In certain embodiments, $R^{10A}$ is optionally substituted carbocyclyl. In certain embodiments, $R^{10A}$ is optionally substituted heterocyclyl. In certain embodiments, $R^{10A}$ is optionally substituted aryl. In certain embodiments, $R^{10A}$ is optionally substituted heteroaryl. In certain embodiments, $R^{10A}$ is an oxygen protecting group.

Pharmaceutical Compositions, Kits, and Administration

The present invention provides pharmaceutical compositions comprising a compound of Formula (I), (II), (III), (IV), (V), or (VI), or a pharmaceutically acceptable salt, solvate, hydrate, polymorph, co-crystal, tautomer, stereoisomer, isotopically labeled derivative, or prodrug thereof, as described herein, and optionally a pharmaceutically acceptable excipient. In certain embodiments, the pharmaceutical composition of the invention comprises a compound of Formula (I), (II), (III), (IV), (V), or (VI), or a pharmaceutically acceptable salt thereof, and optionally a pharmaceutically acceptable excipient. In certain embodiments, the compound of Formula (I), (II), (III), (IV), (V), or (VI), or a pharmaceutically acceptable salt, solvate, hydrate, polymorph, co-crystal, tautomer, stereoisomer, isotopically labeled derivative, or prodrug thereof, is provided in an effective amount in the pharmaceutical composition. In certain embodiments, the effective amount is a therapeutically effective amount. In certain embodiments, the effective amount is a prophylactically effective amount. In certain embodiments, the provided pharmaceutical compositions can be used to treat a proliferative disease in a subject. In certain embodiments, the proliferative disease is cancer. In certain embodiments, the cancer is associated with aberrant activities of anti-apoptotic BCL-2 family proteins. In certain embodiments, the cancer is associated with aberrant activities of BCL-2. In certain embodiments, the cancer is associated with aberrant activities of BCL-$X_L$. In certain embodiments, the cancer is associated with MCL-1. In certain embodiments, the cancer is associated with overexpression of BCL-2. In certain embodiments, the cancer is associated with overexpression of BCL-$X_L$. In certain embodiments, the cancer is associated with overexpression of an anti-apoptotic BCL-2 family protein. In certain embodiments, the cancer is associated with overexpression of MCL-1. In certain embodiments, the proliferative disease is an inflammatory disease. In certain embodiments, the inflammatory disease is arthritis. In certain embodiments, the proliferative disease is an autoimmune disease. In certain embodiments, the autoimmune disease is autoimmune glomerulonephritis, immunoglobulinemia, or systemic lupus erythematosus (SLE).

Pharmaceutical compositions described herein can be prepared by any method known in the art of pharmacology. In general, such preparatory methods include the steps of bringing the compound of Formula (I), (II), (III), (IV), (V), or (VI) into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner.

Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Jet injection devices which deliver liquid compositions to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil-in-water and/or water-in-oil emulsions such as creams, ointments, and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets, and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formulae (I), (II), (III), (IV), (V), or (VI) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, anti-bacterial agents, anti-viral agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for preventing and/or treating a proliferative disease (e.g., cancer (e.g., leukemia, breast cancer, lung cancer, colon cancer, or cervical cancer), benign neoplasm, angiogenesis, inflammatory disease, autoinflammatory disease, or autoimmune disease). The inventive kits may also be useful for preventing and/or treating an infectious disease (e.g., a bacterial infection, a viral infection, a fungal infection, or a parasitic disease). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, and prodrug thereof, or a pharmaceutical composition thereof. In certain embodiments, the kit of the invention includes a first container comprising a compound described herein, or a pharmaceutically acceptable salt thereof, or a pharmaceutical composition thereof. In certain embodiments, the kits are useful in preventing and/or treating a proliferative disease in a subject. In certain embodiments, the kits are useful in preventing and/or treating an infectious disease in a subject. In certain embodiments, the kits further include instructions for administering the compound, or a pharmaceutically acceptable salt, solvate, hydrate, polymorph, co-crystal, tautomer, stereoisomer, isotopically labeled derivative, and prodrug thereof, or a pharmaceutical composition thereof, to a subject to prevent and/or treat a proliferative disease.

Methods of Treatment and Uses

The present invention also provides methods of using compounds of Formulae (I), (II), (III), (IV), (V), and (VI), and pharmaceutically acceptable salts, solvates, hydrates, polymorphs, co-crystals, tautomers, stereoisomers, isotopically labeled derivatives, and prodrugs thereof, and pharmaceutical compositions thereof, for the treatment and/or prevention of a proliferative disease such as cancer (e.g., leukemia, breast cancer, lung cancer, colon cancer, liver cancer, bladder cancer, multiple myeloma, or lymphoma), benign neoplasm, diseases related to angiogenesis, inflammatory disease, autoinflammatory disease, or autoimmune disease in a subject. Any of the compounds provided herein (including, but not limited to, the genera, subclasses, and species provided herein) can be used in the methods described herein.

As described herein, the present invention provides methods of using compounds of Formula (IV), and pharmaceutically acceptable salts thereof, for the treatment and/or prevention of proliferative diseases. Provided herein are compounds of Formula (IV):

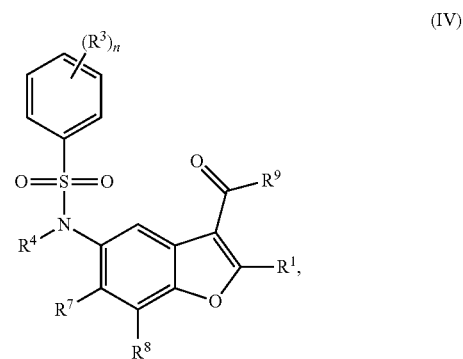

(IV)

and pharmaceutically acceptable salts thereof, wherein:

$R^1$ is hydrogen, halogen, or optionally substituted alkyl;

each instance of $R^3$ is independently halogen, —CN, —NO$_2$, —N$_3$, optionally substituted alkyl, —OR$^{3A}$, —N(R$^{3B}$)$_2$, or optionally substituted acyl;

$R^{3A}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and $R^{3B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{3B}$ are taken together with the intervening atoms to form optionally substituted heterocyclyl.

n is 0, 1, 2, 3, 4, or 5;

$R^4$ is hydrogen, optionally substituted alkyl, or a nitrogen protecting group;

$R^7$ is hydrogen, halogen, —CN, —NO$_2$, —N$_3$, optionally substituted alkyl, —OR$^{7A}$, —N(R$^{7B}$)$_2$, or optionally substituted acyl;

$R^{7A}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and $R^{7B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{7B}$ taken together with the intervening atoms form optionally substituted heterocyclyl.

$R^8$ is hydrogen, halogen, —CN, —NO$_2$, —N$_3$, optionally substituted alkyl, —OR$^{8A}$, —N(R$^{8B}$)$_2$, or optionally substituted acyl;

R[8A] is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of R[8B] is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two R[8B] taken together with the intervening atoms to form optionally substituted heterocyclyl; and R[9] is hydrogen, optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted acyl, —OR[2] or —N(R[9B])$_2$;

R[2] is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and each instance of R[9B] is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two R[9B] taken together with the intervening atoms to form optionally substituted heterocyclyl.

In certain embodiments, n is 1, and the compound of Formula (IV) is of Formula (IV-a):

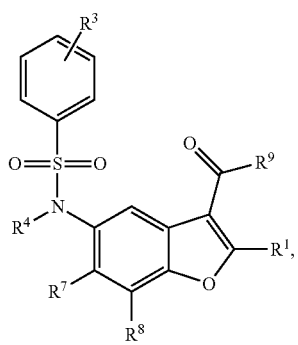

(IV-a)

or a pharmaceutically acceptable salt thereof.

In certain embodiments, n is 1, and the compound of Formula (IV) is of one of the following formulae:

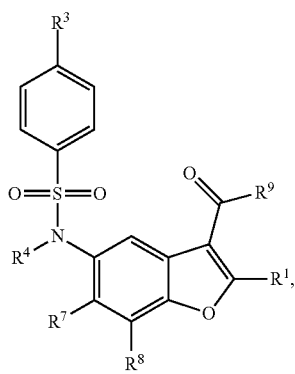

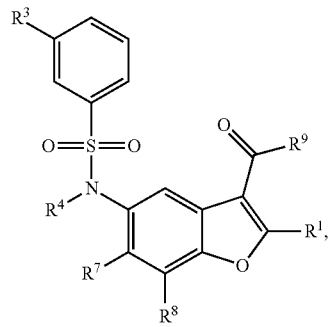

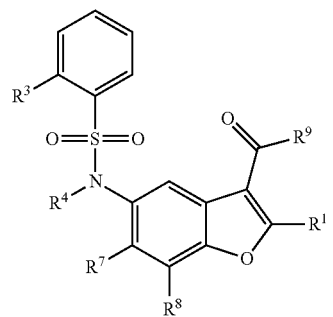

or a pharmaceutically acceptable salt thereof.

In certain embodiments, n is 2, and the compound of Formula (IV) is of one of the following formulae:

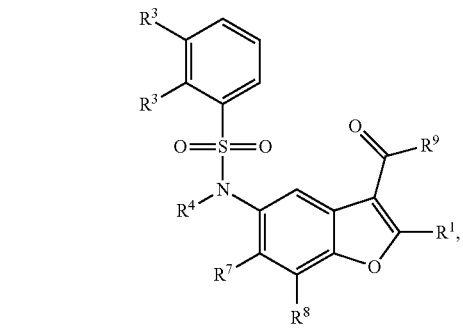

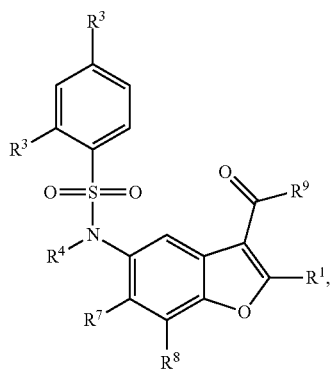

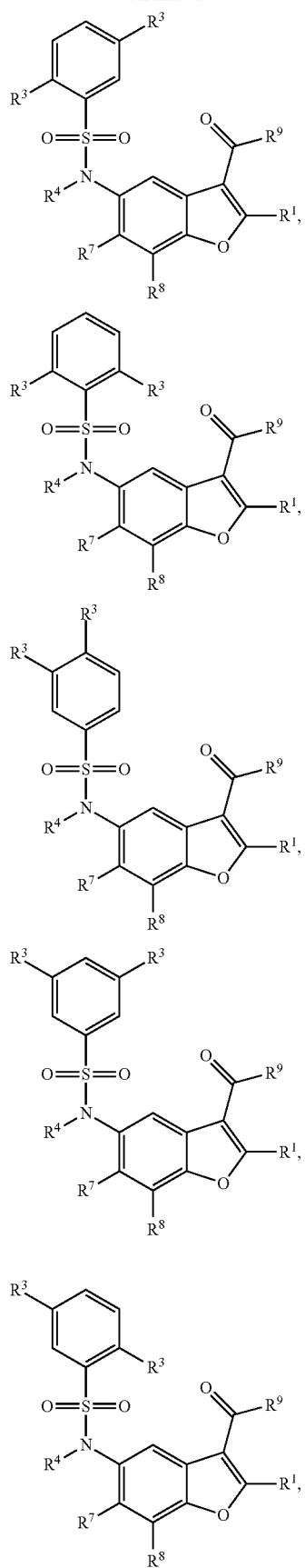
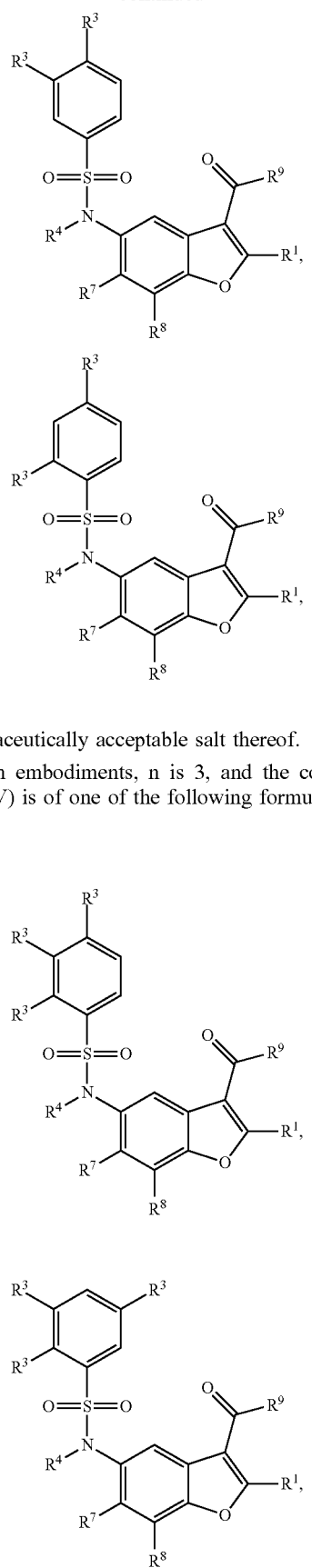
or a pharmaceutically acceptable salt thereof.
In certain embodiments, n is 3, and the compound of Formula (IV) is of one of the following formulae:

123
-continued
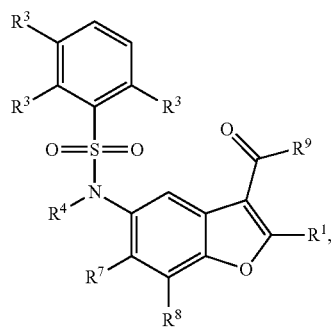
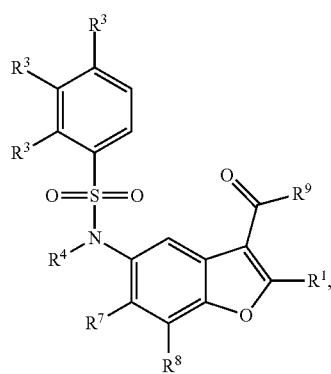
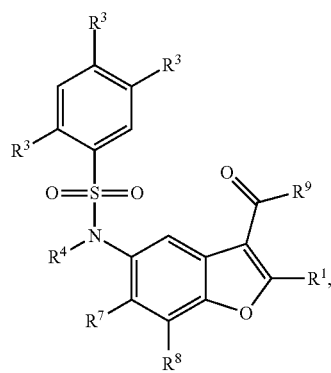
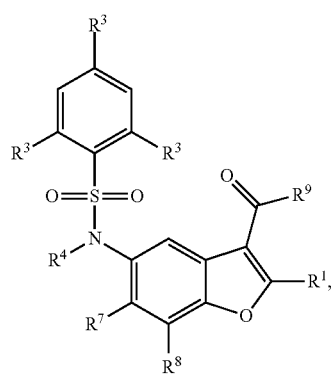
124
-continued
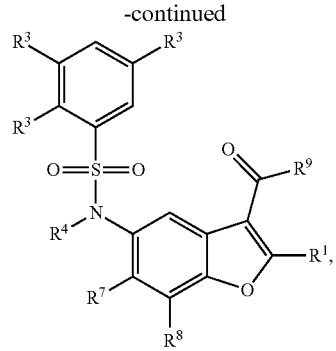
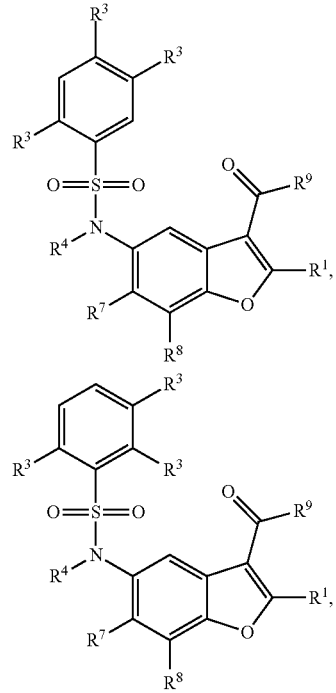
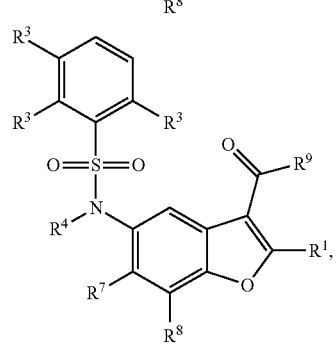
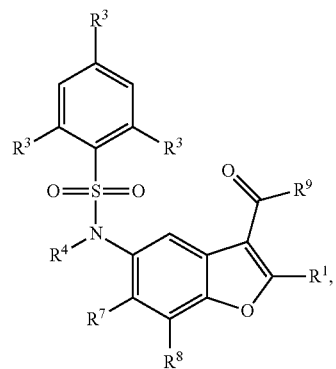

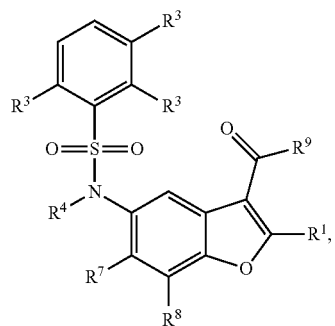
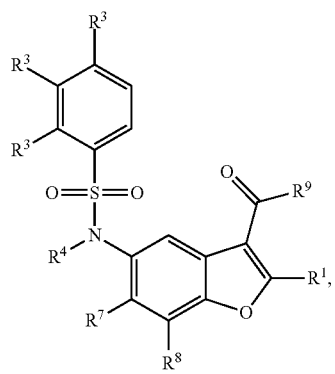
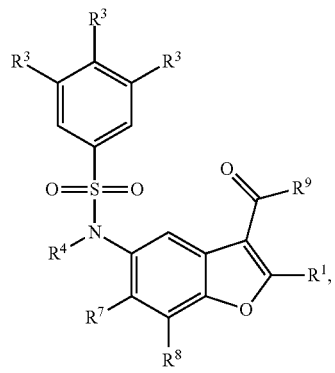
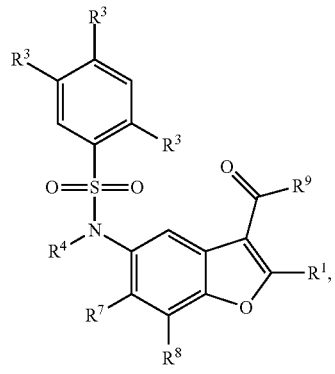
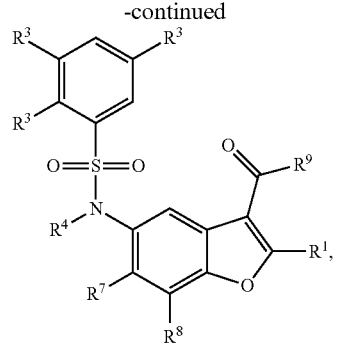
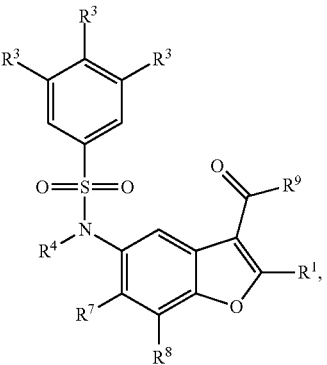
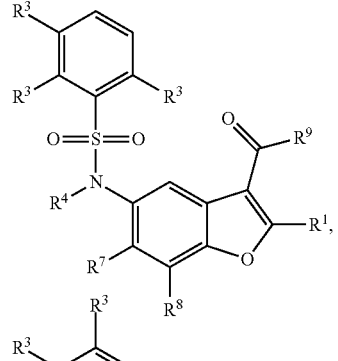
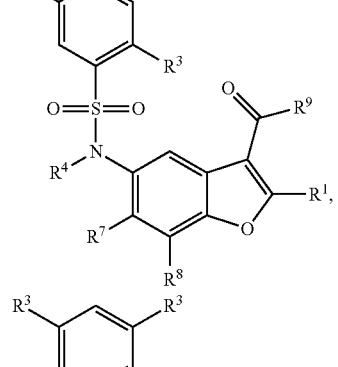
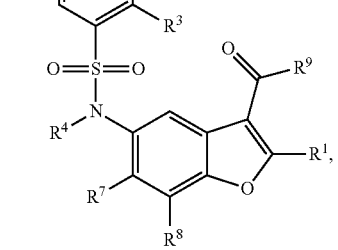
or a pharmaceutically acceptable salt thereof.

In certain embodiments, n is 4, and the compound of Formula (IV) is of one of the following formulae:

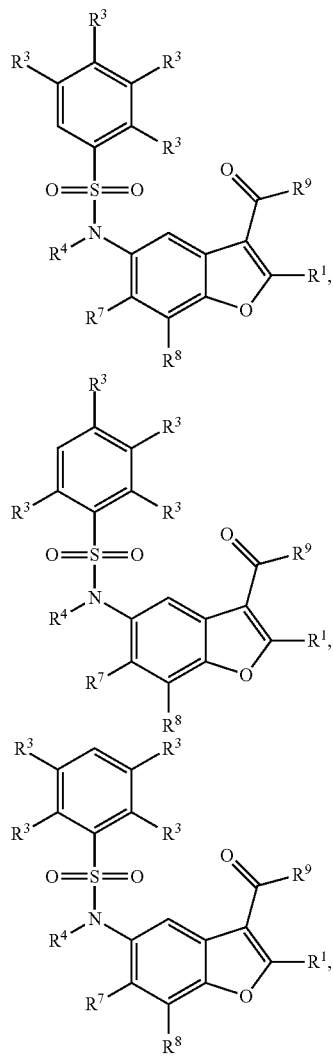

or a pharmaceutically acceptable salt thereof.

In certain embodiments, n is 5, and the compound of Formula (IV) is of the following formula:

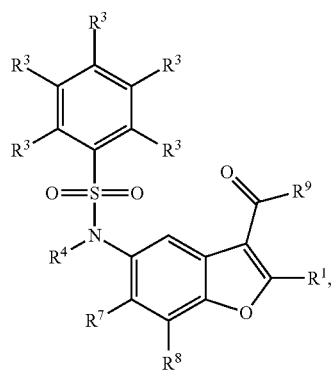

or a pharmaceutically acceptable salt thereof.

In certain embodiments, a compound of Formula (IV) is of the following formula:

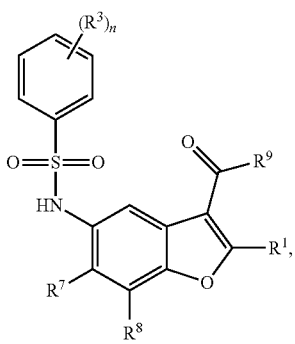

or a pharmaceutically acceptable salt thereof.

In certain embodiments, a compound of Formula (IV) is of the following formula:

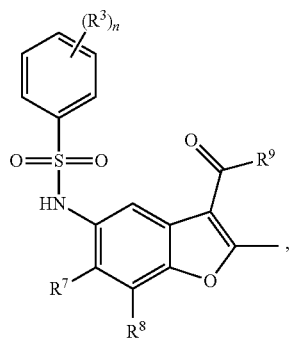

or a pharmaceutically acceptable salt thereof.

In certain embodiments, a compound of Formula (IV) is of the following formula:

or a pharmaceutically acceptable salt thereof.

In certain embodiments, a compound of Formula (IV) is of the following formula:

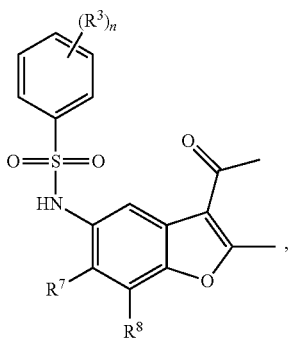

or a pharmaceutically acceptable salt thereof.

In certain embodiments, a compound of Formula (IV) is of the following formula:

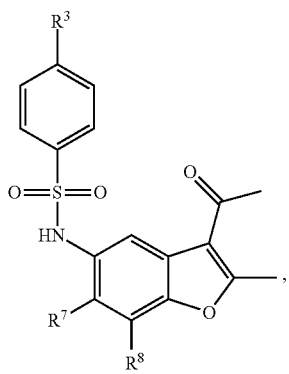

or a pharmaceutically acceptable salt thereof.

In certain embodiments, a compound of Formula (IV) is of the following formula:

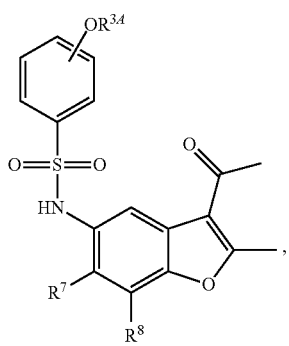

or a pharmaceutically acceptable salt thereof.

In certain embodiments, a compound of Formula (IV) is of the following formula:

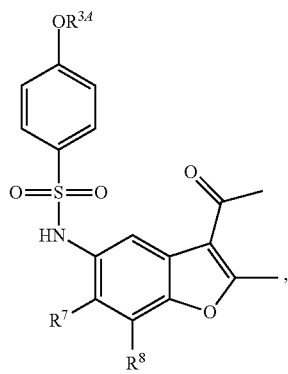

or a pharmaceutically acceptable salt thereof.

Examples of compounds of Formula (IV) include the following:

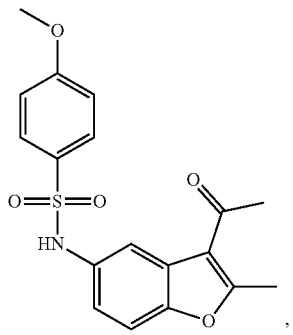

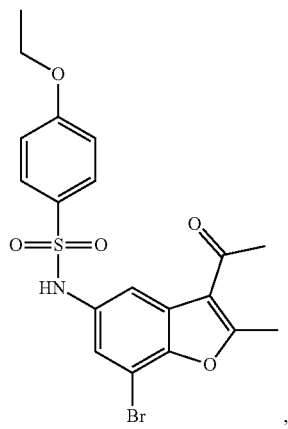

and pharmaceutically acceptable salts thereof.

As described herein, the invention provides methods of using compounds of Formula (III), or pharmaceutically acceptable salts, solvates, hydrates, polymorphs, co-crystals, tautomers, stereoisomers, isotopically labeled derivatives, and prodrugs thereof, and pharmaceutical compositions thereof, for the treatment and/or prevention of proliferative diseases. Provided herein are compounds of Formula (III):

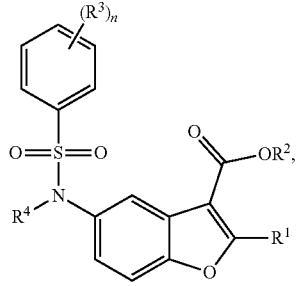

(III)

and pharmaceutically acceptable salts thereof, wherein:

R$^1$ is hydrogen, halogen, or optionally substituted alkyl;

each instance of R$^3$ is independently halogen, —CN, —NO$_2$, —N$_3$, optionally substituted alkyl, —OR$^{3A}$, —N(R$^{3B}$)$_2$, or optionally substituted acyl;

n is 1, 2, 3, 4, or 5;

R$^4$ is hydrogen, optionally substituted alkyl, or a nitrogen protecting group;

each of R$^2$ and R$^{3A}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and R$^{3B}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two R$^{3B}$ are taken together with the intervening atoms to form optionally substituted heterocyclyl.

In certain embodiments, n is 1, and the compound of Formula (III) is of Formula (III-a):

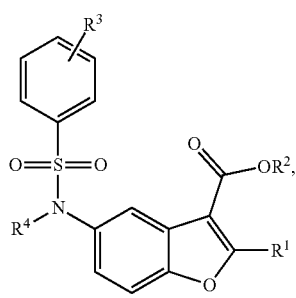

(III-a)

or a pharmaceutically acceptable salt thereof.

In certain embodiments, n is 1, and the compound of Formula (III) is of Formula (I-b):

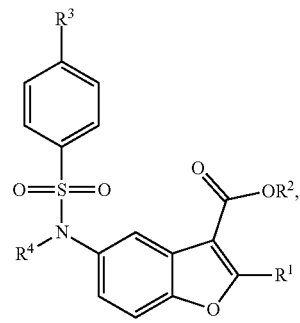

(III-b)

or a pharmaceutically acceptable salt thereof.

In certain embodiments, n is 1, and the compound of Formula (III) is of Formula (III-c):

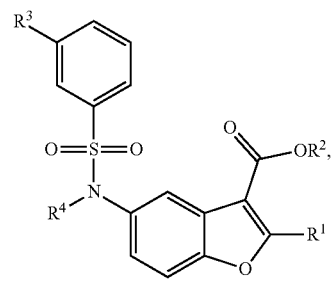

(III-c)

In certain embodiments, n is 1, and the compound of Formula (III) is of Formula (III-d):

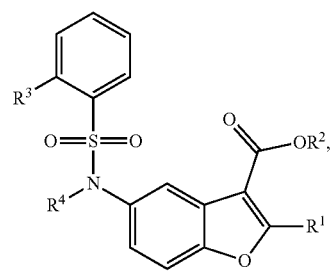

(III-d)

or a pharmaceutically acceptable salt thereof.

In certain embodiments, n is 2, and the compound of Formula (III) is of the formula:

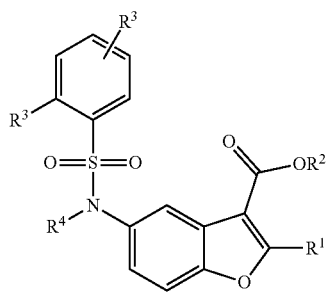

or a pharmaceutically acceptable salt thereof.

In certain embodiments, n is 2, and the compound of Formula (III) is of one of the following formulae:

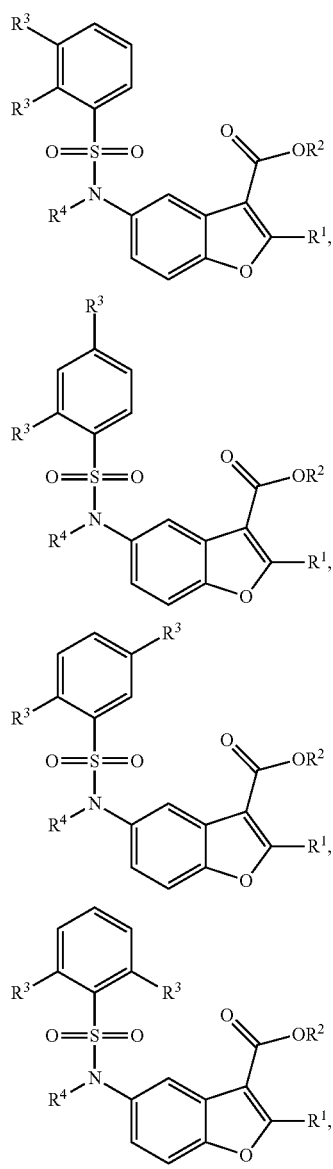

or a pharmaceutically acceptable salt thereof.

In certain embodiments, n is 2, and the compound of Formula (III) is of the formula:

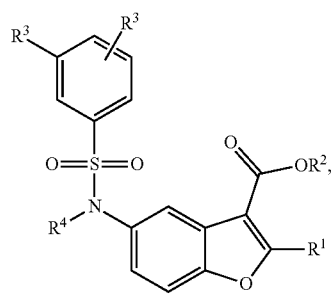

or a pharmaceutically acceptable salt thereof.

In certain embodiments, n is 2, and the compound of Formula (III) is of one of the following formulae:

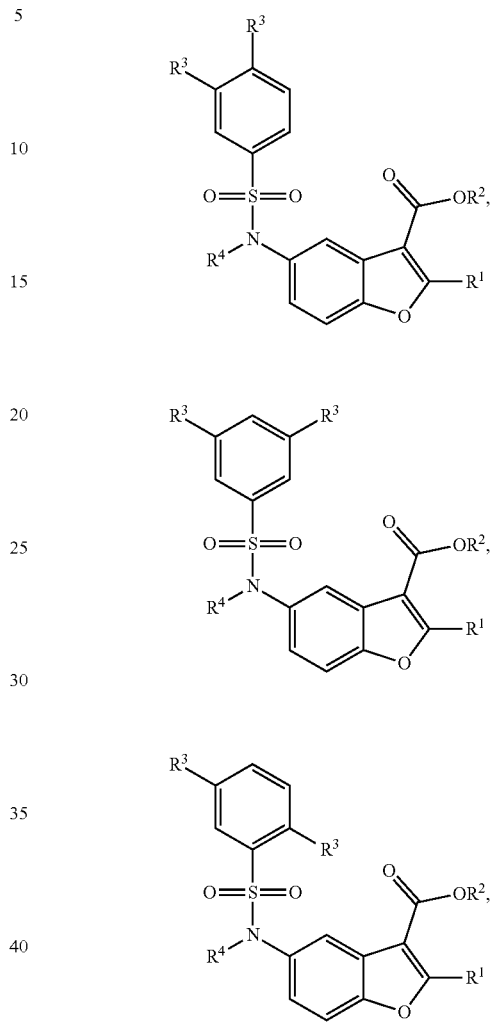

or a pharmaceutically acceptable salt thereof.

In certain embodiments, n is 2, and the compound of Formula (III) is of the formula:

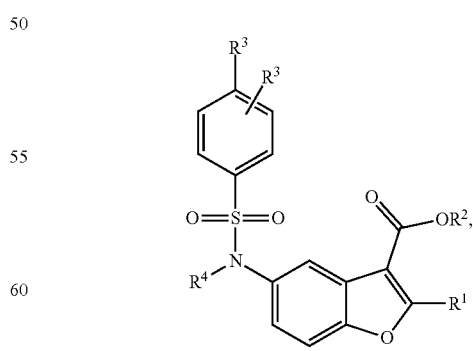

or a pharmaceutically acceptable salt thereof.

In certain embodiments, n is 2, and the compound of Formula (III) is of one of the following formulae:

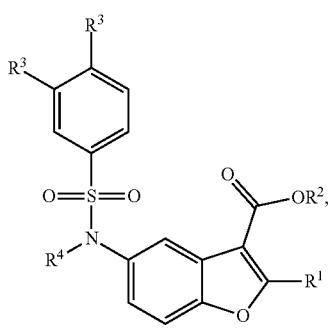

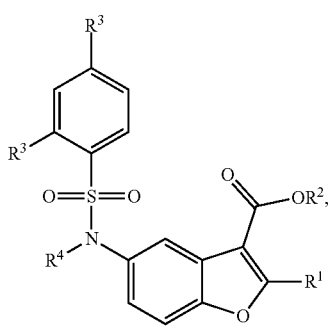

or a pharmaceutically acceptable salt thereof.

In certain embodiments, n is 3, and the compound of Formula (III) is of the formula:

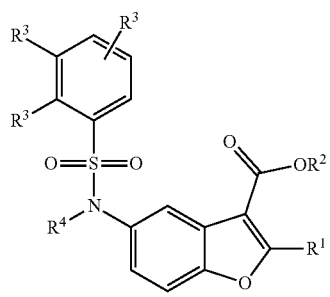

or a pharmaceutically acceptable salt thereof.

In certain embodiments, n is 3, and the compound of Formula (III) is of one of following formulae:

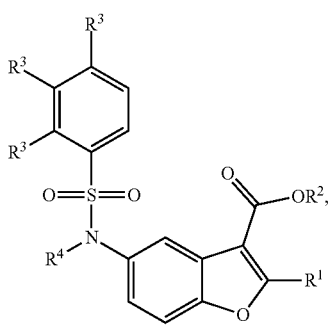

-continued

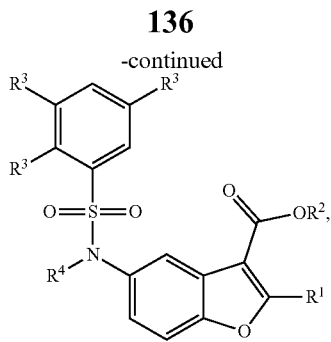

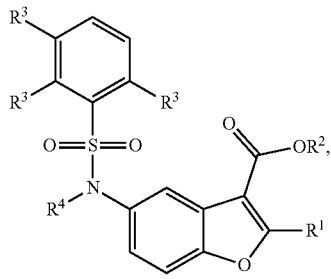

or a pharmaceutically acceptable salt thereof.

In certain embodiments, n is 3, and the compound of Formula (III) is of the formula:

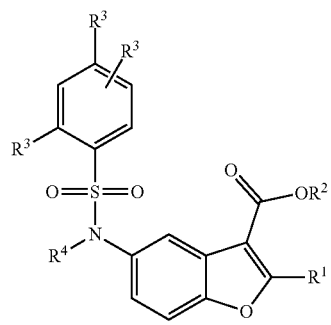

or a pharmaceutically acceptable salt thereof.

In certain embodiments, n is 3, and the compound of Formula (III) is of one of following formulae:

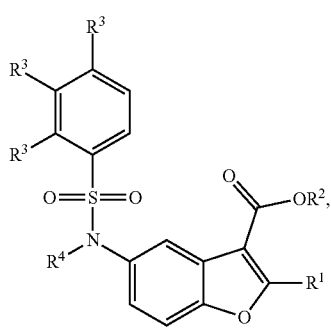

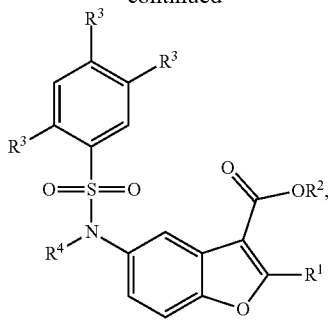

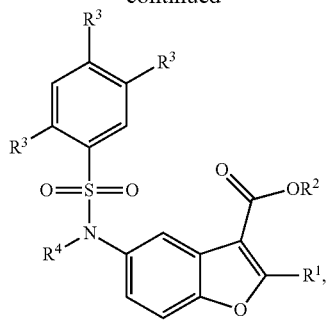

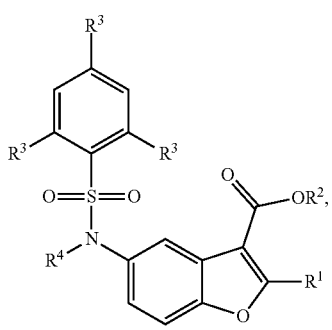

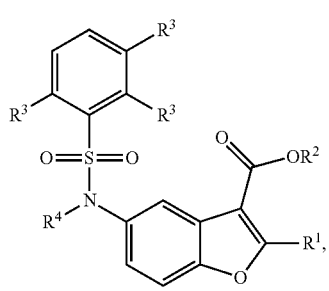

or a pharmaceutically acceptable salt thereof.

In certain embodiments, n is 3, and the compound of Formula (III) is of the formula:

or a pharmaceutically acceptable salt thereof.

In certain embodiments, n is 3, and the compound of Formula (III) is of the formula:

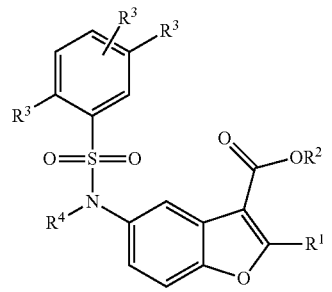

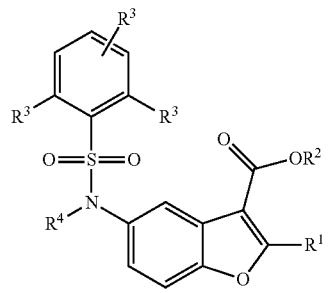

or a pharmaceutically acceptable salt thereof.

In certain embodiments, n is 3, and the compound of Formula (III) is of one of following formulae:

or a pharmaceutically acceptable salt thereof.

In certain embodiments, n is 3, and the compound of Formula (III) is of one of following formulae:

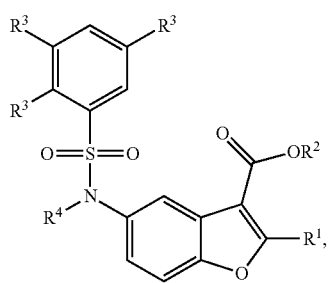

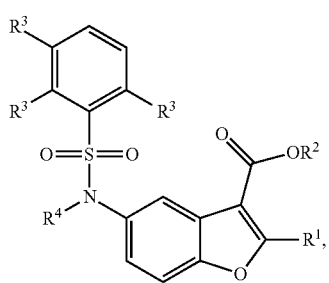

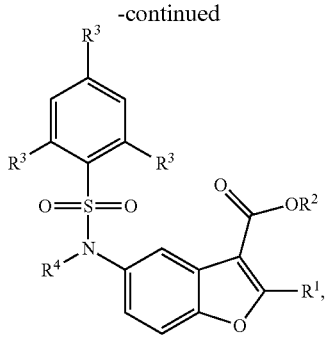

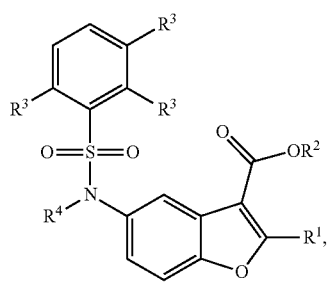

or a pharmaceutically acceptable salt thereof.

In certain embodiments, n is 3, and the compound of Formula (III) is of the formula:

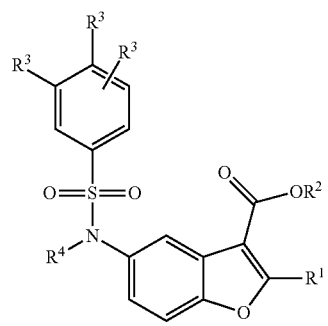

or a pharmaceutically acceptable salt thereof.

In certain embodiments, n is 3, and the compound of Formula (III) is of one of following formulae:

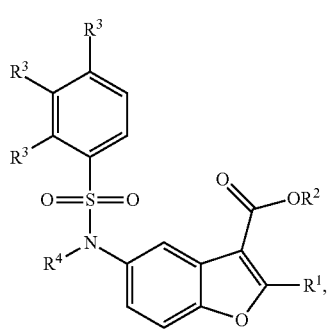

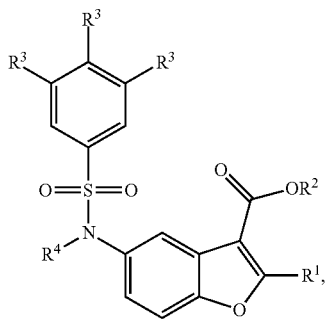

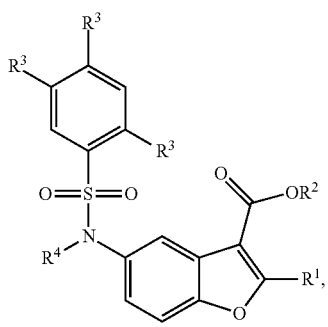

or a pharmaceutically acceptable salt thereof.

In certain embodiments, n is 3, and the compound of Formula (III) is of the formula:

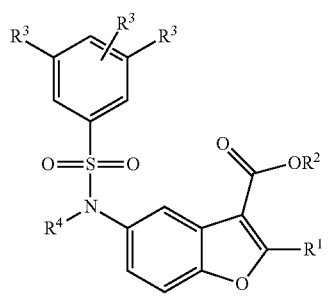

or a pharmaceutically acceptable salt thereof.

In certain embodiments, n is 3, and the compound of Formula (III) is of one of following formulae:

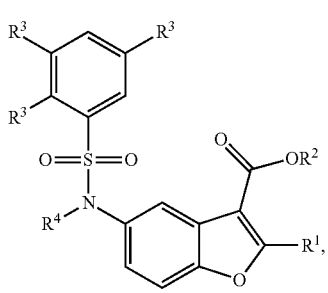

-continued

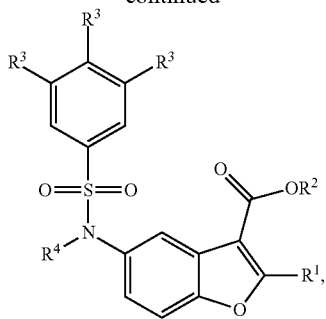

or a pharmaceutically acceptable salt thereof.

In certain embodiments, n is 3, and the compound of Formula (III) is of the formula:

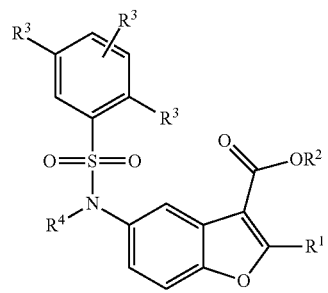

or a pharmaceutically acceptable salt thereof.

In certain embodiments, n is 3, and the compound of Formula (III) is of one of following formulae:

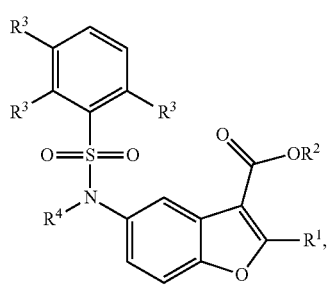

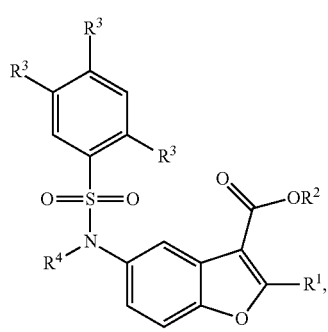

-continued

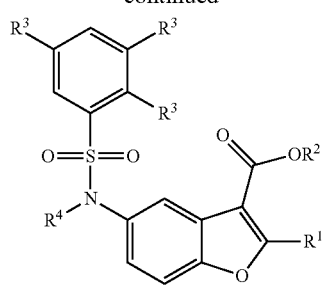

or a pharmaceutically acceptable salt thereof.

In certain embodiments, n is 4, and the compound of Formula (III) is of one of the following formulae:

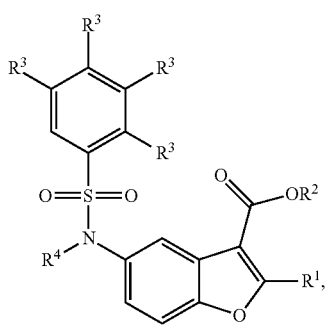

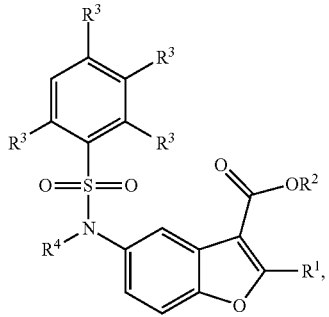

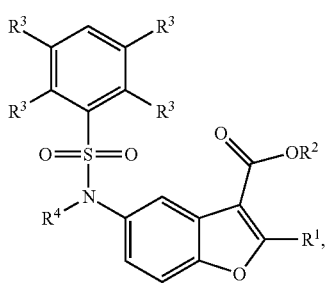

or a pharmaceutically acceptable salt thereof.

In certain embodiments, n is 5, and the compound of Formula (III) is of the following formula:

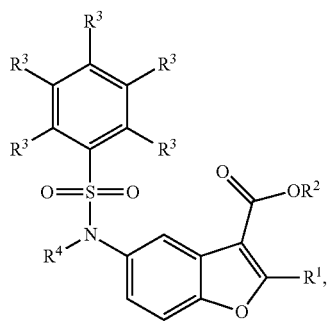

or a pharmaceutically acceptable salt thereof. In certain embodiments, the compound of Formula (III) is of the following formula:

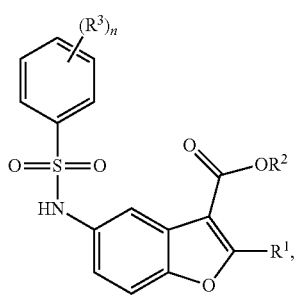

or a pharmaceutically acceptable salt thereof.

In certain embodiments, the compound of Formula (III) is of one of the following formulae:

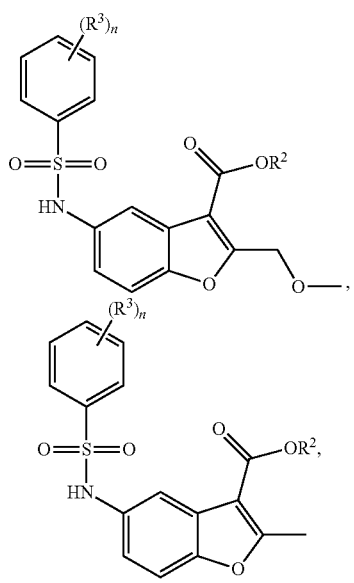

or a pharmaceutically acceptable salt thereof.

In certain embodiments, the compound of Formula (III) is of one of the following formulae:

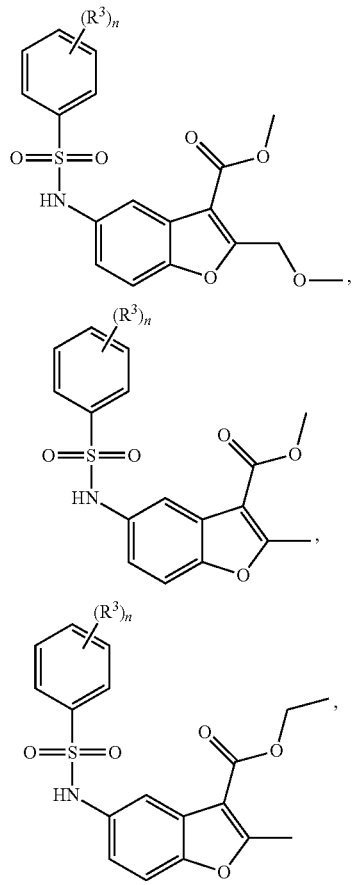

or a pharmaceutically acceptable salt thereof.

In certain embodiments, the compound of Formula (III) is of one of the following formulae:

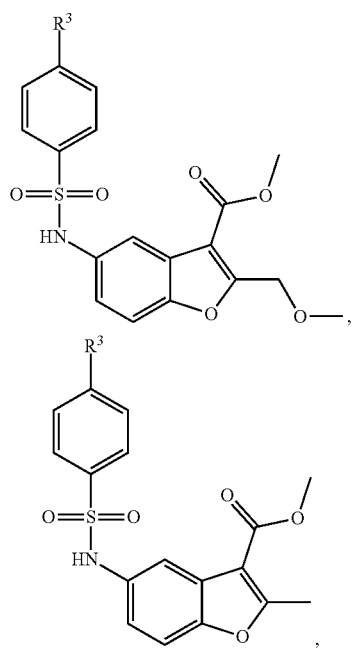

-continued

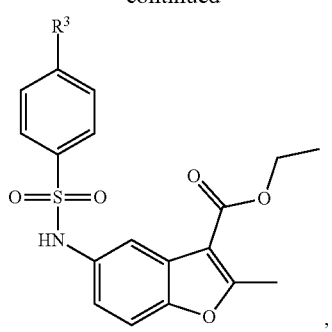

or a pharmaceutically acceptable salt thereof.

In certain embodiments, the compound of Formula (III) is of one of the following formulae:

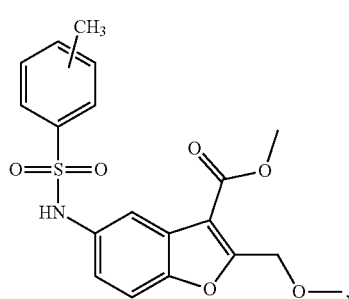

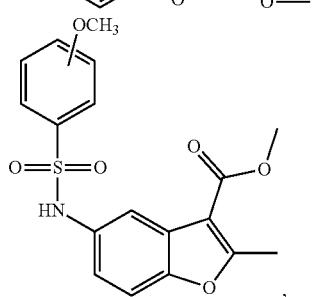

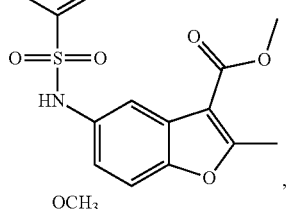

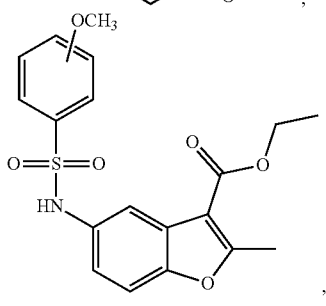

or a pharmaceutically acceptable salt thereof.

In certain embodiments, the compound of Formula (III) is of one of the following formulae:

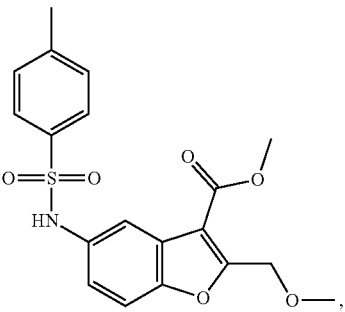

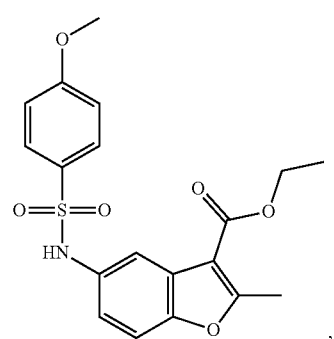

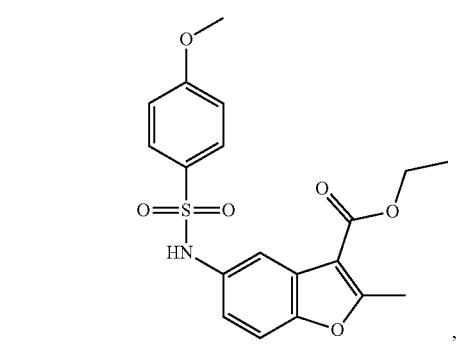

or a pharmaceutically acceptable salt thereof.

In certain embodiments, the compound of Formula (III) is of the following formula:

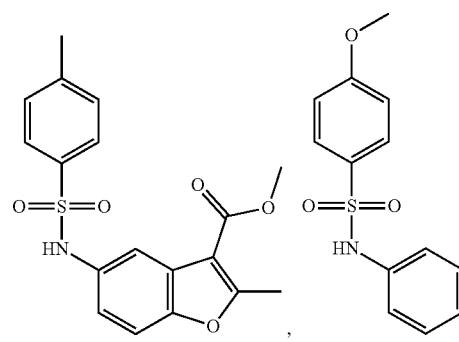

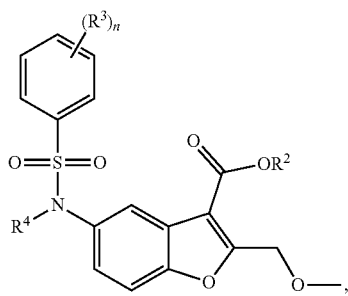

or a pharmaceutically acceptable salt thereof.

In certain embodiments, the compound of Formula (III) is of one of the following formulae:
or a pharmaceutically acceptable salt thereof.

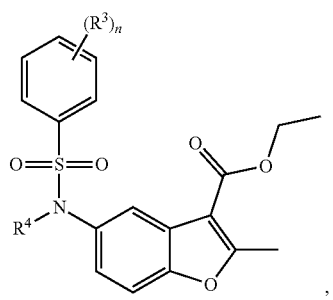

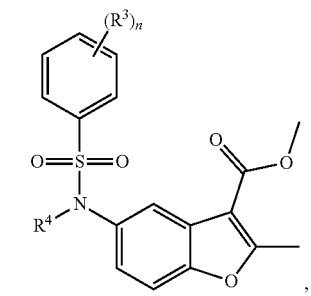

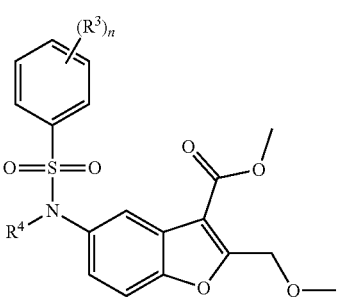

In certain embodiments, the compound of Formula (III) is of one of the following formulae:

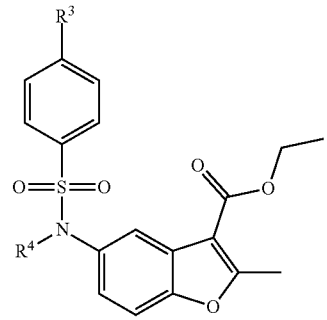

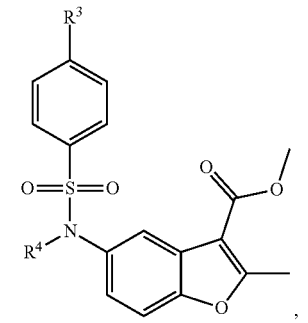

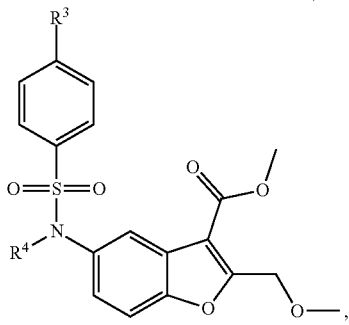 [SMILES: COCc1oc2ccc(NS(=O)(=O)c3ccc(OC)cc3)cc2c1C(=O)OC]

or a pharmaceutically acceptable salt thereof.

In certain embodiments, the compound of Formula (III) is of one of the following formulae:

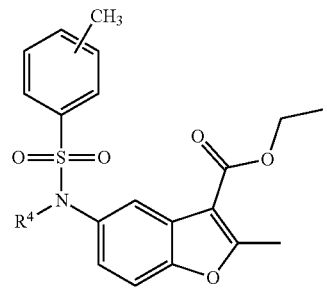

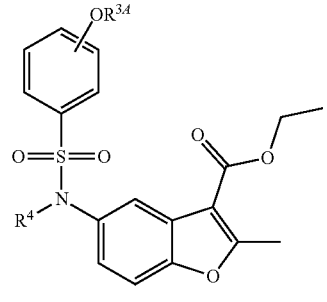

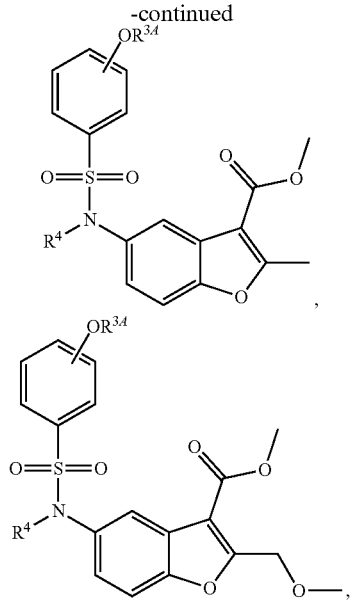
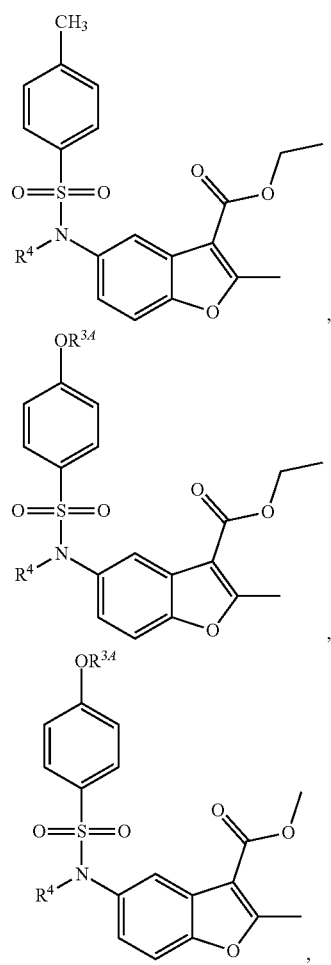
or a pharmaceutically acceptable salt thereof.
In certain embodiments, the compound of Formula (III) is of one of the following formulae:
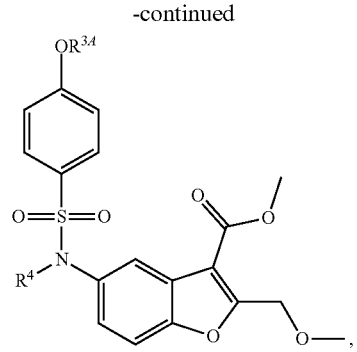
or a pharmaceutically acceptable salt thereof.
In certain embodiments, the compound of Formula (III) if of one of the following formulae:
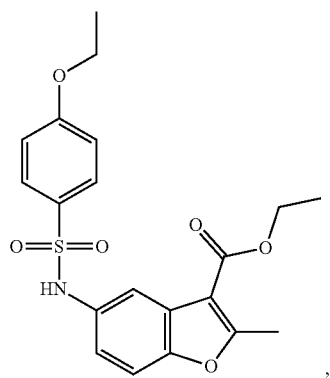

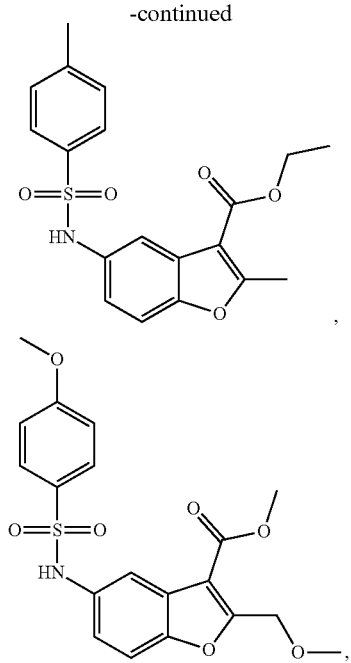

, or a pharmaceutically acceptable salt thereof.

Formula (III) includes substituents $R^1$, $R^2$, $R^3$, and $R^4$; and variable n. In certain embodiments, n is 1, and $R^3$ is optionally substituted $C_{1-6}$ alkyl. In certain embodiments, n is 1 and $R^3$ is unsubstituted $C_{1-6}$ alkyl. In certain embodiments, n is 1 and $R^3$ is optionally substituted $C_{1-3}$ alkyl. In certain embodiments, n is 1 and $R^3$ is unsubstituted $C_{1-3}$ alkyl. In certain embodiments, n is 1 and $R^3$ is methyl, ethyl, n-propyl, or iso-propyl. In certain embodiments, n is 1 and $R^3$ is methyl. In certain embodiments, n is 1; $R^3$ is methyl; and $R^3$ is para to the point of attachment of the sulfonamide group on the benzenoid ring. In certain embodiments, n is 1 and $R^3$ is —$OR^{3A}$ and $R^{3A}$ is as defined herein. In certain embodiments, n is 1; $R^3$ is —$OR^{3A}$; and $R^{3A}$ is optionally substituted alkyl. In certain embodiments, n is 1; $R^3$ is —$OR^{3A}$; and $R^{3A}$ is optionally substituted $C_{1-6}$ alkyl. In certain embodiments, n is 1; $R^3$ is —$OR^{3A}$; and $R^{3A}$ is unsubstituted $C_{1-6}$ alkyl. In certain embodiments, n is 1; $R^3$ is —$OR^{3A}$; and $R^{3A}$ is optionally substituted $C_{1-3}$ alkyl. In certain embodiments, n is 1; $R^3$ is $OR^{3A}$; and $R^{3A}$ is unsubstituted $C_{1-3}$ alkyl. In certain embodiments, n is 1 and $R^3$ is —$OCH_3$. In certain embodiments, n is 1; $R^3$ is —$OCH_3$; and $R^3$ is para to the point of attachment of the sulfonamide group on the benzenoid ring. In certain embodiments, n is 1 and $R^3$ is —OEt. In certain embodiments, n is 1 and $R^3$ is —OPr. In certain embodiments, n is 1 and $R^3$ is —OPr or —$O^iPr$. In certain embodiments, n is 1; $R^3$ is —$OR^{3A}$; and $R^{3A}$ is substituted $C_{1-6}$ alkyl.

In certain embodiments, $R^1$ is optionally substituted alkyl; n is 1; and $R^3$ is halogen, —CN, —$NO_2$, —$N_3$, optionally substituted alkyl, —$OR^{3A}$, —$N(R^{3B})_2$, or optionally substituted acyl. In certain embodiments, $R^1$ is optionally substituted $C_{1-6}$ alkyl; n is 1; and $R^3$ is optionally substituted $C_{1-6}$ alkyl. In certain embodiments, $R^1$ is optionally substituted $C_{1-6}$ alkyl; n is 1; $R^3$ is optionally substituted $C_{1-6}$ alkyl; and $R^3$ is para to the point of attachment of the sulfonamide group to the benzenoid ring. In certain embodiments, $R^1$ is unsubstituted $C_{1-6}$ alkyl; n is 1; and $R^3$ is unsubstituted $C_{1-6}$ alkyl. In certain embodiments, $R^1$ is optionally substituted $C_{1-3}$ alkyl; n is 1; and $R^3$ is optionally substituted $C_{1-3}$ alkyl. In certain embodiments, $R^1$ is unsubstituted $C_{1-3}$ alkyl; n is 1; and $R^3$ is unsubstituted $C_{1-3}$ alkyl. In certain embodiments, $R^1$ is methyl, ethyl, n-propyl, or iso-propyl; n is 1; and $R^3$ is methyl, ethyl, n-propyl, or iso-propyl. In certain embodiments, $R^1$ is methyl, ethyl, n-propyl, or iso-propyl; n is 1; $R^3$ is methyl, ethyl, n-propyl, or iso-propyl; $R^3$ is para to the point of attachment of the sulfonamide group to the benzenoid ring. In certain embodiments, n is 1 and $R^3$ is methyl. In certain embodiments, $R^1$ is methyl; n is 1; and $R^3$ is methyl.

In certain embodiments, $R^1$ is optionally substituted alkyl; n is 1; $R^3$ is —$OR^{3A}$; and $R^{3A}$ is as defined herein. In certain embodiments, $R^1$ is optionally substituted alkyl; n is 1; $R^3$ is —$OR^{3A}$; and $R^{3A}$ is optionally substituted alkyl. In certain embodiments, $R^1$ is optionally substituted $C_{1-6}$ alkyl; n is 1; $R^3$ is —$OR^{3A}$; and $R^{3A}$ is optionally substituted $C_{1-6}$ alkyl. In certain embodiments, $R^1$ is optionally substituted $C_{1-6}$ alkyl; n is 1; $R^3$ is —$OR^{3A}$; $R^{3A}$ is optionally substituted $C_{1-6}$ alkyl; and $R^3$ is para to the point of attachment of the sulfonamide group to the benzenoid ring. In certain embodiments, $R^1$ is unsubstituted $C_{1-6}$ alkyl; n is 1; $R^3$ is —$OR^{3A}$; and $R^{3A}$ is unsubstituted $C_{1-6}$ alkyl. In certain embodiments, $R^1$ is optionally substituted $C_{1-3}$ alkyl; n is 1; $R^3$ is —$OR^{3A}$; and $R^{3A}$ is optionally substituted $C_{1-3}$ alkyl. In certain embodiments, $R^1$ is unsubstituted $C_{1-3}$ alkyl; n is 1; $R^3$ is —$OR^{3A}$; and $R^{3A}$ is unsubstituted $C_{1-3}$ alkyl. In certain embodiments, $R^1$ is methyl, ethyl, n-propyl, or iso-propyl; n is 1; $R^3$ is —$OR^{3A}$; and $R^{3A}$ is methyl, ethyl, n-propyl, or iso-propyl. In certain embodiments, $R^1$ is methyl, ethyl, n-propyl, or iso-propyl; n is 1; $R^3$ is —$OR^{3A}$; $R^{3A}$ is methyl, ethyl, n-propyl, or iso-propyl; and $R^3$ is para to the point of attachment of the sulfonamide group to the benzenoid ring. In certain embodiments, n is 1; $R^3$ is —$OCH_3$. In certain embodiments, $R^1$ is methyl; n is 1; and $R^3$ is —$OCH_3$.

In certain embodiments, $R^1$ is alkyl substituted with one instance of —O—$C_{1-6}$alkyl; n is 1; and $R^3$ is halogen, —CN, —$NO_2$, —$N_3$, optionally substituted alkyl, —$OR^{3A}$, —$N(R^{3B})_2$, or optionally substituted acyl. In certain embodiments, $R^1$ is $C_{1-6}$alkyl substituted with one instance of —O—$C_{1-6}$alkyl; n is 1; and $R^3$ is optionally substituted $C_{1-6}$ alkyl. In certain embodiments, $R^1$ is $C_{1-6}$alkyl substituted with one instance of —O—$C_{1-6}$alkyl; n is 1; $R^3$ is optionally substituted $C_{1-6}$ alkyl; and $R^3$ is para to the point of attachment of the sulfonamide group to the benzenoid ring. In certain embodiments, $R^1$ is —$C_{1-6}$alkyl-O—$C_{1-6}$alkyl; n is 1; and $R^3$ is unsubstituted $C_{1-6}$ alkyl. In certain embodiments, $R^1$ is —$C_{1-3}$alkyl-O—$C_{1-3}$alkyl; n is 1; and $R^3$ is optionally substituted $C_{1-3}$ alkyl. In certain embodiments, $R^1$ is —$C_{1-3}$alkyl-O—$C_{1-3}$alkyl; n is 1; and $R^3$ is unsubstituted $C_{1-3}$ alkyl. In certain embodiments, $R^1$ is —$C_{1-3}$alkyl-O—$C_{1-3}$alkyl; n is 1; and $R^3$ is methyl, ethyl, n-propyl, or iso-propyl. In certain embodiments, $R^1$ is —$C_{1-3}$alkyl-O—$C_{1-3}$alkyl; n is 1; $R^3$ is methyl, ethyl, n-propyl, or iso-propyl; $R^3$ is para to the point of attachment of the sulfonamide group to the benzenoid ring. In certain embodiments, $R^1$ is —$CH_2$—O—$CH_3$; n is 1; and $R^3$ is methyl.

In certain embodiments, $R^1$ is optionally substituted alkyl; $R^2$ is optionally substituted alkyl; n is 1; and $R^3$ is —$OR^{3A}$ and $R^{3A}$ is as defined herein. In certain embodiments, $R^1$ is optionally substituted alkyl; $R^2$ is optionally substituted alkyl; n is 1; $R^3$ is —$OR^{3A}$; and $R^{3A}$ is optionally substituted alkyl. In certain embodiments, $R^1$ is optionally substituted $C_{1-6}$ alkyl; $R^2$ is optionally substituted $C_{1-6}$ alkyl; n is 1; $R^3$ is —$OR^{3A}$; and $R^{3A}$ is optionally substituted $C_{1-6}$ alkyl. In certain embodiments, $R^1$ is optionally substituted $C_{1-6}$ alkyl; $R^2$ is optionally substituted $C_{1-6}$ alkyl; n is 1; $R^3$ is —$OR^{3A}$; $R^{3A}$ is optionally substituted $C_{1-6}$ alkyl; and $R^3$ is para to the point of attachment of the sulfonamide group to the benzenoid ring. In certain embodiments, $R^1$ is unsubstituted $C_{1-6}$ alkyl; $R^2$ is unsubstituted $C_{1-6}$ alkyl; n is 1; $R^3$ is —$OR^{3A}$; and $R^{3A}$ is unsubstituted $C_{1-6}$ alkyl. In certain embodiments, $R^1$ is optionally substituted $C_{1-3}$ alkyl; $R^2$ is optionally substituted $C_{1-3}$ alkyl; n is 1; $R^3$ is —$OR^{3A}$; and $R^{3A}$ is optionally substituted $C_{1-3}$ alkyl. In certain embodiments, $R^1$ is unsubstituted $C_{1-3}$ alkyl; $R^2$ is unsubstituted $C_{1-3}$ alkyl; n is 1; $R^3$ is —$OR^{3A}$; and $R^{3A}$ is unsubstituted $C_{1-3}$ alkyl. In certain embodiments, $R^1$ is methyl, ethyl, n-propyl, or iso-propyl; $R^2$ is methyl, ethyl, n-propyl, or iso-propyl; n is 1; $R^3$ is —$OR^{3A}$; and $R^{3A}$ is methyl, ethyl, n-propyl, or iso-propyl. In certain embodiments, $R^1$ is methyl, ethyl, n-propyl, or iso-propyl; $R^2$ is methyl, ethyl, n-propyl, or iso-propyl; n is 1; $R^3$ is —$OR^{3A}$; $R^{3A}$ is methyl, ethyl, n-propyl, or iso-propyl; and $R^3$ is para to the point of attachment of the sulfonamide group to the benzenoid ring. In certain embodiments, $R^1$ is unsubstituted $C_{1-3}$ alkyl; $R^2$ is methyl; n is 1; $R^3$ is —$OR^{3A}$; and $R^{3A}$ is unsubstituted $C_{1-3}$ alkyl. In certain embodiments, $R^1$ is unsubstituted $C_{1-3}$ alkyl; $R^2$ is ethyl; n is 1; $R^3$ is —$OR^{3A}$; and $R^{3A}$ is unsubstituted $C_{1-3}$ alkyl. In certain embodiments, $R^1$ is methyl; $R^2$ is unsubstituted $C_{1-3}$ alkyl; n is 1; and $R^3$ is —$OCH_3$.

In certain embodiments, $R^1$ is optionally substituted alkyl; $R^2$ is optionally substituted alkyl; n is 1; and $R^3$ is halogen, —CN, —$NO_2$, —$N_3$, optionally substituted alkyl, —$OR^{3A}$, —$N(R^{3B})_2$, or optionally substituted acyl. In certain embodiments, $R^1$ is optionally substituted $C_{1-6}$ alkyl; $R^2$ is optionally substituted $C_{1-6}$ alkyl; n is 1; and $R^3$ is optionally substituted $C_{1-6}$ alkyl. In certain embodiments, $R^1$ is optionally substituted $C_{1-6}$ alkyl; $R^2$ is optionally substituted $C_{1-6}$ alkyl; n is 1; $R^3$ is optionally substituted $C_{1-6}$ alkyl; and $R^3$ is para to the point of attachment of the sulfonamide group to the benzenoid ring. In certain embodiments, $R^1$ is unsubstituted $C_{1-6}$ alkyl; $R^2$ is unsubstituted $C_{1-6}$ alkyl; n is 1; and $R^3$ is unsubstituted $C_{1-6}$ alkyl. In certain embodiments, $R^1$ is optionally substituted $C_{1-3}$ alkyl; $R^2$ is optionally substituted $C_{1-3}$ alkyl; n is 1; and $R^3$ is optionally substituted $C_{1-3}$ alkyl. In certain embodiments, $R^1$ is unsubstituted $C_{1-3}$ alkyl; $R^2$ is unsubstituted $C_{1-3}$ alkyl; n is 1; and $R^3$ is unsubstituted $C_{1-3}$ alkyl. In certain embodiments, $R^1$ is methyl, ethyl, n-propyl, or iso-propyl; $R^2$ is methyl, ethyl, n-propyl, or iso-propyl; n is 1; and $R^3$ is methyl, ethyl, n-propyl, or iso-propyl. In certain embodiments, $R^1$ is methyl, ethyl, n-propyl, or iso-propyl; $R^2$ is methyl, ethyl, n-propyl, or iso-propyl; n is 1; $R^3$ is methyl, ethyl, n-propyl, or iso-propyl; and $R^3$ is para to the point of attachment of the sulfonamide group to the benzenoid ring. In certain embodiments, $R^1$ is methyl; $R^2$ is methyl; n is 1; and $R^3$ is methyl. In certain embodiments, $R^1$ is methyl; $R^2$ is ethyl; n is 1; and $R^3$ is methyl.

In certain embodiments, $R^1$ is alkyl substituted with one instance of —O—$C_{1-6}$alkyl; $R^2$ is optionally substituted alkyl; n is 1; and $R^3$ is halogen, —CN, —$NO_2$, —$N_3$, optionally substituted alkyl, —$OR^{3A}$, —$N(R^{3B})_2$, or optionally substituted acyl. In certain embodiments, $R^1$ is $C_{1-6}$alkyl substituted with one instance of —O—$C_{1-6}$alkyl; $R^2$ is optionally substituted $C_{1-6}$ alkyl; n is 1; and $R^3$ is optionally substituted $C_{1-6}$ alkyl. In certain embodiments, $R^1$ is $C_{1-6}$alkyl substituted with one instance of —O—$C_{1-6}$alkyl; $R^2$ is optionally substituted $C_{1-6}$ alkyl; n is 1; $R^3$ is optionally substituted $C_{1-6}$ alkyl; and $R^3$ is para to the point of attachment of the sulfonamide group to the benzenoid ring. In certain embodiments, $R^1$ is —$C_{1-6}$alkyl-O—$C_{1-6}$alkyl; n is 1; and $R^3$ is unsubstituted $C_{1-6}$ alkyl. In certain embodiments, $R^1$ is —$C_{1-3}$alkyl-O—$C_{1-3}$alkyl; $R^2$ is unsubstituted $C_{1-6}$ alkyl; n is 1; and $R^3$ is optionally substituted $C_{1-3}$ alkyl. In certain embodiments, $R^1$ is —$C_{1-3}$alkyl-O—$C_{1-3}$alkyl; $R^2$ is unsubstituted $C_{1-3}$ alkyl. In certain embodiments, $R^1$ is —$C_{1-3}$alkyl-O—$C_{1-3}$alkyl; $R^2$ is methyl, ethyl, n-propyl, or iso-propyl; n is 1; and $R^3$ is methyl, ethyl, n-propyl, or iso-propyl. In certain embodiments, $R^1$ is —$C_{1-3}$alkyl-O—$C_{1-3}$alkyl; $R^2$ is methyl, ethyl, n-propyl, or iso-propyl; n is 1; $R^3$ is methyl, ethyl, n-propyl, or iso-propyl; $R^3$ is para to the point of attachment of the sulfonamide group to the benzenoid ring. In certain embodiments, $R^1$ is —$CH_2$—O—$CH_3$; $R^2$ is methyl; n is 1; and $R^3$ is methyl. In certain embodiments, $R^1$ is —$CH_2$—O—$CH_3$; $R^2$ is ethyl; n is 1; and $R^3$ is methyl.

In some embodiments, a compound described herein (e.g., a compound of Formula (I), (II), (III), (IV), (V), or (VI)) is useful in treating a cancer. In some embodiments, a compound described herein is useful to delay the onset of, slow the progression of, or ameliorate the symptoms of cancer. In some embodiments, a compound described herein is administered in combination with another pharmaceutical agent to treat cancer.

In some embodiments, compounds described herein (e.g., compounds of Formulae (I), (II), (III), (IV), (V), and (VI)) are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/ leukemia, peripheral T-cell lymphoma (PTCL) (e.g., cutaneous T-cell lymphoma (CTCL) (e.g., mycosis fungiodes, Sezary syndroma), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, a compound described herein (e.g., a compound of Formula (I), (II), (III), (IV), (V), or (VI)) is useful in treating a hematologic cancer. In certain embodiments, the hematologic cancer is a leukemia. In certain embodiments, the leukemia is AML. In certain embodiments, the leukemia is CML. In certain embodiments, the leukemia is CLL. In certain embodiments, the hematologic cancer is a lymphoma. In certain embodiments, the hematologic cancer is multiple myeloma. In some embodiments, a compound described herein is useful in treating a solid tumor. In certain embodiments, the solid tumor is lung cancer, pancreatic cancer, breast cancer, prostate cancer, colon cancer, liver cancer, or cervical cancer. In some embodiments, a compound described herein is useful in treating lung cancer. In some embodiments, a compound described herein is useful in treating pancreatic cancer. In some embodiments, a compound described herein is useful in treating breast cancer. In some embodiments, a compound described herein is useful in treating prostate cancer. In some embodiments, a compound described herein is useful in treating colon cancer. In some embodiments, a compound described herein is useful in treating cervical cancer. In some embodiments, a compound described herein is useful in treating liver cancer. In some embodiments, a compound described herein is useful in treating hepatocellular carcinoma. In some embodiments, a compound described herein is useful in treating lung cancer. In some embodiments, a compound described herein is useful in treating small cell lung cancer. In some embodiments, a compound described herein is useful in treating non-small cell lung cancer.

In some embodiments, a compound described herein (e.g., a compound of Formula (I), (II), (III), (IV), (V), or (VI)) is useful in treating advanced staged cancer. In some embodiments, a compound described herein is useful in treating metastatic cancer. In some embodiments, a compound described herein is useful in treating metastatic hematologic cancer (e.g., leukemia, lymphoma, or myeloma). In some embodiments, a compound described herein is useful in treating a metastatic solid tumor (e.g., lung cancer, pancreatic cancer, breast cancer, prostate cancer, colon cancer, lung cancer, or cervical cancer). In some embodiments, a compound described herein is useful in treating mutant cancer. In some embodiments, a compound described herein is useful in treating RAS mutant cancer. In some embodiments, a compound described herein is useful in treating K-RAS mutant cancer. In some embodiments, a compound described herein is useful in treating K-RAS mutant lung cancer.

In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

The present invention also provides methods of inhibiting the activity of at least one BCL-2 family protein in a biological sample or a subject.

As used herein, "BCL-2" encompasses "BCL-2" genes and "BCL-2 family proteins" that regulate apoptosis mainly by regulating the outer mitochondrial membrane integrity (Czabotar et al., *Nat. Rev. Mol. Cell Biol.*, 2014, 15, 49-63). BCL-2 encompasses two classes: anti-apoptotic and pro-apoptotic. The BCL-2 anti-apoptotics (also called "BCL-2 pro-survival proteins") include BCL-2, BCL-w, BCL-$X_L$, MCL-1, A1 (BCL2A1) and BCL-B, all of which share up to four BH regions named BH1-4, and prevent cells from entering apoptosis. The BCL-2 pro-apoptotics can be further grouped into the multidomain pro-apoptotic and BH3-only proteins. The multidomain pro-apoptotic effectors, BAX and BAK, also contain four BH (BH1-4) regions and promote cell death by oligomerization-mediated mitochondria outer membrane permeabilization (MOMP). The BH3-only proteins share the BH3 region of sequence similarity. Members of this group include BID, BIM, BAD, BMF, BIK, PUMA, NOXA, HRK/DP5 (Harakiri), NIX, and BNIP3. The BH3 region is 16 to 25 amino acid residues long and some BH3 peptides can promote apoptosis when introduced into cells. The three groups of BCL-2 family proteins form a delicately balanced network of opposing functions that regulates the cell's fate. In certain embodiments, the BCL-2 is a BCL-2 anti-apoptotic. In certain embodiments, the BCL-2 anti-apoptotic is BCL-2, BCL-W, BCL-$X_L$, or MCL-1. In certain embodiments, the BCL-2 anti-apoptotic is MCL-1. In certain embodiments, the compounds described herein may interact with at least one anti-apoptotic protein member of the BCL-2 family, thereby enhancing apoptosis. In certain embodiments, the compounds described herein may interact with at least one anti-apoptotic protein member of the BCL-2 family and induce its degradation. In certain embodiments, the compounds described herein may interact with at least one pro-apoptotic protein member of the BCL-2 family, thereby enhancing apoptosis. More specifically, such pro-apoptotic member of the BCL-2 family may be any one of BAX, BAK, BNIP3, NIX, BID, NOXA, PUMA and BAD.

In certain embodiments, a compound described herein (e.g., a compound of Formula (I), (II), (III), (IV), (V), or (VI)) modulates the activity of at least one anti-apoptotic BCL-2 family member (e.g., by binding to the hydrophobic dimerization groove of at least one anti-apoptotic BCL-2 family member protein). In certain embodiments, the compounds described herein modulate MCL-1 activity by binding to the hydrophobic dimerization groove of MCL-1. In certain embodiments, the compounds described herein inhibit the activity of at least one anti-apoptotic BCL-2 family protein by binding to the hydrophobic dimerization groove of the BCL-2 protein. In certain embodiments, the compounds described herein inhibit the activity of at least one anti-apoptotic BCL-2 family protein by binding to the hydrophobic dimerization groove of the BCL-$X_L$ protein. In certain embodiments, the compounds described herein can act as NOXA mimetics. NOXA is a pro-apoptotic BH3-only member of the BCL-2 protein family and has been shown to be involved in p53-mediated apoptosis and specifically antagonize MCL-1. In certain embodiments, the compounds described herein mimic NOXA and bind to the hydrophotic dimerization groove of MCL-1 and induce apoptosis in MCL-1 addicted cancer cells. In certain embodiments, the compounds described herein induce the degradation of MCL-1 and thereby trigger apoptotis in MCL-1 addicted cancer cells.

In still another aspect, the present invention provides methods of inducing apoptosis of a cell in a biological sample or a subject.

In certain embodiments, the compounds described herein (e.g., a compound of Formula (I), (II), (III), (IV), (V), or (VI)) induce apoptosis of a cell by modulating at least one BCL-2 pathway. In certain embodiments, the compounds described herein induce apoptosis of a cell by modulating MCL-1 pathway. In certain embodiments, the compounds described herein induce apoptosis of a cell by inhibiting at least one BCL-2 pathway. In certain embodiments, the compounds described herein inhibit apoptosis of a cell by modulating MCL-1 pathway.

It should be further noted that by inhibiting the anti-apoptotic action of BCL-2 family proteins, the compounds induce or enhance apoptosis. In certain embodiments, the compounds as described herein may lead to an increase, enhancement, induction, or elevation in apoptosis of treated cells. In certain embodiments, such increase, induction, or elevation of apoptosis may be an increase by about 1% to 99.9%. In certain embodiments, such increase, induction, or elevation of apoptosis may be an increase by about 1% to about 95%. In certain embodiments, such increase, induction, or elevation of apoptosis may be an increase by about 5% to 90%. In certain embodiments, such increase, induction, or elevation of apoptosis may be an increase by about 10% to 85%. In certain embodiments, such increase, induction, or elevation of apoptosis may be an increase by about 15% to 80%. In certain embodiments, such increase, induction, or elevation of apoptosis may be an increase by about 20% to 75%. In certain embodiments, such increase, induction, or elevation of apoptosis may be an increase by about 25% to 70%. In certain embodiments, such increase, induction, or elevation of apoptosis may be an increase by about 30% to 65%. In certain embodiments, such increase, induction, or elevation of apoptosis may be an increase by about 35% to 60%. In certain embodiments, such increase, induction, or elevation of apoptosis may be an increase by about 40% to 55%. In certain embodiments, such increase, induction, or elevation of apoptosis may be an increase by about 45% to 50%. In certain embodiments, such increase, induction, or elevation of apoptosis may be an increase by about 5%, 10%, 15%, 20%, 25%, 30%, 35%, 40%, 45%, 50%, 55%, 60%, 65%, 70%, 75%, 80%, 85%, 90%, 95%, or 99.9%. In certain embodiments, such increase, induction, or elevation of apoptosis may be an increase by about 5%, 10%, 15%, 20%, 25%, 30%, 35%, 40%, 45%, 50%, 55%, 60%, 65%, 70%, 75%, 80%, 85%, 90%, 95%, or 99% as compared to untreated control.

The cell described herein may be an abnormal cell. The cell may be in vitro or in vivo. In certain embodiments, the cell is a dividing cell. In certain embodiments, the cell is a blood cell. In certain embodiments, the cell is a lymphocyte. In certain embodiments, the cell is a cancer cell. In certain embodiments, the cell is a leukemia cell. In certain embodiments, the cell is a melanoma cell. In certain embodiments, the cell is a multiple myeloma cell. In certain embodiments, the cell is a neoplastic cell. In certain embodiments, the cell is an endothelial cell. In certain embodiments, the cell is an immune cell.

In certain embodiments, the methods described herein include administering to a subject or contacting a biological sample with an effective amount of a compound of Formula (I), (II), (III), (IV), (V), or (VI), or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include administering to a subject or contacting a biological sample with an effective amount of a compound of Formula (I), (II), (III), (IV), (V), or (VI), or a pharmaceutically acceptable salt thereof, or a pharmaceutical composition thereof.

In certain embodiments, the compound is administered in combination with one or more additional pharmaceutical agents described herein. Exemplary additional therapeutically active agents include, but are not limited to, anti-proliferative agents, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins, etc. Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional pharmaceutical agent is an anti-proliferative agent. In certain embodiments, the additional pharmaceutical agent is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g., hydroxyurea and deferoxamine), uracil analogs (e.g. 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g. mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g. actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AGO 13736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SUI 1248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the additional anti-cancer agent is an inhibitor of BCL-2. In certain embodiments, the additional anti-cancer agent is an inhibitor of BCL-$X_L$. In certain embodiments, the additional anti-cancer agent is an inhibitor of an anti-apoptotic BCL-2 family protein. In certain embodiments, the additional anti-cancer agent is navitoclax, 4-[4-[[2-(4-Chlorophenyl)-5,5-dimethyl-1-cyclohexen-1-yl]methyl]-1-piperazinyl]-N-[[4-[(1R)-3-(4-morpholinyl)-1-[(phenylthio)methyl]propyl]amino]-3-[(trifluoromethyl)sulfonyl]phenyl]sulfonyl]benzamide (ABT-263), (R)-4-(4-((4'-chloro-[1,1'-biphenyl]-2-yl)methyl) piperazin-1-yl)-N-((4-((-4-(dimethylamino)-1-(phenylthio) butan-2-yl)amino)-3-nitrophenyl)sulfonyl)benzamide (ABT-737), venetoclax (ABT-199), 1,1',6,6',7,7'-hexahydroxy-5,5'-diisopropyl-3,3'-dimethyl-[2,2'-binaphthalene]-8,8'-dicarbaldehyde (AT-101), (Z)-2-(2-((3,5-dimethyl-1H-pyrrol-2-yl)methylene)-3-methoxy-2H-pyrrol-5-yl)-1H-indole methanesulfonate (GX15-070), 5-(2-isopropylbenzyl)-N-(4-(2-tert-butylphenylsulfonyl)phenyl)-2,3,4-trihydroxybenzamide (TW-37), Gossypol, (−)-epigallocatechin gallate, obatoclax mesylate, licochalcone A, HA14-1, EM20-25, nilotinib, YC137, 2-methoxy-antimycin A3, ABT-199, gambogic Acid, or nilotinib. In certain embodiments, the additional anti-cancer agent is an inhibitor of MCL-1. In certain embodiments, the additional anti-cancer agent is ABT-263. In certain embodiments, the additional anti-cancer agent is ABT-199.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

In certain embodiments, the method of the invention may further comprise an additional determination of the anti-apoptotic BCL-2 family levels in the affected subject, such diagnostic step comprise (a) determining the level of expression of at least one BCL-2 pro-survival protein in at least one biological sample of the subject to obtain an expression value. The next step (b) involves determining if the expression value obtained in step (a) is any one of, positive or negative with respect to a predetermined standard expression value or to an expression value of said MCL-1 in a control sample. It should be noted that a positive expression value of said MCL-1 may indicate that the examined subjects may display a beneficial effect in response to compounds that reduce MCL-1 levels, and therefore may be administered with the provided compounds of the invention.

Thus, in more specific embodiments, the invention further provides a method for treating and/or preventing an MCL-1 or other anti-apoptotic BCL-2 family protein over-expressing pathological disorder comprising the step of: First (a) determining the level of expression of at least one BCL-2 prosurvival protein in at least one biological sample of said subject to obtain an expression value. In the second step (b) determining if the expression value obtained in step (a) is any one of, positive or negative with respect to a predetermined standard expression value or to an expression value of said MCL-1 in a control sample. Finally, in step (c) administering to a subject displaying a positive expression value of MCL-1 as determined in step (b), a therapeutically effective amount of at least one compound as described herein.

EXAMPLES

These and other aspects of the present invention will be further appreciated upon consideration of the following Examples, which are intended to illustrate certain particular embodiments of the invention but are not intended to limit its scope, as defined by the claims.

Synthesis of Compounds

Compounds described herein can be prepared according to the example provided in Scheme 1. Scheme 1 shows the preparation of Compound 1 ("Mclin").

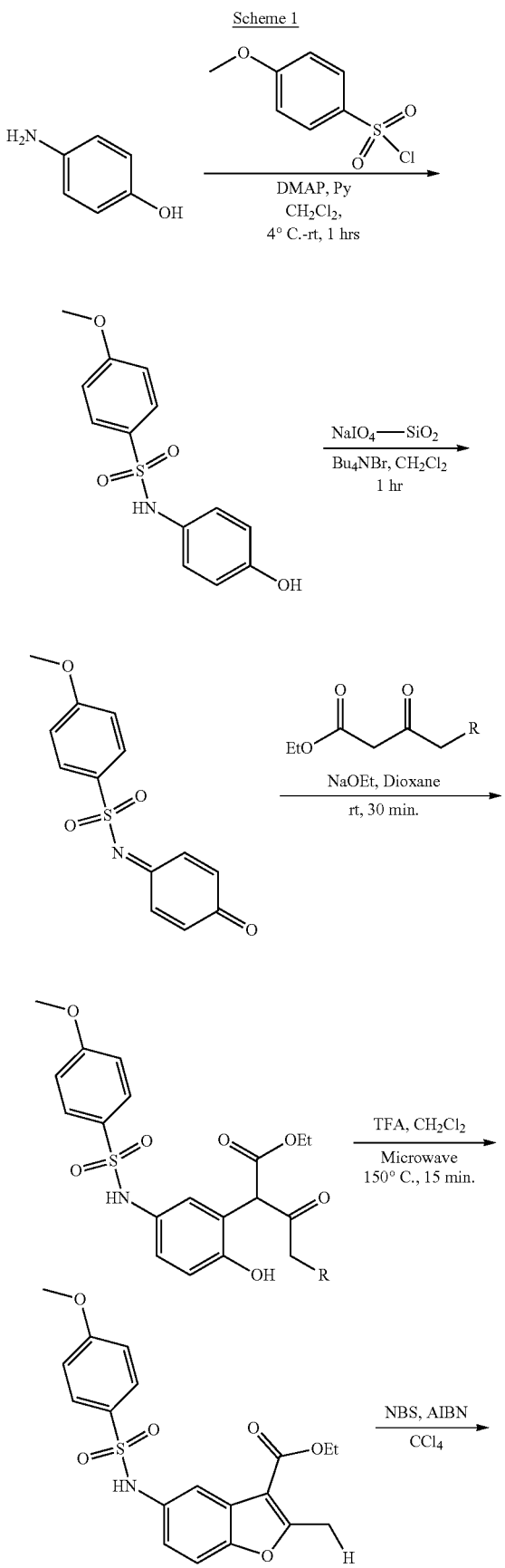

-continued

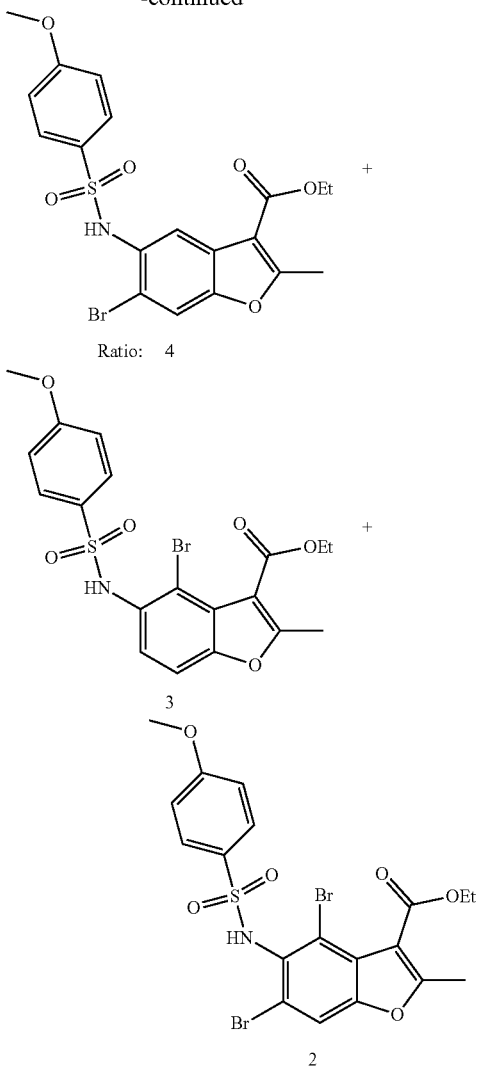

Biological Activity

Figure 1B:
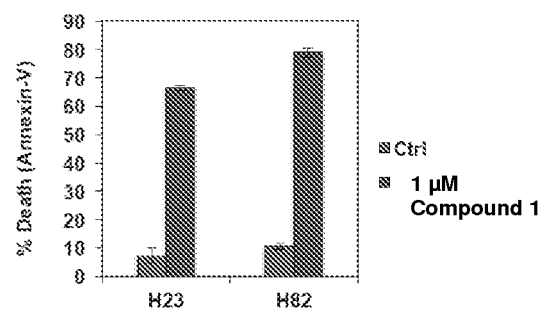
FIG. 1B shows 1 M of Compound 1 induces robust apoptosis in MCL-1-addicted cancer cell-lines, H23 and H82.

Compounds described herein are anti-proliferative agents and induce apoptosis in cancer cells. Compound 1 ("Mclin") induces apoptosis with an EC50 of 0.6 μM in MCL-1-addicted cancer cell-line, H23 (See, e.g., FIG. 1A). As a further example, 1 μM of Compound 1 induces robust apoptosis in MCL-1-addicted cancer cell-lines, H23 and H82 (See, e.g., FIG. 1B).

Figure 2A:
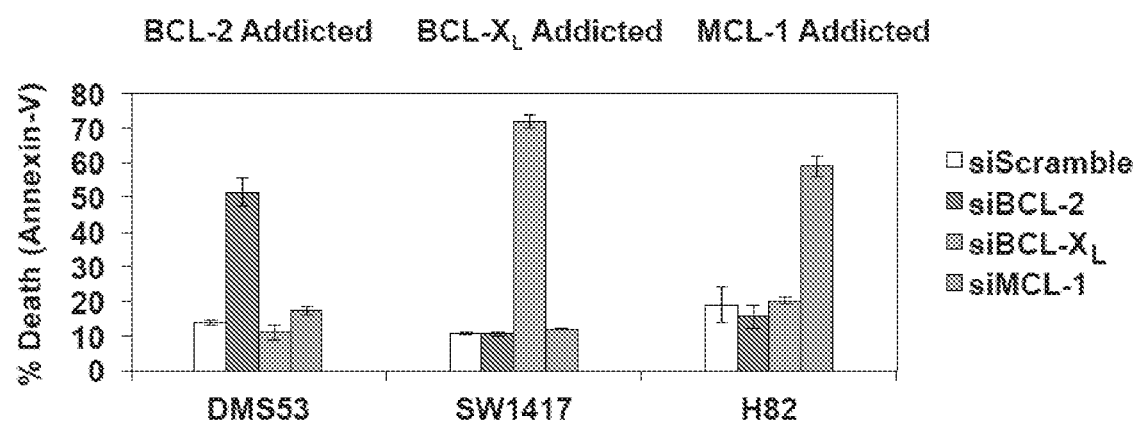
FIG. 2A shows three cell lines, DMS53, SW1417, and H82, are selectively addicted to BCL-2, BCL-$X_L$, and MCL-1, respectively.
Figure 2B:
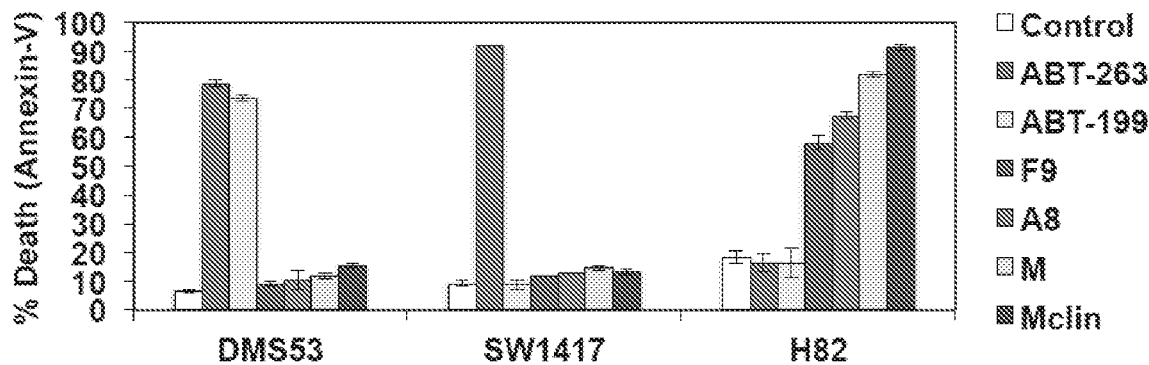
FIG. 2B shows apoptotic induction by Compound 1 ("Mclin") and other BCL-2 and BCL-$X_L$ inhibitors in DMS53, SW1417, and H82 cell lines. Compound 1 ("Mclin") selectively induces apoptosis in MCL-1 addicted cancer cell line over BCL-2 or BCL-$X_L$ addicted cancer cell lines.

Compounds provided herein are selective MCL-1 inhibitors and induce apoptosis in MCL-1 addicted cells over cells addicted to other BCL-2 family proteins. Compound 1 ("Mclin"), $F_9$, A8, and M selectively induce apoptosis in MCL-1 addicted cancer cell line over BCL-2 or BCL-$X_L$ addicted cancer cell lines (See, e.g., FIG. 2B). FIG. 3 shows the $EC_{50}$ of the indicated compounds in triggering apoptosis in MCL-1-addicted cancer cell lines including H23 and H82. These compounds do not induce apoptosis in cells deficient for the essential apoptotic effectors, Bax and Bak.

Figure 4:
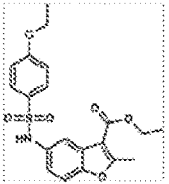
FIG. 4 shows the $EC_{50}$ of the indicated compounds in triggering apoptosis in the MCL-1-addicted cancer cell line H23.

Additional compounds have been shown to be effective anti-proliferative agents. FIG. 4 shows the $EC_{50}$ of exemplary compounds in triggering apoptosis in the MCL-1-addicted cancer cell line H23.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating cancer in a subject, the method comprising administering to the subject a therapeutically effective amount of a compound of Formula (IV):

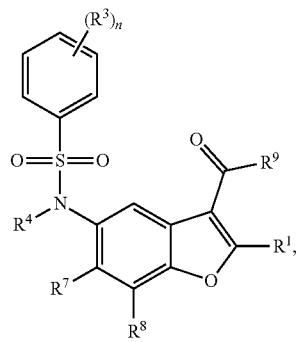

(IV)

or a pharmaceutically acceptable salt thereof, wherein:

R$^1$ is hydrogen or alkyl, wherein the alkyl is optionally substituted with one instance of —O—C$_{1-6}$ alkyl;

each instance of R$^3$ is independently halogen, alkyl, —OR$^{3A}$, —N(R$^{3B}$)$_2$, or acyl;

each instance of R$^{3A}$ is independently hydrogen or alkyl;

each instance of R$^{3B}$ is independently hydrogen or alkyl;

n is 0, 1, 2, or 3;

R$^4$ is hydrogen, alkyl, or acyl;

R$^7$ is hydrogen or alkyl;

R$^8$ is hydrogen, halogen, or alkyl;

R$^9$ is alkyl or —OR$^2$;

R$^2$ is hydrogen or alkyl; and wherein the cancer is lung cancer, colorectal cancer, multiple myeloma, or leukemia.

2. The method of claim 1, wherein the cancer is associated the addiction of a cell to a BCL-2 family member protein.

3. The method of claim 1 wherein the BCL-2 family member is an anti-apoptotic BCL-2 family member protein.

4. The method of claim 1 comprising administering a compound of Formula (IV), or a pharmaceutically acceptable salt thereof, wherein R$^9$ is —OR$^2$.

5. The method of claim 1 comprising administering a compound of Formula (IV), or a pharmaceutically acceptable salt thereof, wherein R$^7$ is hydrogen.

6. The method of claim 1 comprising administering a compound of Formula (IV), or a pharmaceutically acceptable salt thereof, wherein R$^8$ is halogen.

7. The method of claim 1 comprising administering a compound of Formula (IV), or a pharmaceutically acceptable salt thereof, wherein R$^8$ is hydrogen.

8. The method of claim 1, wherein the compound of Formula (IV) is of Formula (III):

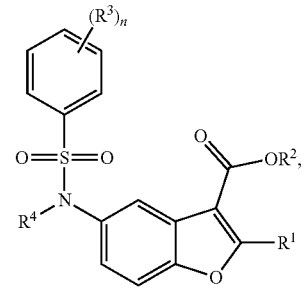

(III)

or a pharmaceutically acceptable salt thereof.

9. The method of claim 1 comprising administering a compound of Formula (IV), or a pharmaceutically acceptable salt thereof, wherein R$^1$ is C$_{1-6}$ alkyl.

10. The method of claim 1 comprising administering a compound of Formula (IV), or a pharmaceutically acceptable salt thereof, wherein R$^4$ is hydrogen.

11. The method of claim 1, wherein the compound is selected from the group consisting of:

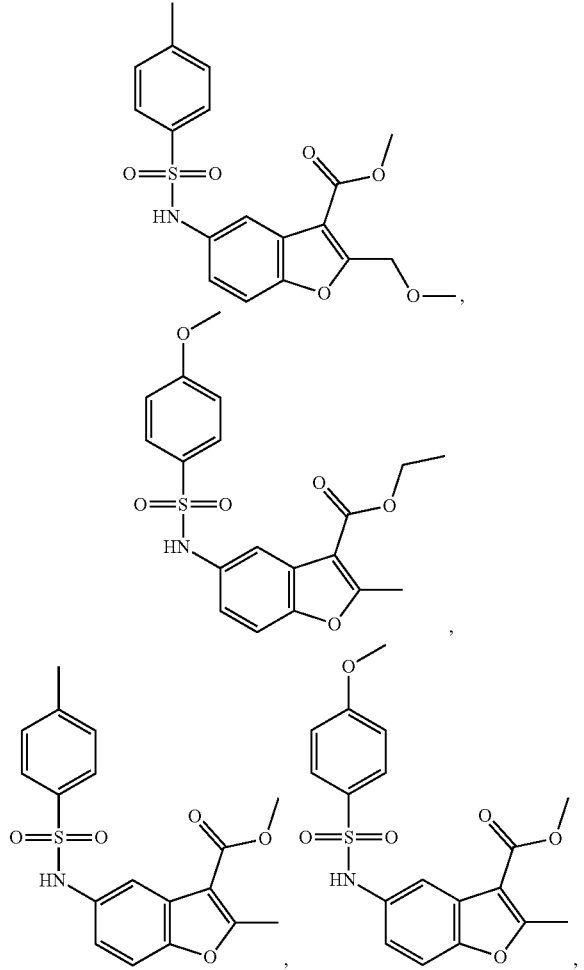

and pharmaceutically acceptable salts thereof.

12. The method of claim 1, wherein the compound is selected from the group consisting of:

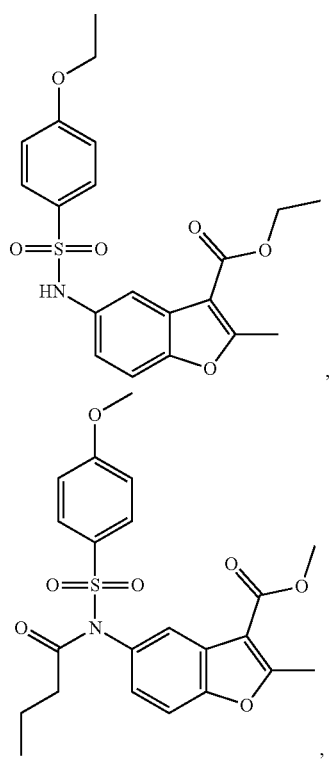
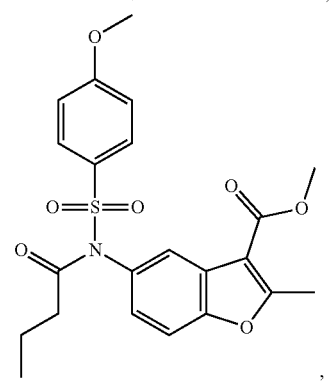
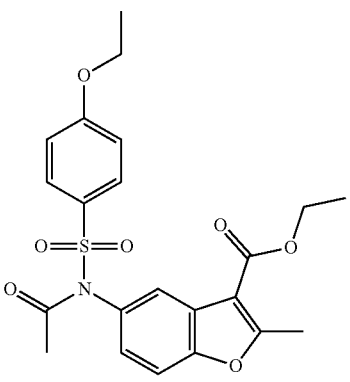
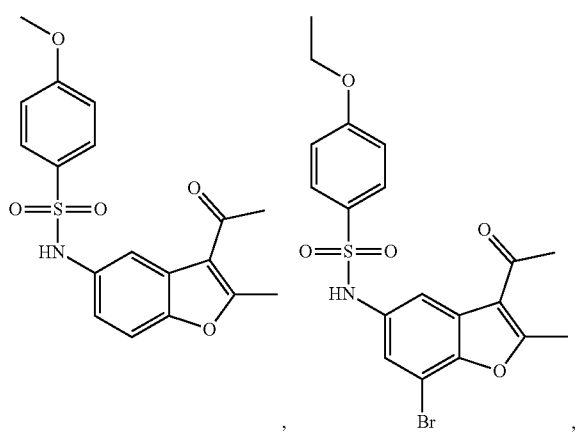
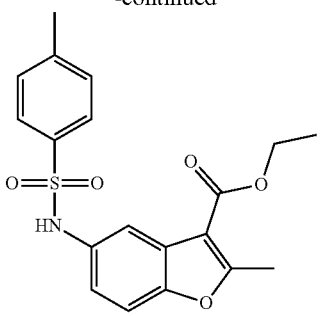
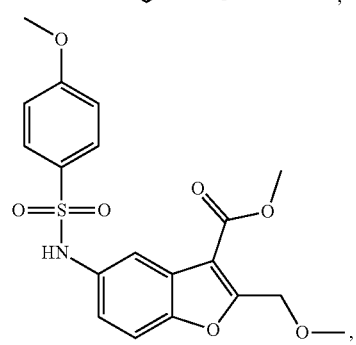
and pharmaceutically acceptable salts thereof.
13. The method of claim 1, wherein the compound of Formula (IV) is of Formula (III-a):
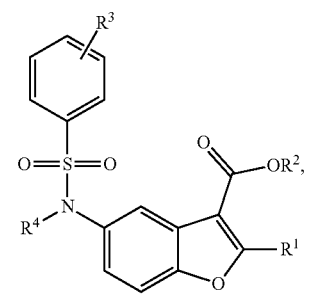
(III-a)
or a pharmaceutically acceptable salt thereof.
14. The method of claim 1, wherein the compound of Formula (IV) is of Formula (III-b):
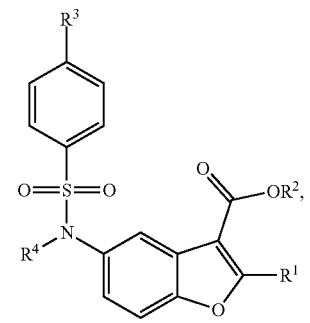
(III-b)
or a pharmaceutically acceptable salt thereof.

15. The method of claim 4 comprising administering a compound of Formula (IV), or a pharmaceutically acceptable salt thereof, wherein $R^2$ is $C_{1-6}$ alkyl.

16. The method of claim 1 comprising administering a compound of Formula (IV), or a pharmaceutically acceptable salt thereof, wherein at least one instance of $R^3$ is $C_{1-6}$ alkyl or $-OR^{3A}$.

17. The method of claim 16 comprising administering a compound of Formula (IV), or a pharmaceutically acceptable salt thereof, wherein at least one instance of $R^3$ is $-OR^{3A}$; and $R^{3A}$ is $C_{1-6}$ alkyl.

18. The method of claim 1 comprising administering a compound of Formula (IV), or a pharmaceutically acceptable salt thereof, wherein n is 1.

19. The method of claim 1 comprising administering a compound of Formula (IV), or a pharmaceutically acceptable salt thereof, wherein $R^4$ is $C_{1-6}$ acyl.

20. The method of claim 1 comprising administering a compound of Formula (IV), or a pharmaceutically acceptable salt thereof, wherein:

$R^1$ is $C_{1-6}$ alkyl;
each instance of $R^3$ is independently $C_{1-6}$ alkyl or $-OR^{3A}$;
each instance of $R^{3A}$ is independently $C_{1-6}$ alkyl;
n is 1;
$R^4$ is hydrogen or $-C(=O)C_{1-6}$ alkyl;
$R^7$ is hydrogen;
$R^8$ is hydrogen or halogen;
$R^9$ is $-OR^2$; and
$R^2$ is $C_{1-6}$ alkyl.

21. The method of claim 1, wherein the cancer is lung cancer.

22. The method of claim 1, wherein the cancer is colorectal cancer.

23. The method of claim 1, wherein the cancer is multiple myeloma.

24. The method of claim 1, wherein the cancer is leukemia.

25. The method of claim 1, wherein the cancer is associated with overexpression of a BCL-2 family member protein.

* * * * *